US011986424B2

(12) United States Patent
Holland et al.

(10) Patent No.: US 11,986,424 B2
(45) Date of Patent: May 21, 2024

(54) METHOD, SYSTEM, AND APPARATUS FOR IMAGING AND SURGICAL SCANNING OF THE IRIDO-CORNEAL ANGLE FOR LASER SURGERY OF GLAUCOMA

(71) Applicant: ViaLase, Inc., Aliso Viejo, CA (US)

(72) Inventors: Guy Holland, San Juan Capsitrano, CA (US); Tibor Juhasz, San Clemente, CA (US); Wesley W. Lummis, Rancho Santa Margarita, CA (US); Eric R. Mikula, Aliso Viejo, CA (US); Ferenc Raksi, Mission Viejo, CA (US); Manu Sharma, Ladera Ranch, CA (US); Hadi Srass, Yorba Linda, CA (US); Carlos G. Suarez, Tustin, CA (US)

(73) Assignee: ViaLase, Inc., Aliso Viejo, CA (US)

( * ) Notice: Subject to any disclaimer, the term of this patent is extended or adjusted under 35 U.S.C. 154(b) by 965 days.

(21) Appl. No.: 16/943,909

(22) Filed: Jul. 30, 2020

(65) Prior Publication Data

US 2020/0352785 A1 Nov. 12, 2020

Related U.S. Application Data

(63) Continuation-in-part of application No. 16/125,597, filed on Sep. 7, 2018, now Pat. No. 11,173,067, and
(Continued)

(51) Int. Cl.
*A61F 9/007* (2006.01)
*A61F 9/008* (2006.01)

(52) U.S. Cl.
CPC ........ *A61F 9/00781* (2013.01); *A61F 9/0084* (2013.01); *A61F 2009/00851* (2013.01); *A61F 2009/00872* (2013.01)

(58) Field of Classification Search
CPC .............. A61F 9/00825; A61F 9/00781; A61F 9/0084; A61F 2009/00851;
(Continued)

(56) References Cited

U.S. PATENT DOCUMENTS 6,251,103 B1 6/2001 Berlin
6,482,199 B1 11/2002 Neev
(Continued)

FOREIGN PATENT DOCUMENTS

CN 104382689 B 9/2016
EP 1080706 A1 3/2001
(Continued)

OTHER PUBLICATIONS

PCT/US2019/039033, Int'l Search Report & Written Opinion (dated Oct. 2, 2019).
(Continued)

*Primary Examiner* — Mark W. Bockelman
(74) *Attorney, Agent, or Firm* — LOZA & LOZA, LLP; David S. Sarisky

(57) ABSTRACT

A method of imaging and treating ocular tissue of an eye having a cornea, an iris, an anterior chamber, an irido-corneal angle, and a direction of view includes establishing a common optical path through the cornea and the anterior chamber into the irido-corneal angle for each of an optical coherence tomography (OCT) beam and a laser beam, where the common optical path is offset from an optical axis within the direction of view. The method also includes obtaining a circumferential OCT image of the irido-corneal angle, obtaining an azimuthal OCT image of the irido-corneal angle, and determining a treatment pattern for a volume of ocular tissue of the irido-corneal angle based on the circumferential OCT image and the azimuthal OCT image. The
(Continued)

method further includes delivering optical energy through the laser beam in accordance with the treatment pattern.

26 Claims, 27 Drawing Sheets
(1 of 27 Drawing Sheet(s) Filed in Color)

Related U.S. Application Data a continuation-in-part of application No. 16/036,833, filed on Jul. 16, 2018, now Pat. No. 10,821,023.

(58) Field of Classification Search
CPC .. A61F 2009/00855; A61F 2009/00868; A61F 2009/00872; A61F 2009/00897; A61F 2009/00891
See application file for complete search history.

(56) References Cited

U.S. PATENT DOCUMENTS

| | | |
|---|---|---|
| 6,682,523 B2 | 1/2004 | Shadduck |
| 6,989,007 B2 | 1/2006 | Shadduck |
| 7,131,968 B2 | 11/2006 | Bendett et al. |
| 7,192,412 B1 | 3/2007 | Zhou et al. |
| 7,282,046 B2 | 10/2007 | Simon |
| 7,351,241 B2 | 4/2008 | Bendett et al. |
| 8,011,504 B1 | 9/2011 | Farberov |
| 8,171,937 B2 | 5/2012 | Bendett et al. |
| 8,230,866 B2 | 7/2012 | Hauger et al. |
| 8,394,084 B2 | 3/2013 | Palankar et al. |
| 8,523,926 B2 | 9/2013 | Neev |
| 8,540,659 B2 | 9/2013 | Berlin |
| 8,568,393 B2 * | 10/2013 | Palanker ............... A61F 9/008 606/4 |
| 8,679,089 B2 | 3/2014 | Berlin |
| 8,687,866 B2 | 4/2014 | Marziliano et al. |
| 8,709,001 B2 | 4/2014 | Blumenkranz et al. |
| 8,845,624 B2 | 9/2014 | Raksi et al. |
| 8,920,407 B2 | 12/2014 | Raksi et al. |
| 9,033,963 B2 | 5/2015 | Vera et al. |
| 9,044,303 B2 | 6/2015 | Kurtz et al. |
| 9,101,448 B2 | 8/2015 | Blumenkranz et al. |
| 9,259,153 B2 | 2/2016 | Goto |
| 9,259,354 B2 | 2/2016 | Horvath et al. |
| 9,265,411 B2 | 2/2016 | Chen et al. |
| 9,271,870 B2 | 3/2016 | Palanker et al. |
| 9,301,878 B2 | 4/2016 | Raksi et al. |
| 9,320,650 B2 | 4/2016 | Bendett et al. |
| 9,441,946 B2 | 9/2016 | Massow et al. |
| 9,456,925 B2 | 10/2016 | Kurtz et al. |
| 9,474,648 B2 | 10/2016 | Palanker et al. |
| 9,498,295 B2 | 11/2016 | Palanker |
| 9,517,006 B2 | 12/2016 | Izatt et al. |
| 9,554,702 B2 | 1/2017 | Papac et al. |
| 9,560,963 B2 | 2/2017 | Buckland et al. |
| 9,603,741 B2 | 3/2017 | Berlin |
| 9,603,744 B2 | 3/2017 | Hailmann et al. |
| 9,629,750 B2 | 4/2017 | Dambacher et al. |
| 9,642,746 B2 | 5/2017 | Berlin |
| 9,681,985 B2 | 6/2017 | Andersen et al. |
| 9,724,238 B2 | 8/2017 | Heitel |
| 9,750,640 B2 | 9/2017 | Palanker et al. |
| 9,820,883 B2 | 11/2017 | Berlin |
| 9,833,357 B2 | 12/2017 | Berlin |
| 9,844,464 B2 | 12/2017 | Bendett et al. |
| 9,936,868 B2 | 4/2018 | Izatt et al. |
| 10,064,757 B2 | 9/2018 | Berlin |
| 10,073,515 B2 | 9/2018 | Awdeh |
| 10,159,600 B2 | 12/2018 | Horvath et al. |
| 10,159,601 B2 | 12/2018 | Berlin |
| 10,165,941 B2 | 1/2019 | Walsh et al. |
| 10,179,066 B2 | 1/2019 | Badawi et al. |
| 10,195,078 B2 | 2/2019 | Horvath et al. |
| 10,195,079 B2 | 2/2019 | Horvath et al. |
| 10,195,080 B2 | 2/2019 | Berlin |
| 10,238,281 B2 | 3/2019 | Isogai et al. |
| 10,238,541 B2 | 3/2019 | Yee et al. |
| 10,292,868 B2 | 5/2019 | Chew et al. |
| 10,335,314 B2 | 7/2019 | Berlin |
| 10,335,315 B2 | 7/2019 | Goldshleger et al. |
| 10,360,683 B2 | 7/2019 | Iwase et al. |
| 10,362,935 B2 | 7/2019 | Dastmalchi et al. |
| 10,362,936 B2 | 7/2019 | Buckland et al. |
| 10,363,169 B2 | 7/2019 | Belkin et al. |
| 10,363,172 B2 | 7/2019 | Kawai et al. |
| 10,383,689 B2 | 8/2019 | Berlin |
| 10,390,883 B2 | 8/2019 | Deladurantaye et al. |
| 10,398,306 B2 | 9/2019 | Liu |
| 10,406,034 B2 | 9/2019 | Siegele |
| 10,426,548 B2 | 10/2019 | Tearney et al. |
| 10,454,237 B2 | 10/2019 | Yu et al. |
| 10,456,030 B2 | 10/2019 | Buckland et al. |
| 10,456,209 B2 | 10/2019 | Peyman |
| 10,478,060 B2 | 11/2019 | Kubota |
| 10,493,274 B2 | 12/2019 | Irazoqui et al. |
| 10,499,809 B2 | 12/2019 | Kalina, Jr. et al. |
| 10,500,094 B2 | 12/2019 | Buzawa et al. |
| 10,517,760 B2 | 12/2019 | Berlin |
| 10,524,822 B2 | 1/2020 | Aljuri et al. |
| 10,537,476 B2 | 1/2020 | Ha et al. |
| 10,542,883 B2 | 1/2020 | Gooi et al. |
| 10,543,122 B2 | 1/2020 | Kahook |
| 10,543,123 B2 | 1/2020 | Neev |
| 10,568,763 B2 | 2/2020 | Vera et al. |
| 10,588,694 B1 | 3/2020 | Neev |
| 10,596,036 B2 | 3/2020 | Pinchuk |
| 10,603,214 B2 | 3/2020 | Bigler et al. |
| 10,603,216 B2 | 3/2020 | Kurtz et al. |
| 10,653,557 B2 | 5/2020 | Rill et al. |
| 10,674,906 B2 | 6/2020 | Kalina, Jr. et al. |
| 10,687,978 B2 | 6/2020 | Berlin |
| 10,702,416 B2 | 7/2020 | Belkin et al. |
| 10,744,033 B2 | 8/2020 | Baerveldt et al. |
| 10,744,034 B2 | 8/2020 | Homer |
| 10,758,418 B2 | 9/2020 | Vold et al. |
| 10,765,559 B2 | 9/2020 | Berlin |
| 10,779,988 B2 | 9/2020 | Fu et al. |
| 10,799,113 B2 | 10/2020 | Vadakke Matham et al. |
| 10,821,023 B2 | 11/2020 | Raksi |
| 10,821,024 B2 | 11/2020 | Raksi |
| 10,888,461 B2 | 1/2021 | Orthaber et al. |
| 10,898,381 B2 | 1/2021 | Bendett et al. |
| 11,019,996 B2 | 6/2021 | Kalina, Jr. et al. |
| 11,019,997 B2 | 6/2021 | Kalina, Jr. et al. |
| 11,026,860 B2 | 6/2021 | Andersen et al. |
| 11,039,958 B2 | 6/2021 | Berlin |
| 11,110,006 B2 | 9/2021 | Raksi |
| 11,147,708 B2 | 10/2021 | Horvath et al. |
| 11,166,630 B2 | 11/2021 | Frisken et al. |
| 11,173,067 B2 | 11/2021 | Raksi |
| 11,246,754 B2 | 2/2022 | Holland et al. |
| 11,316,318 B2 | 4/2022 | Yu et al. |
| 11,376,160 B2 | 7/2022 | Romano et al. |
| 11,382,794 B2 | 7/2022 | Sacks et al. |
| 11,395,765 B2 | 7/2022 | Goldshleger et al. |
| 11,399,981 B2 | 8/2022 | Fu et al. |
| 2002/0013572 A1 | 1/2002 | Berlin |
| 2004/0070761 A1 | 4/2004 | Horvath et al. |
| 2006/0200113 A1 | 9/2006 | Haffner |
| 2008/0058781 A1 | 3/2008 | Langeweyde et al. |
| 2009/0012507 A1 | 1/2009 | Culbertson et al. |
| 2009/0093798 A1 * | 4/2009 | Charles ............... A61F 9/00823 606/4 |
| 2009/0118718 A1 | 5/2009 | Raksi et al. |
| 2009/0149840 A1 | 6/2009 | Kurtz |
| 2009/0149841 A1 | 6/2009 | Kurtz |
| 2009/0157062 A1 | 6/2009 | Hauger et al. |
| 2010/0130966 A1 | 5/2010 | Brownell |
| 2011/0092965 A1 | 4/2011 | Slatkine et al. |
| 2012/0257167 A1 | 10/2012 | Gille et al. |
| 2012/0259321 A1 | 10/2012 | Vera et al. |
| 2012/0283557 A1 * | 11/2012 | Berlin ............... A61F 9/009 600/407 |

(56) References Cited

U.S. PATENT DOCUMENTS

| | | |
|---|---|---|
| 2012/0303007 A1 | 11/2012 | Loesel et al. |
| 2013/0085484 A1 | 4/2013 | Van Valen et al. |
| 2013/0103011 A1* | 4/2013 | Grant .................. A61F 9/00825 |
| | | 606/4 |
| 2013/0197634 A1 | 8/2013 | Palanker et al. |
| 2013/0237972 A1 | 9/2013 | Raksi |
| 2014/0128853 A1 | 5/2014 | Angeley et al. |
| 2014/0142599 A1 | 5/2014 | Jeglorz et al. |
| 2014/0216468 A1 | 8/2014 | Goldshleger et al. |
| 2014/0236066 A1 | 8/2014 | Horvath et al. |
| 2014/0288485 A1 | 9/2014 | Berlin |
| 2014/0354951 A1 | 12/2014 | Izatt et al. |
| 2015/0077528 A1 | 3/2015 | Awdeh |
| 2015/0080783 A1 | 3/2015 | Berlin |
| 2015/0157505 A1 | 6/2015 | Neev |
| 2015/0297408 A1 | 10/2015 | Dolzan et al. |
| 2015/0305939 A1 | 10/2015 | Vera et al. |
| 2015/0305940 A1 | 10/2015 | Vera et al. |
| 2015/0313759 A1 | 11/2015 | Vera et al. |
| 2015/0335477 A1 | 11/2015 | Schuele et al. |
| 2015/0359426 A1 | 12/2015 | Buckland et al. |
| 2016/0095751 A1 | 4/2016 | Berlin |
| 2016/0095752 A1 | 4/2016 | Srinivasan et al. |
| 2016/0213512 A1 | 7/2016 | Palanker et al. |
| 2016/0220110 A1 | 8/2016 | Vogler et al. |
| 2017/0020732 A1 | 1/2017 | Berlin |
| 2017/0027437 A1 | 2/2017 | Neal et al. |
| 2017/0042736 A9 | 2/2017 | Berlin |
| 2017/0119579 A9 | 5/2017 | Berlin |
| 2017/0127938 A1 | 5/2017 | Izatt et al. |
| 2017/0202708 A1 | 7/2017 | Berlin |
| 2017/0326003 A1 | 11/2017 | Schuele et al. |
| 2018/0028355 A1 | 2/2018 | Raksi |
| 2018/0207029 A1 | 7/2018 | Herekar et al. |
| 2018/0221205 A1 | 8/2018 | Berlin |
| 2018/0235462 A1 | 8/2018 | Gooi et al. |
| 2018/0360310 A1 | 12/2018 | Berlin |
| 2018/0360655 A1 | 12/2018 | Berlin |
| 2019/0083313 A1 | 3/2019 | Berlin |
| 2019/0083314 A1 | 3/2019 | Berlin |
| 2019/0117459 A1 | 4/2019 | Berlin |
| 2019/0240070 A1 | 8/2019 | Schmid et al. |
| 2019/0357768 A1 | 11/2019 | Shareef |
| 2020/0016000 A1 | 1/2020 | Raksi |
| 2020/0016002 A1 | 1/2020 | Raksi |
| 2020/0078216 A1 | 3/2020 | Raksi |
| 2020/0078217 A1 | 3/2020 | Raksi |
| 2020/0078218 A1 | 3/2020 | Holland et al. |
| 2020/0390605 A1 | 12/2020 | Raksi |
| 2021/0022921 A1 | 1/2021 | Berlin |
| 2021/0052416 A1 | 2/2021 | Herekar et al. |
| 2021/0298945 A1 | 9/2021 | Juhasz et al. |

FOREIGN PATENT DOCUMENTS

| | | |
|---|---|---|
| EP | 1208792 A1 | 5/2002 |
| EP | 1017308 B1 | 6/2003 |
| EP | 2384727 A1 | 11/2011 |
| JP | S58187911 A | 11/1983 |
| JP | 2005508704 A | 4/2005 |
| JP | 2016504964 A | 2/2016 |
| JP | 2016193033 A | 11/2016 |
| WO | 2013188885 A1 | 12/2013 |
| WO | 2017031570 A1 | 3/2017 |
| WO | 2018049246 A1 | 3/2018 |
| WO | 2019060756 A1 | 3/2019 |
| WO | 2019173759 A1 | 9/2019 |

OTHER PUBLICATIONS

PCT/US2019/039043, Int'l Search Report & Written Opinion (dated Oct. 10, 2019).
PCT/US2019/042553, Int'l Search Report & Written Opinion (dated Oct. 10, 2019).
PCT/US2019/042571, Int'l Search Report & Written Opinion (dated Oct. 15, 2019).
PCT/US2019/042553, Written Opinon (dated Jul. 20, 2020).
Brubaker, "Goldmann's equation and clinical measures of aqueous dynamics". Experimental Eye Research, vol. 78, Issue 3, pp. 633-637 (2004).
Grant, "Tonographic method for measuring the facility and rate of aqueous flow in human eyes". Arch. Ophthalmol. 44(2), pp. 204-214 (1950).
Hann et al. Anatomic changes in schlemm's canal and collector channels in normal and primary open-angle glaucoma eyes using low and high perfusion pressures. Glaucoma, vol. 55:9 (Sep. 2014).
Johnstone, "The aqueous outflow system as a mechanical pump: evidence from examination of tissue and aqueous movement in human and non-human primates". J Glaucoma, vol. 13:5, pp. 421-438 (Oct. 2004).
Jones et al., "New methods of measuring the rate of aqueous flow in man with fluorescein". Experimental Eye Research, vol. 5:3, pp. 208-220 (Jul. 1966).
Junker et al. Intraoperative optical coherence tomography and ab interno trabecular meshwork surgery with the trabectome. Clin Ophthalmol. 11: 1755-1760 (Sep. 28, 2017).
Kagemann et al. "Characterisation of Schlemm's canal cross-sectional area." Br J Ophthalmol 2014, 98 (Suppl. II) (Mar. 3, 2014).
McNabb et al. "Complete 360° circumferential gonioscopic optical coherence tomography imaging of the ridocorneal angle." Biomedical Optics Express vol. 6, Issue 4, pp. 1376-1391 (2015).
Rosenquist et al., "Ouflow resistance of enucleated human eyes at two different perfusion pressures and different extents of trabeculotomy". Current Eye Research, vol. 8:12, pp. 1233-1240 (1989).
Xin et al. "OCT study of mechanical properties associated with Trabecular meshwork and collector channel motion in human eyes." PLoS One. 2016; 11(9): e0162048. doi: 10.1371/journal.pone.0162048 (Sep. 6, 2016).
Xin et al. "Aqueous outflow regulation: optical coherence tomography implicates pressure-dependent tissue motion." Experimental Eye Research, vol. 158, pp. 171-186 (May 2017).
PCT/US2021/042261. International Search Report and Written Opinion dated Jan. 14, 2022. (20 pages).
PCT/US2019/039043, IPEA Written Opinion (dated Aug. 17, 2020).
PCT/US2019/039033, IPEA Written Opinion (dated Jul. 6, 2020).
PCT/US2021/042261. IPRP (dated Jun. 13, 2022).

* cited by examiner

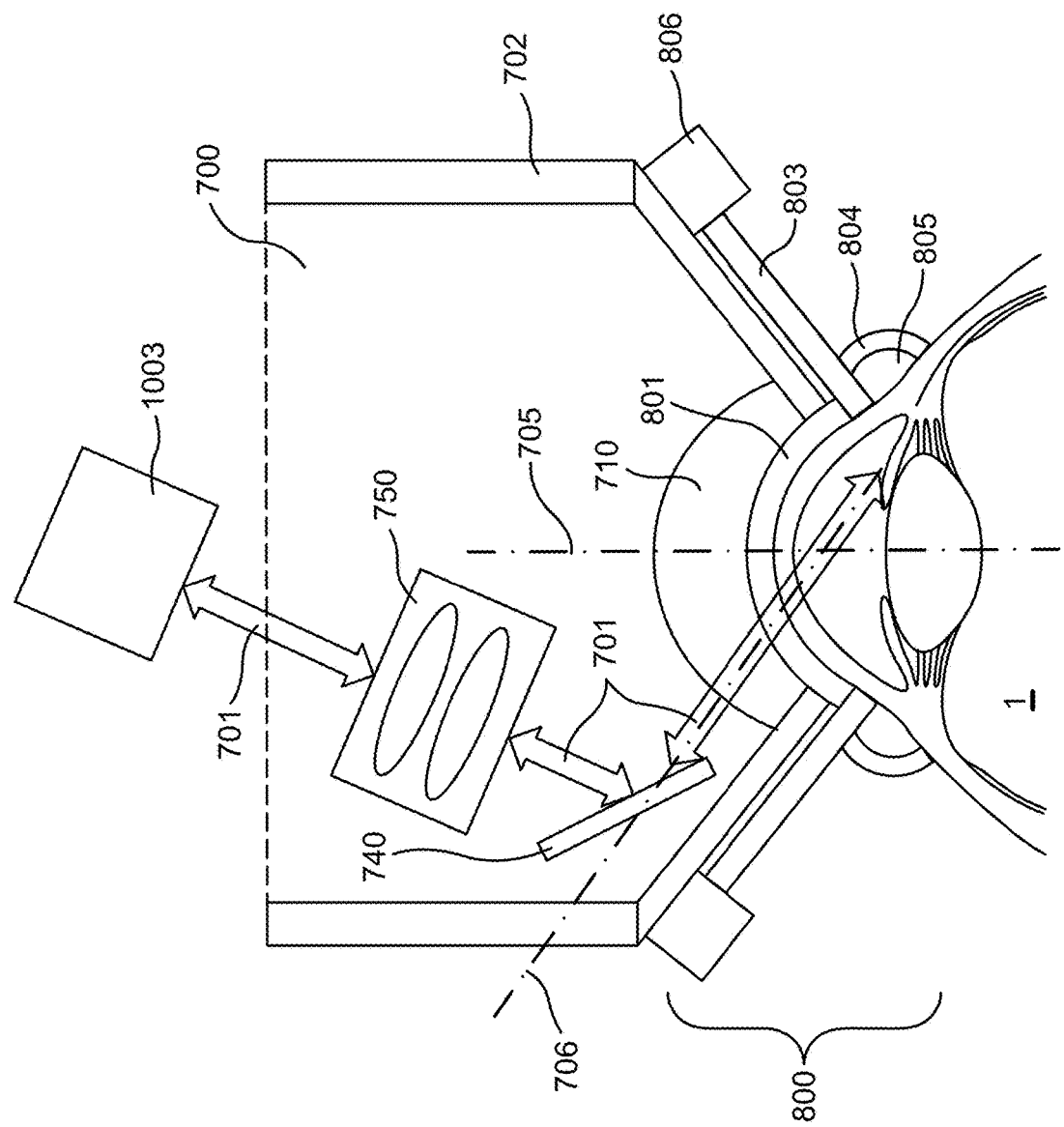

METHOD, SYSTEM, AND APPARATUS FOR IMAGING AND SURGICAL SCANNING OF THE IRIDO-CORNEAL ANGLE FOR LASER SURGERY OF GLAUCOMA

CROSS-REFERENCE TO RELATED APPLICATIONS

This application is a continuation-in-part of U.S. patent application Ser. No. 16/036,833, filed Jul. 16, 2018, for "Integrated Surgical System and Method for Treatment in the Irido-Corneal Angle of the Eye," and a continuation-in-part of U.S. patent application Ser. No. 16/125,597, filed Sep. 7, 2018, for "Surgical System and Procedure for Precise Intraocular Pressure Reduction," the entire disclosures of which are incorporated herein by reference.

TECHNICAL FIELD

The present disclosure relates generally to the field of medical devices and treatment of diseases in ophthalmology, and more particularly to systems, apparatuses, and methods for imaging and surgical scanning of the anterior chamber angle, i.e., the irido-corneal angle, of the eye, for laser surgery treatment of glaucoma.

BACKGROUND

Before describing the different types of glaucoma and current diagnosis and treatments options, a brief overview of the anatomy of the eye is provided.

Anatomy of the Eye

With reference to FIGS. 1-3, the outer tissue layer of the eye 1 includes a sclera 2 that provides the structure of the eye's shape. In front of the sclera 2 is a cornea 3 that is comprised of transparent layers of tissue that allow light to enter the interior of the eye. Inside the eye 1 is a crystalline lens 4 that is connected to the eye by fiber zonules 5, which are connected to the ciliary body 6. Between the crystalline lens 4 and the cornea 3 is an anterior chamber 7 that contains a flowing clear liquid called aqueous humor 8. Encircling the perimeter of the crystalline lens 4 is an iris 9 which forms a pupil around the approximate center of the crystalline lens. A posterior chamber 23 is an annular volume behind the iris 9 and bounded by the ciliary body 6, fiber zonules 5, and the crystalline lens 4. The vitreous humor 10 is located between the crystalline lens 4 and the retina 11. Light entering the eye is optically focused through the cornea 3 and crystalline lens.

With reference to FIG. 2, the corneoscleral junction of the eye is the portion of the anterior chamber 7 at the intersection of the iris 9, the sclera 2, and the cornea 3. The anatomy of the eye 1 at the corneoscleral junction includes a trabecular meshwork 12. The trabecular meshwork 12 is a fibrous network of tissue that encircles the iris 9 within the eye 1. In simplified, general terms the tissues of the corneoscleral junction are arranged as follows: the iris 9 meets the ciliary body 6, the ciliary body meets with the underside of the scleral spur 14, the top of the scleral spur serves as an attachment point for the bottom of the trabecular meshwork 12. The ciliary body is present mainly in the posterior chamber, but also extends into the very corner of the anterior chamber 7. The network of tissue layers that make up the trabecular meshwork 12 are porous and thus present a pathway for the egress of aqueous humor 8 flowing from the anterior chamber 7. This pathway may be referred to herein as an aqueous humor outflow pathway, an aqueous outflow pathway, or simply an outflow pathway.

Referring to FIG. 3, the pathway formed by the pores in the trabecular meshwork 12 connect to a set of thin porous tissue layers called the uveal 15, the corneoscleral meshwork 16, and the juxtacanalicular tissue 17. The juxtacanalicular tissue 17, in turn, abuts a structure called Schlemm's canal 18. The Schlemm's canal 18 carries a mixture of aqueous humor 8 and blood from the surrounding tissue to drain into the venous system though a system of collector channels 19. As shown in FIG. 2, the vascular layer of the eye, referred to as the choroid 20, is next to the sclera 2. A space, called the suprachoroidal space 21, may be present between the choroid 20 and the sclera 2. The general region near the periphery of the wedge between the cornea 3 and the iris 9, running circumferentially is called the irido-corneal angle 13. The irido-corneal angle 13 may also be referred to as the corneal angle of the eye or simply the angle of the eye. The ocular tissues illustrated in FIG. 3 are all considered to be within the irido-corneal angle 13.

With reference to FIG. 4, two possible outflow pathways for the movement of aqueous humor 8 include a trabecular outflow pathway 40 and a uveoscleral outflow pathway 42. Aqueous humor 8, which is produced by the ciliary body 6, flows from the posterior chamber 23 through the pupil into the anterior chamber 7, and then exits the eye through one or more of the two different outflow pathways 40, 42. Approximately 90% of the aqueous humor 8 leaves via the trabecular outflow pathway 40 by passing through the trabecular meshwork 12, into the Schlemm's canal 18 and through one or more plexus of collector channels 19 before draining through a drain path 41 into the venous system. Any remaining aqueous humor 8 leaves primarily through the uveoscleral outflow pathway 42. The uveoscleral outflow pathway 42 passes through the ciliary body 6 face and iris root into the suprachoroidal space 21 (shown in FIG. 2). Aqueous humor 8 drains from the suprachoroidal space 21, from which it can be drained through the sclera 2.

The intra-ocular pressure of the eye depends on the aqueous humor 8 outflow through the trabecular outflow pathway 40 and the resistance to outflow of aqueous humor through the trabecular outflow pathway. The intra-ocular pressure of the eye is largely independent of the aqueous humor 8 outflow through the uveoscleral outflow pathway 42. Resistance to the outflow of aqueous humor 8 through the trabecular outflow pathway 40 may lead to elevated intra-ocular pressure of the eye, which is a widely recognized risk factor for glaucoma. Resistance through the trabecular outflow pathway 40 may increase due a collapsed or malfunctioning Schlemm's canal 18 and trabecular meshwork 12.

Referring to FIG. 5, as an optical system, the eye 1 is represented by an optical model described by idealized centered and rotationally symmetrical surfaces, entrance and exit pupils, and six cardinal points: object and image space focal points, first and second principal planes, and first and second nodal points. Angular directions relative to the human eye are often defined with respect to an optical axis 24, a visual axis 26, a pupillary axis 28 and a line of sight 29 of the eye. The optical axis 24 is the symmetry axis, the line connecting the vertices of the idealized surfaces of the eye. The visual axis 26 connects the foveal center 22 with the first and second nodal points to the object. The line of sight 29 connects the fovea through the exit and entrance pupils to the object. The pupillary axis 28 is normal to the anterior surface of the cornea 3 and directed to the center of the entrance pupil. These axes of the eye differ from one another only by a few degrees and fall within a range of what is generally referred to as the direction of view.

Glaucoma

Glaucoma is a group of diseases that can harm the optic nerve and cause vision loss or blindness. It is the leading cause of irreversible blindness. Approximately 80 million people are estimated to have glaucoma worldwide and of these, approximately 6.7 million are bilaterally blind. More than 2.7 million Americans over age 40 have glaucoma. Symptoms start with loss of peripheral vision and can progress to blindness.

There are two forms of glaucoma, one is referred to as closed-angle glaucoma, the other as open-angled glaucoma. With reference to FIGS. 1-4, in closed-angle glaucoma, the iris 9 in a collapsed anterior chamber 7 may obstruct and close off the flow of aqueous humor 8. In open-angle glaucoma, which is the more common form of glaucoma, the permeability of ocular tissue may be affected by irregularities in the juxtacanalicular tissue 17 and inner wall of Schlemm's canal 18a, blockage of tissue in the irido-corneal angle 13 along the trabecular outflow pathway 40.

As previously stated, elevated intra-ocular pressure (IOP) of the eye, which damages the optic nerve, is a widely recognized risk factor for glaucoma. However, not every person with increased eye pressure will develop glaucoma, and glaucoma can develop without increased eye pressure. Nonetheless, it is desirable to reduce elevated IOP of the eye to reduce the risk of glaucoma.

Methods of diagnosing conditions of the eye of a patient with glaucoma include visual acuity tests and visual field tests, dilated eye exams, tonometry, i.e. measuring the intra-ocular pressure of the eye, and pachymetry, i.e. measuring the thickness of the cornea. Deterioration of vision starts with the narrowing of the visual field and progresses to total blindness. Imaging methods include slit lamp examination, observation of the irido-corneal angle with a gonioscopic lens and optical coherence tomography (OCT) imaging of the anterior chamber and the retina Once diagnosed, some clinically proven treatments are available to control or lower the intra-ocular pressure of the eye to slow or stop the progress of glaucoma. The most common treatments include: 1) medications, such as eye drops or pills, 2) laser surgery, and 3) traditional surgery. Treatment usually begins with medication. However, the efficacy of medication is often hindered by patient non-compliance. When medication does not work for a patient, laser surgery is typically the next treatment to be tried. Traditional surgery is invasive, more high risk than medication and laser surgery, and has a limited time window of effectiveness. Traditional surgery is thus usually reserved as a last option for patients whose eye pressure cannot be controlled with medication or laser surgery.

Laser Surgery

With reference to FIG. 2, laser surgery for glaucoma targets the trabecular meshwork 12 to decrease aqueous humor 8 flow resistance. Common laser treatments include Argon Laser Trabeculoplasty (ALT), Selective Laser Trabeculoplasty (SLT) and Excimer Laser Trabeculostomy (ELT).

ALT was the first laser trabeculoplasty procedure. During the procedure, an argon laser of 514 nm wavelength is applied to the trabecular meshwork 12 around 180 degrees of the circumference of the irido-corneal angle 13. The argon laser induces a thermal interaction with the ocular tissue that produces openings in the trabecular meshwork 12. ALT, however, causes scarring of the ocular tissue, followed by inflammatory responses and tissue healing that may ultimately close the opening through the trabecular meshwork 12 formed by the ALT treatment, thus reducing the efficacy of the treatment. Furthermore, because of this scarring, ALT therapy is typically not repeatable.

SLT is designed to lower the scarring effect by selectively targeting pigments in the trabecular meshwork 12 and reducing the amount of heat delivered to surrounding ocular tissue. During the procedure, a solid-state laser of 532 nm wavelength is applied to the trabecular meshwork 12 between 180 to 360 degrees around the circumference of the irido-corneal angle 13 to remove the pigmented cells lining the trabeculae which comprise the trabecular meshwork. The collagen ultrastructure of the trabecular meshwork is preserved during SLT. 12. SLT treatment can be repeated, but subsequent treatments have lower effects on IOP reduction.

ELT uses a 308 nm wavelength ultraviolet (UV) excimer laser and non-thermal interaction with ocular tissue to treat the trabecular meshwork 12 and inner wall of Schlemm's canal in a manner that does not invoke a healing response. Therefore, the IOP lowering effect lasts longer. However, because the UV light of the laser cannot penetrate deep into the eye, the laser light is delivered to the trabecular meshwork 12 via an optical fiber inserted into the eye 1 through an opening and the fiber is brought into contact with the trabecular meshwork. The procedure is highly invasive and is generally practiced simultaneously with cataract procedures when the eye is already surgically open. Like ALT and SLT, ELT also lacks control over the amount of IOP reduction.

None of these existing laser treatments represents an ideal treatment for glaucoma. Accordingly, what is needed are systems, apparatuses, and method for laser surgery treatment of glaucoma that effectively reduce IOP non-invasively without significant scarring of tissue, so the treatment may be completed in a single procedure and repeated at a later time if necessary.

Such systems, apparatuses, and methods for laser surgery treatment of glaucoma are disclosed in U.S. patent application Ser. No. 16/036,833, filed Jul. 16, 2018, for "Integrated Surgical System and Method for Treatment in the Irido-Corneal Angle of the Eye," and U.S. patent application Ser. No. 16/125,597, filed Sep. 7, 2018, for "Surgical System and Procedure for Precise Intraocular Pressure Reduction." These applications disclose laser surgery techniques that employ OCT imaging of the irido-corneal angle. What is further needed in the field of laser treatment of glaucoma are systems, apparatuses, and methods that enable OCT imaging of the irido-corneal angle from multiple perspectives, and efficient OCT imaging around the entire circumference of the irido-corneal angle.

SUMMARY

The present disclosure relates to an integrated surgical system configured to image and treat ocular tissue in an eye having a cornea, an iris, an anterior chamber, an irido-corneal angle, and a direction of view. The integrated surgical system includes a first optical subsystem configured to couple to the eye, a laser source configured to output a laser beam, a second optical subsystem optically coupled between the laser source and the first optical subsystem, and a control system. The first optical subsystem is configured to establish a common optical path through the cornea and the anterior chamber into the irido-corneal angle. The common optical path is offset from an optical axis within the direction of view of the eye. The second optical subsystem is configured to rotate relative to the optical axis, and includes an optical coherence tomography (OCT) imaging apparatus configured to output an OCT beam, a scanning component optically coupled with the laser source and the OCT imaging apparatus to receive each of the laser beam and the OCT beam, and focusing optics optically coupled between the scanning component and the first optical subsystem. The control system is coupled with the laser source and the second optical subsystem and is configured to affect operation of the laser source, the OCT imaging apparatus, the scanning component, and the focusing optics to: obtain a circumferential OCT image of the irido-corneal angle, obtain an azimuthal OCT image of the irido-corneal angle, and deliver optical energy through the laser beam in accordance with a treatment pattern that is based on the circumferential OCT image and the azimuthal OCT image.

The present disclosure also relates to a method of imaging and treating ocular tissue of an eye having a cornea, an iris, an anterior chamber, an irido-corneal angle, and a direction of view. The method may be performed by the just-described integrated surgical system. The method includes establishing a common optical path through the cornea and the anterior chamber into the irido-corneal angle for each of an OCT beam and a laser beam. The common optical path is offset from an optical axis within the direction of view. The method also includes obtaining a circumferential OCT image of the irido-corneal angle, obtaining an azimuthal OCT image of the irido-corneal angle, and determining a treatment pattern for a volume of ocular tissue of the irido-corneal angle based on the circumferential OCT image and the azimuthal OCT image. The method further includes delivering optical energy through the laser beam in accordance with the treatment pattern.

The circumferential OCT image may be obtained by scanning the OCT beam through a circumferential plane of the volume of ocular tissue, where the circumferential plane is bound by a first circumferential boundary, a second circumferential boundary, an anterior-chamber boundary adjacent the anterior chamber, and a sclera boundary adjacent the sclera. The OCT beam may be scanned through the circumferential plane by moving a focus of the OCT beam to each of a plurality of circumferential points between the first circumferential boundary the second circumferential boundary; and at each of the plurality of circumferential points, moving the focus of the OCT beam to each of a plurality of points between the anterior-chamber boundary and the sclera boundary. The focus of the OCT beam may be moved to each of a plurality of circumferential points by rotating an optical subsystem relative to the optical axis, to each of the plurality of circumferential points. The optical subsystem includes an OCT imaging apparatus that outputs the OCT beam, and focusing optics that move the focus of the OCT beam.

The azimuthal OCT image may be obtained by scanning the OCT beam through an azimuthal slice of a volume of ocular tissue, where the azimuthal slice is bound by an anterior-chamber boundary adjacent the anterior chamber, a sclera boundary adjacent the sclera, a corneal boundary adjacent the cornea, and an iris boundary adjacent the iris. The OCT beam may be scanned through the azimuthal slice by moving a focus of the OCT beam to each of a plurality of azimuthal points between the iris boundary and the corneal boundary; and at each of the plurality of azimuthal points, moving the focus of the OCT beam to each of a plurality of points between the anterior-chamber boundary and the sclera boundary.

A treatment pattern for the volume of ocular tissue may be determined based on the circumferential OCT image and the azimuthal OCT image by deriving a first dimension parameter (e.g., thickness) and a second dimension parameter (e.g., height) of the treatment pattern from the azimuthal OCT image; and deriving a third dimension parameter (e.g., width) of the treatment pattern from the circumferential OCT image. The treatment pattern for the volume of ocular tissue may be based on a plurality of circumferential OCT images that are processed together, e.g., averaged, to obtain a single, composite circumferential OCT images, and a plurality of azimuthal OCT images that are processed together to obtain a single, composite azimuthal OCT image.

Optical energy may be delivered through the laser beam in accordance with the treatment pattern by placing a focus of the laser beam at an initial depth in a target volume of ocular tissue bound by the first, second and third dimension parameters of the treatment pattern; and delivering optical energy sufficient to affect ocular tissue during a three-dimensional scanning of the laser beam through the treatment pattern.

The present disclosure also relates to a system for segmented imaging of ocular tissue of an eye having a cornea, an iris, an anterior chamber, an irido-corneal angle, and a direction of view. The system includes a first optical subsystem configured to couple to the eye, a second optical subsystem, and a control system. The first optical subsystem is configured to establish an optical path through the cornea and the anterior chamber into the irido-corneal angle. The optical path is offset from an optical axis within the direction of view of the eye. The second optical subsystem is configured to rotate relative to the optical axis, and includes an OCT imaging apparatus configured to output an OCT beam, a scanning component optically coupled with the OCT imaging apparatus to receive the OCT beam, and focusing optics optically coupled between the scanning component and the first optical subsystem. The control system is coupled with the second optical subsystem and is configured to affect operation of the OCT imaging apparatus, the scanning component, and the focusing optics to: direct an OCT beam along the optical path, align the OCT beam with an initial segment of ocular tissue of the irido-corneal angle, obtain a circumferential OCT image of the initial segment of ocular tissue, and repeatedly align the OCT beam and obtain a circumferential OCT image for one or more additional segments of ocular tissue.

The present disclosure also relates to a method of segmented imaging of an irido-corneal angle of an eye having a cornea, an iris, an anterior chamber, an irido-corneal angle, and a direction of view. The method may be performed by the just-described segmented imaging system. The method includes directing an OCT beam along an optical path through the cornea and the anterior chamber into the irido-corneal angle. The optical path is offset from an optical axis within the direction of view. The method also includes aligning the OCT beam with an initial segment of ocular tissue of the irido-corneal angle, obtaining a circumferential OCT image of the initial segment of ocular tissue, and repeating the aligning and obtaining for one or more additional segments of ocular tissue. For example, the aligning and obtaining may be repeated for a plurality of additional segments around all or a portion of an entire circumference of the irido-corneal angle.

The OCT beam may be aligned with the initial segment of ocular tissue or one or more additional segments of ocular tissue by rotating an optical subsystem relative to the optical axis, to a target point of the initial segment or additional segment. The optical subsystem includes an OCT imaging apparatus that outputs the OCT beam. The circumferential OCT image of the initial segment of ocular tissue or one or more additional segments of ocular tissue may be obtained by scanning the OCT beam through a circumferential plane of the initial segment or additional segment of ocular tissue. The circumferential plane may be bound by a first circumferential boundary, a second circumferential boundary, an anterior-chamber boundary adjacent the anterior chamber, and a sclera boundary adjacent the sclera.

The method may further include obtaining an azimuthal OCT image of at least one of the initial segment of ocular tissue or the one or more additional segments of ocular tissue. The azimuthal OCT image of the at least one of the initial segment of ocular tissue or the one or more additional segments of ocular tissue may be obtained by scanning the OCT beam through an azimuthal slice of the initial segment or additional segment of ocular tissue. The azimuthal slice may be bound by an anterior-chamber boundary adjacent the anterior chamber, a sclera boundary adjacent the sclera, a corneal boundary adjacent the cornea, and an iris boundary adjacent the iris.

The present disclosure also relates to a system for near-continuous imaging of ocular tissue of an eye having a cornea, an iris, an anterior chamber, an irido-corneal angle, and a direction of view. The system includes a first optical subsystem configured to couple to the eye, a second optical subsystem, and a control system. The first optical subsystem is configured to establish an optical path through the cornea and the anterior chamber into the irido-corneal angle. The optical path is offset from an optical axis within the direction of view. The second optical subsystem is configured to rotate relative to the optical axis, and includes an OCT imaging apparatus configured to output an OCT beam, a scanning component optically coupled with the OCT imaging apparatus to receive the OCT beam, and focusing optics optically coupled between the scanning component and the first optical subsystem. The control system is coupled with the second optical subsystem and is configured to affect operation of the OCT imaging apparatus, the scanning component, and the focusing optics to: direct an OCT beam along the optical path, and for each of a plurality of circumferential points along a circumferential extent of the irido-corneal angle, align the OCT beam at a circumferential point, and, while the OCT beam is at the circumferential point, obtain OCT image data for the circumferential point. The control system is further configured to construct a circumferential OCT image based on the obtained OCT image data.

The present disclosure also relates to a method for near-continuous imaging of ocular tissue of an eye having a cornea, an iris, an anterior chamber, an irido-corneal angle, and a direction of view. The method may be performed by the just-described near-continuous imaging system. The method includes directing an OCT beam along an optical path through the cornea and the anterior chamber into the irido-corneal angle. The optical path is offset from an optical axis within the direction of view. The method also includes, for each of a plurality of circumferential points along a circumferential extent of the irido-corneal angle: aligning the OCT beam at a circumferential point, and while the OCT beam is at the circumferential point, obtaining OCT image data for the circumferential point. The OCT image data for each of the circumferential points may be obtained by scanning the OCT beam between an anterior-chamber boundary adjacent the anterior chamber and a sclera boundary adjacent the sclera. The method further includes constructing a circumferential OCT image based on the obtained OCT image data.

It is understood that other aspects of methods and systems will become apparent to those skilled in the art from the following detailed description, wherein various aspects of apparatuses and methods are shown and described by way of illustration. As will be realized, these aspects may be implemented in other and different forms and its several details are capable of modification in various other respects. Accordingly, the drawings and detailed description are to be regarded as illustrative in nature and not as restrictive.

BRIEF DESCRIPTION OF THE DRAWINGS

The patent or application file contains at least one drawing executed in color. Copies of this patent or patent application publication with color drawings(s) will be provided by the Office upon request and payment of the necessary fee.

Various aspects of systems, apparatuses, and methods will now be presented in the detailed description by way of example, and not by way of limitation, with reference to the accompanying drawings, wherein:

FIGS. 9a and 9b are schematic illustrations of the focusing objective of the integrated surgical system of FIG. 7 coupled to (FIG. 9a) and decoupled from (FIG. 9b) the patient interface of the integrated surgical system of FIG. 7.

DETAILED DESCRIPTION

Figure 1:
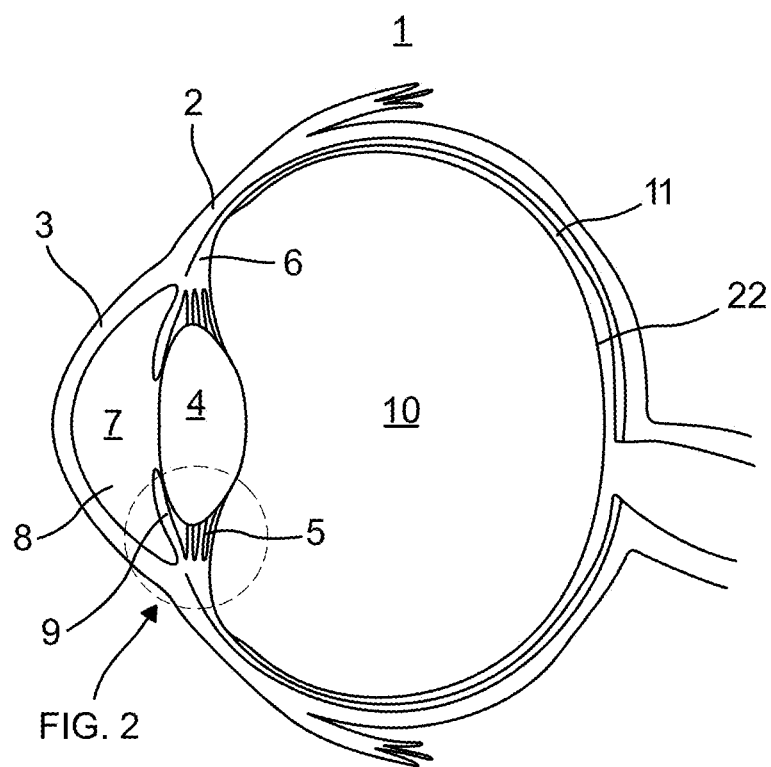
FIG. 1 is a sectional schematic illustration of a human eye and its interior anatomical structures.
Figure 2:
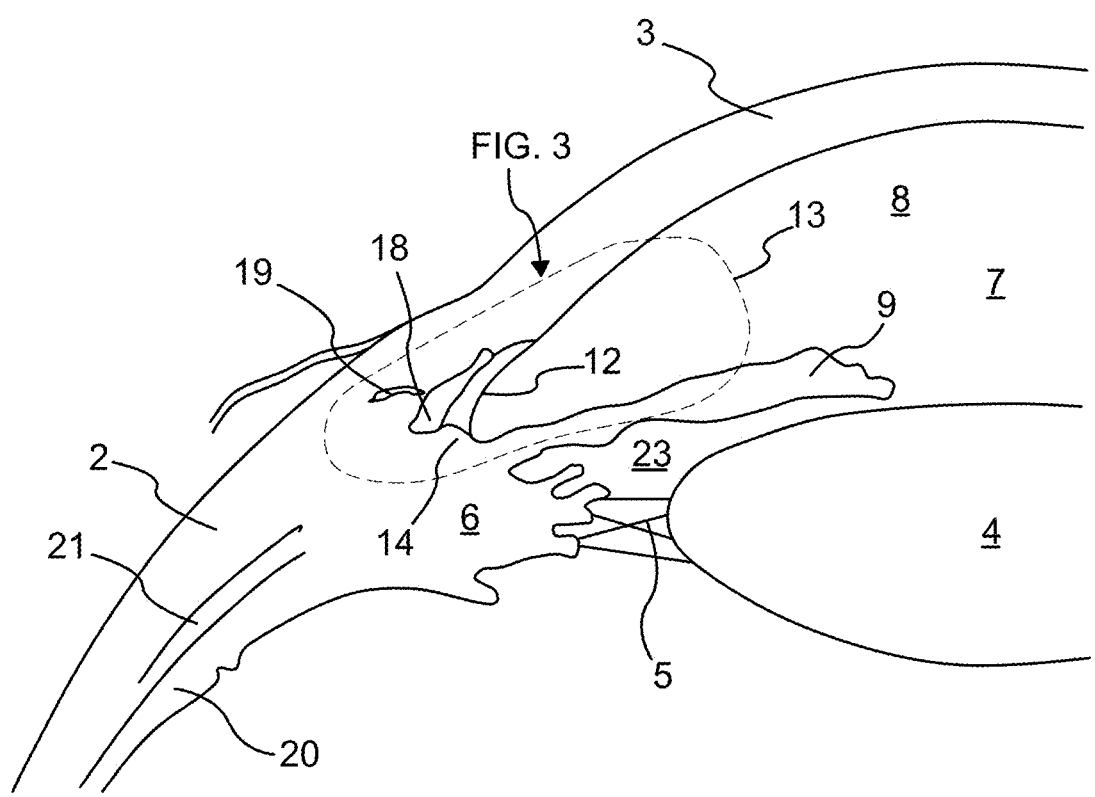
FIG. 2 is a sectional schematic illustration of the irido-corneal angle of the eye of FIG. 1.
Figure 3:
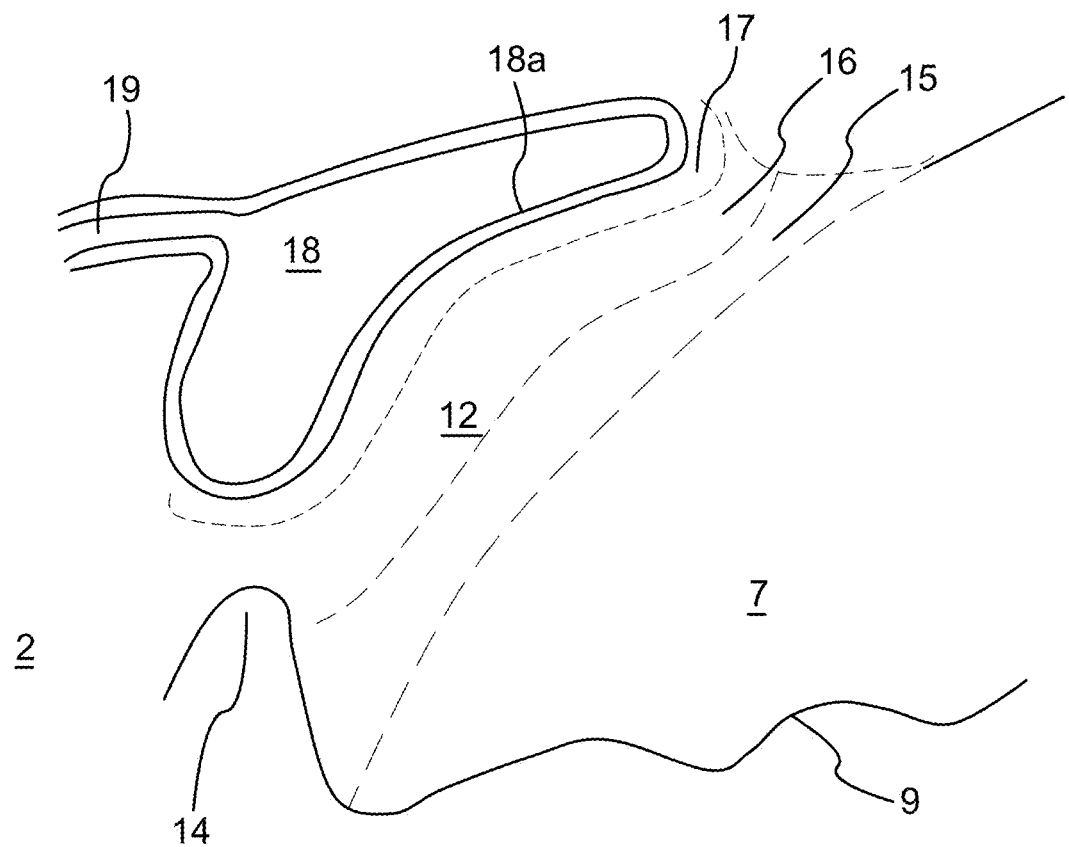
FIG. 3 is a sectional schematic illustration detailing anatomical structures in the irido-corneal angle of FIG. 2, including the trabecular meshwork, Schlemm's canal, and one or more collector channels branching from the Schlemm's canal.
Figure 4:
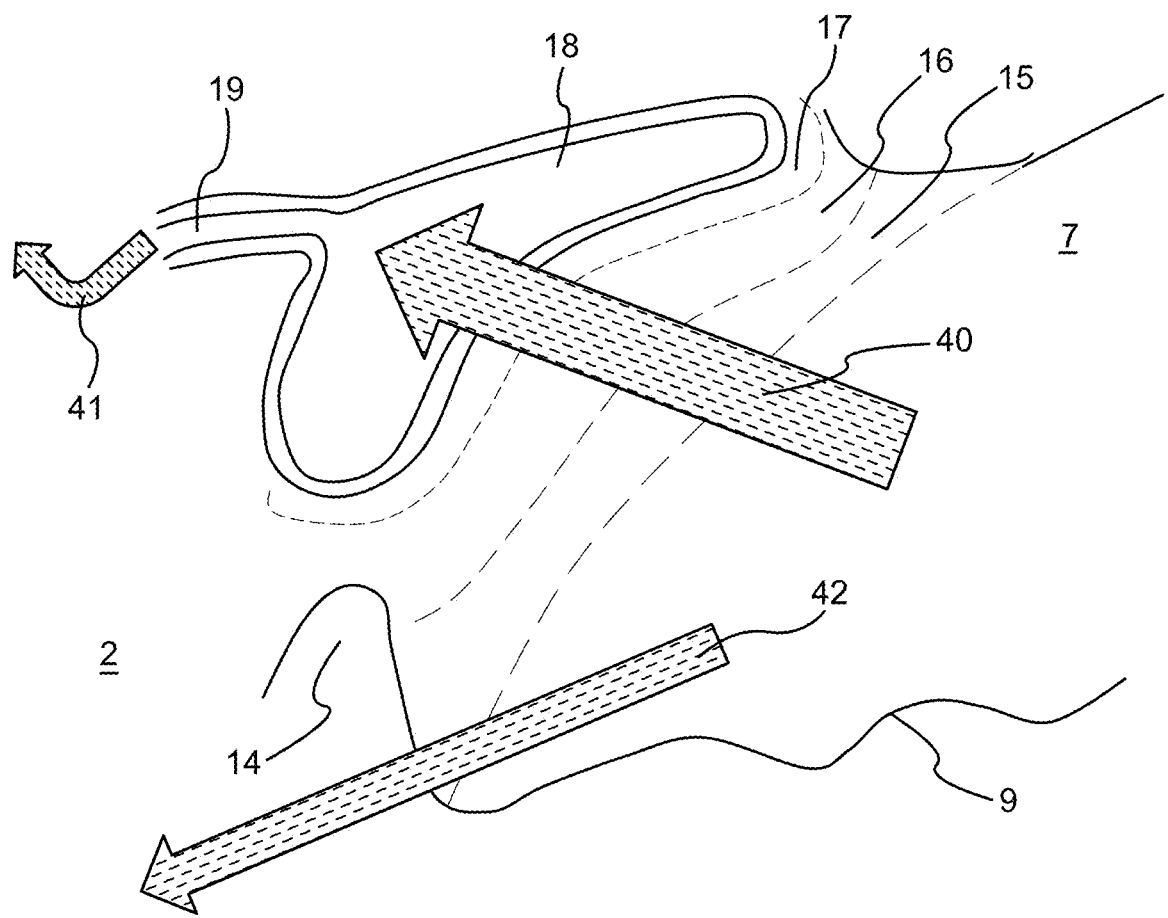
FIG. 4 is a sectional schematic illustration of various outflow pathways for aqueous humor through the trabecular meshwork, Schlemm's canal, and collector channels of FIG. 3.
Figure 5:
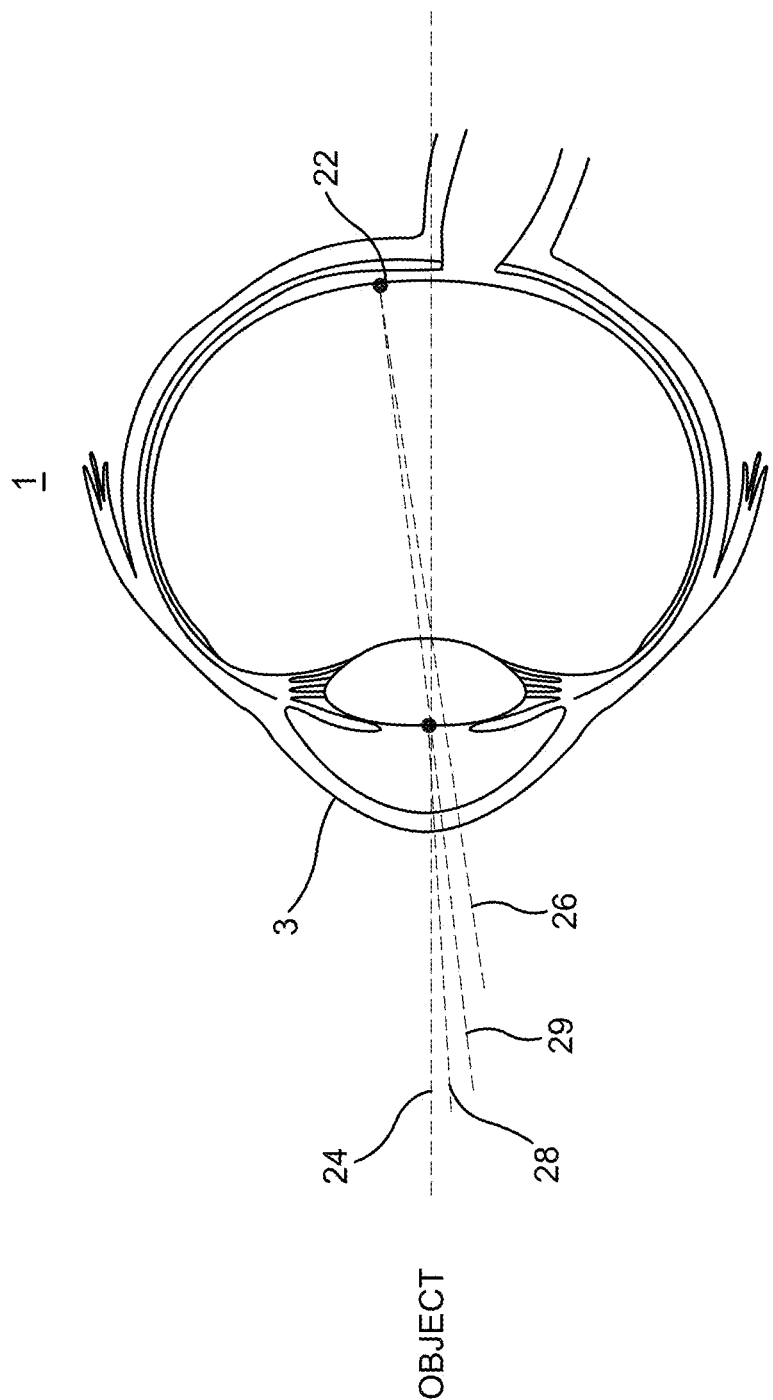
FIG. 5 is a sectional schematic illustration of a human eye showing various axes associated with the eye.

Disclosed herein are systems and methods for safely and effectively reducing intra-ocular pressure (IOP) in the eye to either treat or reduce the risk of glaucoma. The systems and methods enable imaging and surgical scanning of all or a portion of the anterior chamber angle, i.e., the irido-corneal angle, of the eye to treat abnormal ocular tissue conditions within the irido-corneal angle. The systems and methods enable visualization of structures of the irido-corneal angle relevant to laser treatment for glaucoma, including the trabecular meshwork, Schlemm's canal, and the collector channels. To this end, the systems and method may obtain OCT images from different perspectives, including a circumferential perspective and an azimuthal perspective. In one embodiment, the systems and methods enable full 360-degree circumferential imaging of the irido-corneal angle.

An integrated surgical system disclosed herein is configured to image and treat ocular tissue in an eye having a cornea, an iris, an anterior chamber, an irido-corneal angle, and a direction of view. The integrated surgical system includes a first optical subsystem that couples to the eye, a laser source configured to output a laser beam, a second optical subsystem optically coupled between the laser source and the first optical subsystem, and a control system. The first optical subsystem is configured to establish a common optical path through the cornea and the anterior chamber into the irido-corneal angle. The common optical path is offset from an optical axis within the direction of view of the eye. The second optical subsystem is configured to rotate relative to the optical axis, and includes an optical coherence tomography (OCT) imaging apparatus configured to output an OCT beam, a scanning component optically coupled with the laser source and the OCT imaging apparatus to receive each of the laser beam and the OCT beam, and focusing optics optically coupled between the scanning component and the first optical subsystem. The control system is coupled with the laser source and the second optical subsystem and is configured to affect operation of the laser source, the OCT imaging apparatus, the scanning component, and the focusing optics to obtain a circumferential OCT image of the irido-corneal angle, obtain an azimuthal OCT image of the irido-corneal angle, and deliver optical energy through the laser beam in accordance with a treatment pattern that is based on the circumferential OCT image and the azimuthal OCT image.

The laser source may be a femtosecond laser, or a picosecond laser. Such lasers provide non-thermal photo-disruption interaction with ocular tissue to avoid thermal damage to surrounding tissue. Further, unlike other surgical methods, with femtosecond laser treatment opening surface incisions penetrating the eye can be avoided, enabling a non-invasive treatment. Instead of performing the treatment in a sterile surgical room, the non-invasive treatment can be performed in a non-sterile outpatient facility.

One or more additional imaging components may be included in the integrated surgical system to provide direct visual observation of the irido-corneal angle along an angle of visual observation. For example, a microscope or imaging camera may be included to assist the surgeon in the process of docking the eye to the patient interface or an immobilizing device, location of ocular tissues in the eye and observing the progress of the surgery. The angle of visual observation can also be along the angled beam path 30 to the irido-corneal angle 13 through the cornea 3 and the anterior chamber 7. In another example, a dual-aiming beam apparatus may be included to assist the surgeon in locating surfaces of tissue during laser treatment.

OCT Imaging

OCT imaging may be used to determine the structural and geometrical conditions of the anterior chamber 7, to assess possible obstruction of the trabecular outflow pathway 40 and to determine the accessibility of the ocular tissue for treatment. As previously described, the iris 9 in a collapsed anterior chamber 7 may obstruct and close off the flow of aqueous humor 8, resulting in closed-angle glaucoma. In open-angle glaucoma, where the macroscopic geometry of the angle is normal, the permeability of ocular tissue may be affected, by blockage of tissue along the trabecular outflow pathway 40 or by the collapse of the Schlemm's canal 18 or collector channels 19.

OCT imaging can provide the spatial resolution, tissue penetration and contrast to resolve microscopic details of ocular tissue. As disclosed herein, an OCT imaging beam may be scanned in multiple directions in the irido-corneal angle 13 to provide two-dimensional (2D) images of the ocular tissue from different perspectives. These multiple directions include a direction generally perpendicular to the trabecular meshwork, referred to herein as the "azimuthal" direction, and a direction generally parallel to the trabecular meshwork, referred to herein as the "circumferential" direction. More specifically, the azimuthal direction is directed across the height of the trabecular meshwork 12 from the scleral spur 14 to the cornea 3. The circumferential direction is along an arc that sweeps the perimeter of the irido-corneal angle 13 parallel to the trabecular meshwork 12. OCT images resulting from scanning in the azimuthal direction are referred to as azimuthal OCT images. OCT images resulting from scanning in the circumferential direction are referred to as circumferential OCT images. The circumferential and azimuthal OCT images may be processed and analyzed to determine the size, shape, and location of structures in the eye for surgical targeting, and to determine a treatment pattern for laser surgery.

Femtosecond Laser Source

The preferred surgical component of the integrated surgical system disclosed herein is a femtosecond laser. A femtosecond laser provides highly localized, non-thermal photo-disruptive laser-tissue interaction with minimal collateral damage to surrounding ocular tissue. Photo-disruptive interaction of the laser is utilized in optically transparent tissue. The principal mechanism of laser energy deposition into the ocular tissue is not by absorption but by a highly nonlinear multiphoton process. This process is effective only at the focus of the pulsed laser where the peak intensity is high. Regions where the beam is traversed but not at the focus are not affected by the laser. Therefore, the interaction region with the ocular tissue is highly localized both transversally and axially along the laser beam. The process can also be used in weakly absorbing or weakly scattering tissue. While femtosecond lasers with photo-disruptive interactions have been successfully used in ophthalmic surgical systems and commercialized in other ophthalmic laser procedures, none have been used in an integrated surgical system that accesses the irido-corneal angle.

In known refractive procedures, femtosecond lasers are used to create corneal flaps, pockets, tunnels, arcuate incisions, lenticule shaped incisions, partial or fully penetrating corneal incisions for keratoplasty. For cataract procedures the laser creates a circular cut on the capsular bag of the eye for capsulotomy and incisions of various patterns in the lens for braking up the interior of the crystalline lens to smaller fragments to facilitate extraction. Entry incisions through the cornea opens the eye for access with manual surgical devices and for insertions of phacoemulsification devices and intra-ocular lens insertion devices. Several companies have commercialized such surgical systems, among them the IntraLase system now available from Johnson & Johnson Vision, Santa Ana, CA, The LenSx and WaveLight systems from Alcon, Fort Worth, TX, other surgical systems from Bausch and Lomb, Rochester, NY, Carl Zeiss Meditec AG, Germany, Ziemer, Port, Switzerland, and LENSAR, Orlando, FL.

These existing systems are developed for their specific applications, for surgery in the cornea, and the crystalline lens and its capsular bag and are not capable of performing surgery in the irido-corneal angle 13 for several reasons. First, the irido-corneal angle 13 is not accessible with these surgical laser systems because the irido-corneal angle is too far out in the periphery and is outside of surgical range of these systems. Second, the angle of the laser beam from these systems, which is along the optical axis to the eye 24, is not appropriate to reaching the irido-corneal angle 13, where there is significant scattering and optical distortion at the applied wavelength. Third, any imaging capabilities these systems may have do not have the accessibility, penetration depth and resolution to image the tissue along the trabecular outflow pathway 40 with sufficient detail and contrast.

Clear access to the irido-corneal angle 13 is provided along the angled beam path 30. The tissue, e.g., cornea 3 and the aqueous humor 8 in the anterior chamber 7, along this angled beam path 30 is transparent for wavelengths from approximately 400 nm to 2500 nm and femtosecond lasers operating in this region can be used. Such mode locked lasers work at their fundamental wavelength with Titanium, Neodymium or Ytterbium active material. Non-linear frequency conversion techniques known in the art, frequency doubling, tripling, sum and difference frequency mixing techniques, optical parametric conversion can convert the fundamental wavelength of these lasers to practically any wavelength in the above mentioned transparent wavelength range of the cornea.

Existing ophthalmic surgical systems apply lasers with pulse durations longer than 1 ns have higher photo-disruption threshold energy, require higher pulse energy and the dimension of the photo-disruptive interaction region is larger, resulting in loss of precision of the surgical treatment. When treating the irido-corneal angle 13, however, higher surgical precision is required. To this end, the integrated surgical system may be configured to apply lasers with pulse durations from 10 femtosecond (fs) to 1 nanosecond (ns) for generating photo-disruptive interaction of the laser beam with ocular tissue in the irido-corneal angle 13. While lasers with pulse durations shorter than 10 fs are available, such laser sources are more complex and more expensive. Lasers with the described desirable characteristics, e.g., pulse durations from 10 femtosecond (fs) to 1 nanosecond (ns), are commercially available from multiple vendors, such as Newport, Irvine, CA, Coherent, Santa Clara, CA, Amplitude Systems, Pessac, France, NKT Photonics, Birkerod, Denmark, and other vendors.

Accessing the Irido-Corneal Angle

Figure 6:
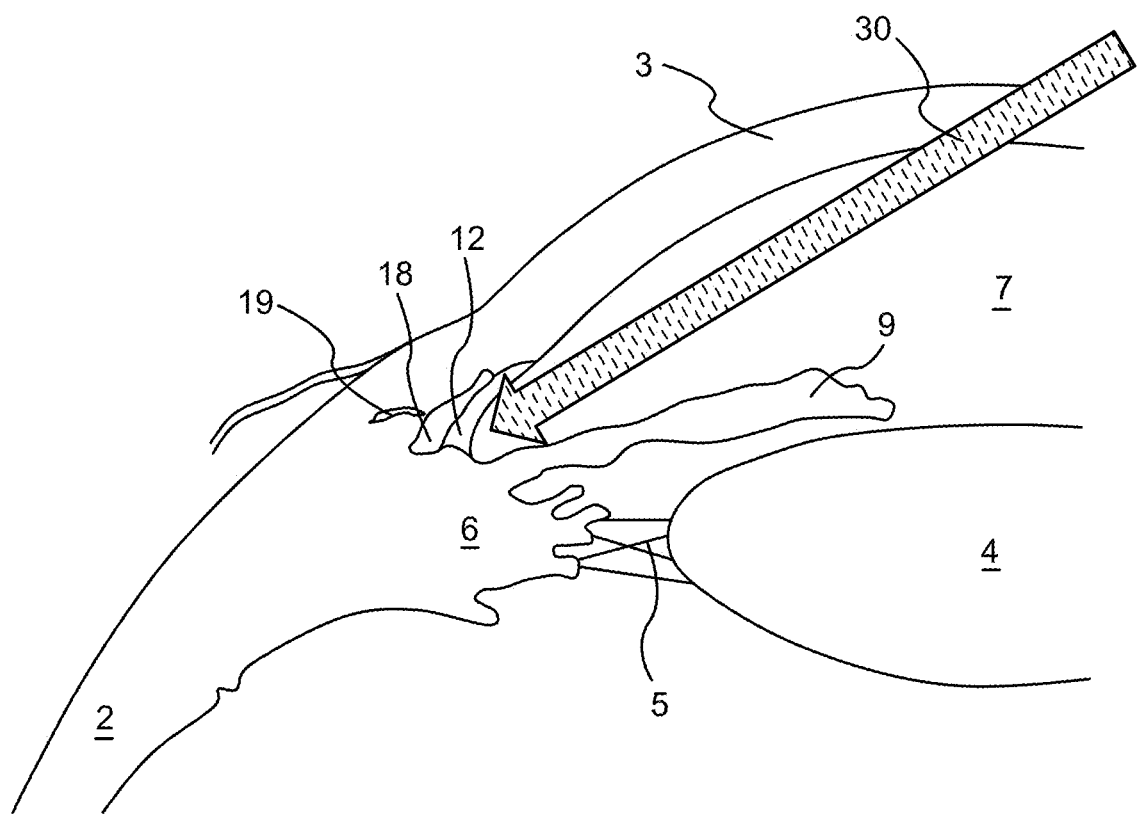
FIG. 6 is a sectional schematic illustration of an angled beam path along which one or more light beams may access the irido-corneal angle of the eye.

An important feature afforded by the integrated surgical system is access to the targeted ocular tissue in the irido-corneal angle 13. With reference to FIG. 6, the irido-corneal angle 13 of the eye may be accessed via the integrated surgical system along an angled beam path 30 passing through the cornea 3 and through the aqueous humor 8 in the anterior chamber 7. For example, one or more of an imaging beam, e.g., an OCT beam and/or a visual observation beam, and a laser beam may access the irido-corneal angle 13 of the eye along the angled beam path 30.

An optical system disclosed herein is configured to direct a light beam to an irido-corneal angle 13 of an eye along an angled beam path 30. The optical system includes a first optical subsystem and a second optical subsystem. The first optical subsystem includes a window formed of a material with a refractive index $n_w$ and has opposed concave and convex surfaces. The first optical subsystem also includes an exit lens formed of a material having a refractive index $n_x$. The exit lens also has opposed concave and convex surfaces. The concave surface of the exit lens is configured to couple to the convex surface of the window to define a first optical axis extending through the window and the exit lens. The concave surface of the window is configured to detachably couple to a cornea of the eye with a refractive index $n_c$ such that, when coupled to the eye, the first optical axis is generally aligned with the direction of view of the eye.

The second optical subsystem is configured to output a light beam, e.g., an OCT beam or a laser beam. The optical system is configured so that the light beam is directed to be incident at the convex surface of the exit lens along a second optical axis at an angle α that is offset from the first optical axis. The respective geometries and respective refractive indices $n_x$, and $n_w$ of the exit lens and window are configured to compensate for refraction and distortion of the light beam by bending the light beam so that it is directed through the cornea 3 of the eye toward the irido-corneal angle 13. More specifically, the first optical system bends the light beam to that the light beam exits the first optical subsystem and enters the cornea 3 at an appropriate angle so that the light beam progresses through the cornea and the aqueous humor 8 in a direction along the angled beam path 30 toward the irido-corneal angle 13.

Accessing the irido-corneal angle 13 along the angled beam path 30 provides several advantages. An advantage of this angled beam path 30 to the irido-corneal angle 13 is that the OCT beam and laser beam passes through mostly clear tissue, e.g., the cornea 3 and the aqueous humor 8 in the anterior chamber 7. Thus, scattering of these beams by tissue is not significant. With respect to OCT imaging, this enables the use of shorter wavelength, less than approximately 1 micrometer, for the OCT to achieve higher spatial resolution. An additional advantage of the angled beam path 30 to the irido-corneal angle 13 through the cornea 3 and the anterior chamber 7 is the avoidance of direct laser beam or OCT beam light illuminating the retina 11. As a result, higher average power laser light and OCT light can be used for imaging and surgery, resulting in faster procedures and less tissue movement during the procedure.

Another important feature provided by the integrated surgical system is access to the targeted ocular tissue in the irido-corneal angle 13 in a way that reduces beam discontinuity. To this end, the window and exit lens components of the first optical subsystem are configured to reduce the discontinuity of the optical refractive index between the cornea 3 and the neighboring material and facilitate entering light through the cornea at a steep angle.

Having thus generally described the integrated surgical system and some of its features and advantages, a more detailed description of the system and its component parts follows.

Integrated Surgical System

Figure 7:
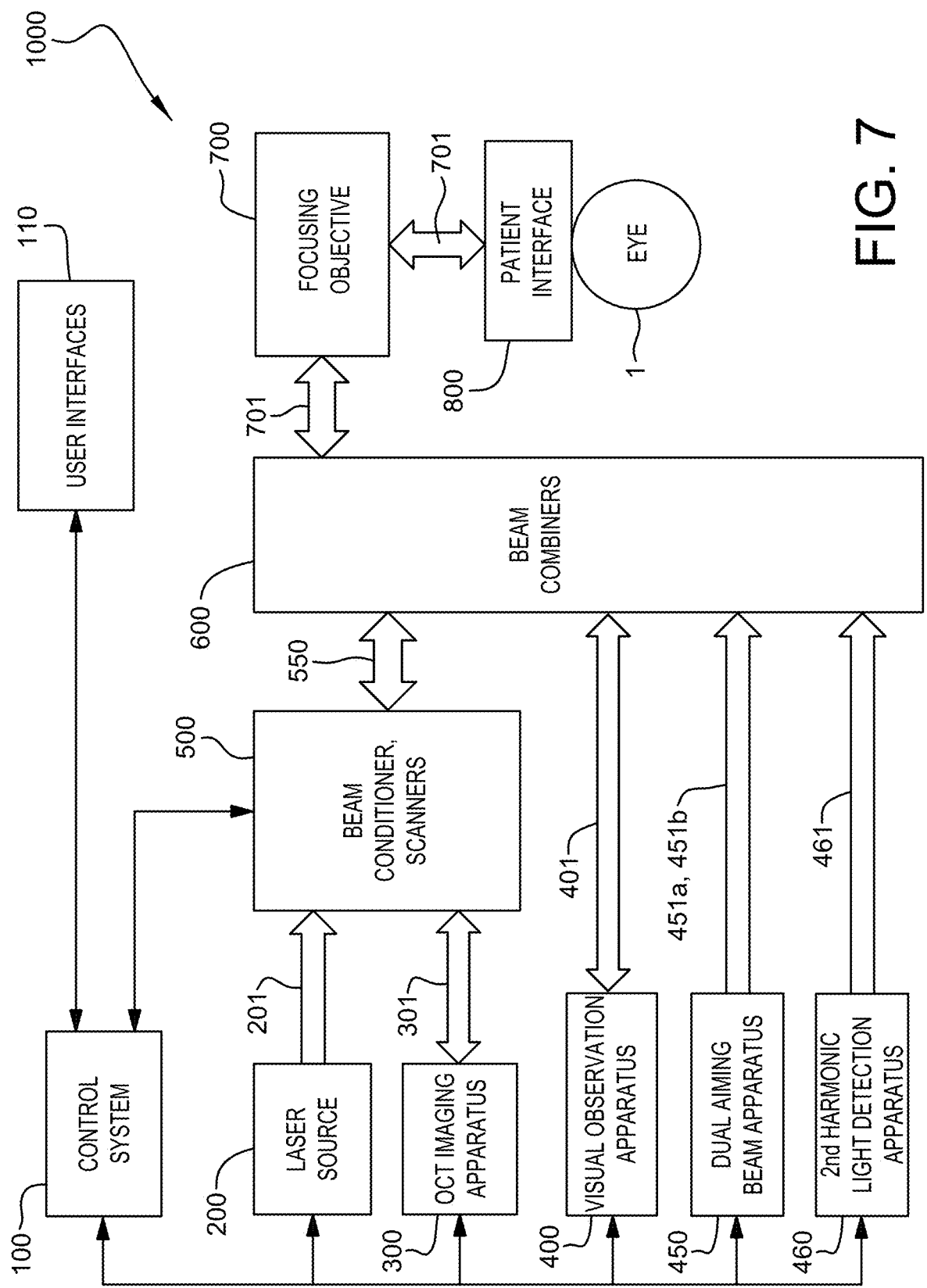
FIG. 7 is a block diagram of an integrated surgical system for non-invasive glaucoma surgery including a control system, a femtosecond laser source, an OCT imaging apparatus, a visual observation apparatus, a dual aiming beam apparatus, a second harmonic light detection apparatus, beam conditioners and scanners, beam combiners, a focusing objective, and a patient interface.

With reference to FIG. 7, an integrated surgical system 1000 for non-invasive glaucoma surgery includes a control system 100, a surgical component 200, a first imaging apparatus 300, a second imaging apparatus 400, a dual aiming beam apparatus 450, and a second harmonic light detection apparatus 460. In the embodiment of FIG. 7, the surgical component 200 is a femtosecond laser source, the first imaging apparatus 300 is an OCT imaging apparatus, and the second imaging apparatus 400 is a visual observation apparatus, comprising a video camera and an illumination source for viewing or capturing images of a surgical field. The dual aiming beam apparatus 450 outputs a pair of beams of light, referred to herein as aiming beams, for use in detecting a surface of ocular tissue in the surgical field. The second harmonic light detection apparatus 460 may be, for example, a photodetector configured to detect second harmonic light generated in the surgical field or a video camera instrumented with a visible filter centered near or at 515 nm (with a bandpass of 20-50 nm) that detects green light generated by surface second harmonic generation. The second harmonic light detection apparatus 460 facilitates locating a focus of a femtosecond laser beam 201 at or near a target structure of ocular tissue. Other components of the integrated surgical system 1000 include beam conditioners and scanners 500, beam combiners 600, a focusing objective 700, and a patient interface 800.

The control system 100 may be a single computer or a plurality of interconnected computers configured to control the hardware and software components of the other components of the integrated surgical system 1000. A user interface 110 of the control system 100 accepts instructions from a user and displays information for observation by the user. Input information and commands from the user include but are not limited to system commands, motion controls for docking the patient's eye to the system, selection of pre-programmed or live generated surgical plans or treatment patterns, navigating through menu choices, setting of surgical parameters, responses to system messages, determining and acceptance of surgical plans and commands to execute the surgical plan. Outputs from the system towards the user includes but are not limited to display of system parameters and messages, display of images of the eye, graphical, numerical, and textual display of the surgical plan and the progress of the surgery.

The control system 100 is connected to the other components 200, 300, 400, 450, 460, 500 of the integrated surgical system 1000. Signals between the control system 100 and the femtosecond laser source 200 function to control internal and external operation parameters of the laser source, including for example, power, repetition rate and beam shutter. Control and feedback signals between the control system 100 and the OCT imaging apparatus 300 function to control OCT beam scanning parameters, and the acquiring, analyzing, and displaying of OCT images. Control signals between the control system 100 and the dual aiming beam apparatus 450 function to control the output of beams of light by the one or more aiming beam sources of the dual aiming beam apparatus. Control signals between the control system 100 and the visual observation apparatus 400 function to control the capturing, image processing and displaying of spots of light on tissue surfaces in the surgical field that result from the one or more beams of light output by the dual aiming beam apparatus 450. To this end, the line of sight of the visual observation apparatus 400 is aligned with the femtosecond laser and directed into the irido-corneal angle of the eye. Signals between the control system 100 and the second harmonic light detection apparatus 460 function to control the operation of the second harmonic light detection apparatus, and the detecting of second harmonic light generated by an encounter between the focus of the laser and tissue in the irido-corneal angle of the eye. To this end, the line of sight of the second harmonic light detection apparatus 460 is aligned with the femtosecond laser and directed into the irido-corneal angle of the eye. Control signals from the control system 100 to the beam conditioner and scanners 500 function to control the focus of the laser beam output by the femtosecond laser source 200. Such control may include advancing the focus of the laser beam in the direction of propagation of the laser or in the direction opposite the direction of propagation of the laser, and scanning the focus.

Laser beams 201 from the femtosecond laser source 200 and OCT beams 301 from the OCT imaging apparatus 300 are directed towards a unit of beam conditioners and scanners 500. Different kind of scanners can be used for the purpose of scanning the laser beam 201 and the OCT beam 301. For scanning transversal to a beam 201, 301, angular scanning galvanometer scanners are available for example from Cambridge Technology, Bedford, MA, Scanlab, Munich, Germany. To optimize scanning speed, the scanner mirrors are typically sized to the smallest size, which still support the required scanning angles and numerical apertures of the beams at the target locations. The ideal beam size at the scanners is typically different from the beam size of the laser beam 201 or the OCT beam 301, and different from what is needed at the entrance of a focusing objective 700. Therefore, beam conditioners are applied before, after, or in between individual scanners. The beam conditioner and scanners 500 includes scanners for scanning the beam transversally and axially. Axial scanning changes the depth of the focus at the target region. Axial scanning can be performed by moving a lens axially in the beam path with a servo or stepper motor.

The laser beam 201 and the OCT beam 301 are combined with dichroic, polarization or other kind of beam combiners 600 to reach a common target volume or surgical volume in the eye. Likewise, an illumination beam 401 from the visual observation apparatus 400 and a pair of aiming beams of light 451a, 451b from the dual aiming beam apparatus 450 are combined by dichroic, polarization or other kind of beam combiners 600 to reach the common target volume or surgical volume in the eye. In an integrated surgical system 1000 having a femtosecond laser source 200, an OCT imaging apparatus 300, a visual observation apparatus 400, and a dual aiming beam apparatus 450, the individual beams 201, 301, 401, 451a, 451b for each of these components may be individually optimized and may be collinear or non-collinear to one another. The beam combiner 600 uses dichroic or polarization beam splitters to split and recombine light with different wavelength and/or polarization. The beam combiner 600 may also include optics to change certain parameters of the individual beams 201, 301, 401, 451a, 451b such as beam size, beam angle and divergence. Integrated visual illumination, observation or imaging devices assist the surgeon in docking the eye to the system and identifying surgical locations. For example, details on locating a surface of tissue using a dual aiming beam apparatus 450 are provided in U.S. patent application Ser. No. 16/781,770, titled "System and Method for Locating a Surface of Ocular Tissue for Glaucoma Surgery Based on Dual Aiming Beams," which is hereby incorporated by reference.

To facilitate locating a focus of a femtosecond laser beam 201 at or near a target structure of ocular tissue, the second harmonic light detection apparatus 460 of the integrated surgical system 1000 generates information indicative of the presence or absence of second harmonic light in the iridocorneal angle of the eye. To this end, in one embodiment, the second harmonic light detection apparatus 460 is configured to detect for a second harmonic light beam 451 using a photodetector, and to provide an intensity profile of second harmonic generated light as a function of scan depth of the second harmonic signal as the focus of the femtosecond laser beam 201 is advanced. Details on the second harmonic light detection apparatus 460 are provided in U.S. patent application Ser. No. 16/723,883, titled "System and Method for Locating a Structure of Ocular Tissue for Glaucoma Surgery Based on Second Harmonic Light," which is hereby incorporated by reference.

To resolve ocular tissue structures of the eye in sufficient detail, the OCT imaging apparatus 300 of the integrated surgical system 1000 may provide an OCT beam having a spatial resolution of several micrometers. The resolution of the OCT beam is the spatial dimension of the smallest feature that can be recognized in the OCT image. It is determined mostly by the wavelength and the spectral bandwidth of the OCT source, the quality of the optics delivering the OCT beam to the target location in the eye, the numerical aperture of the OCT beam and the spatial resolution of the OCT imaging apparatus 300 at the target location. In one embodiment, the OCT beam of the integrated surgical system has a resolution of no more than 5 μm.

Likewise, the surgical laser beam provided by the femtosecond laser source 200 may be delivered to targeted locations with several micrometer accuracy. The resolution of the laser beam is the spatial dimension of the smallest feature at the target location that can be modified by the laser beam without significantly affecting surrounding ocular tissue. It is determined mostly by the wavelength of the laser beam, the quality of the optics delivering the laser beam to target location in the eye, the numerical aperture of the laser beam, the energy of the laser pulses in the laser beam and the spatial resolution of the laser scanning system at the target location. In addition, to minimize the threshold energy of the laser for photo-disruptive interaction, the size of the laser spot should be no more than approximately 5 μm.

For practical embodiments, beam conditioning, scanning and combining the optical paths are certain functions performed on the laser beam 201, the OCT beam 301, the illumination beam 401, and the aiming beams of light 451a, 451b. Implementation of those functions may happen in a different order than what is indicated in FIG. 7. Specific optical hardware that manipulates the beams to implement those functions can have multiple arrangements with regards to how the optical hardware is arranged. They can be arranged in a way that they manipulate individual optical beams separately, in another embodiment one component may combine functions and manipulates different beams. For example, a single set of scanners can scan both the laser beam 201 and the OCT beam 301. In this case, separate beam conditioners set the beam parameters for the laser beam 201 and the OCT beam 301, then a beam combiner combines the two beams for a single set of scanners to scan the beams. While many combinations of optical hardware arrangements are possible for the integrated surgical system, the following section describes in detail an example arrangement.

Beam Delivery

In the following description, the term beam may—depending on the context—refer to one of a laser beam, an OCT beam, an illumination beam, or one or more aiming beams. A combined beam refers to two or more of a laser beam, an OCT beam, an illumination beam, or an aiming beam that are either collinearly combined or non-collinearly combined. Example combined beams include a combined OCT/laser beam, which is a collinear or non-colinear combination of an OCT beam and a laser beam, and a combined OCT/laser/illumination beam, which is a collinear or non-collinear combination of an OCT beam, a laser beam, and an illumination beam, and a combined OCT/laser/illumination/aiming beam, which is a collinear or non-collinear combination of an OCT beam, a laser beam, an illumination beam, and one or more aiming beams. In a collinearly combined beam, the different beams may be combined by dichroic or polarization beam splitters, and delivered along a same optical path through a multiplexed delivery of the different beams. In a non-collinear combined beam, the different beams are delivered at the same time along different optical paths that are separated spatially or by an angle between them.

In the description to follow, any of the foregoing beams or combined beams may be generically referred to as a light beam. The terms distal and proximal may be used to designate the direction of travel of a beam, or the physical location of components relative to each other within the integrated surgical system. The distal direction refers to a direction toward the eye; thus an OCT beam output by the OCT imaging apparatus moves in the distal direction toward the eye. The proximal direction refers to a direction away from the eye; thus an OCT return beam from the eye moves in the proximal direction toward the OCT imaging apparatus.

Figure 8:
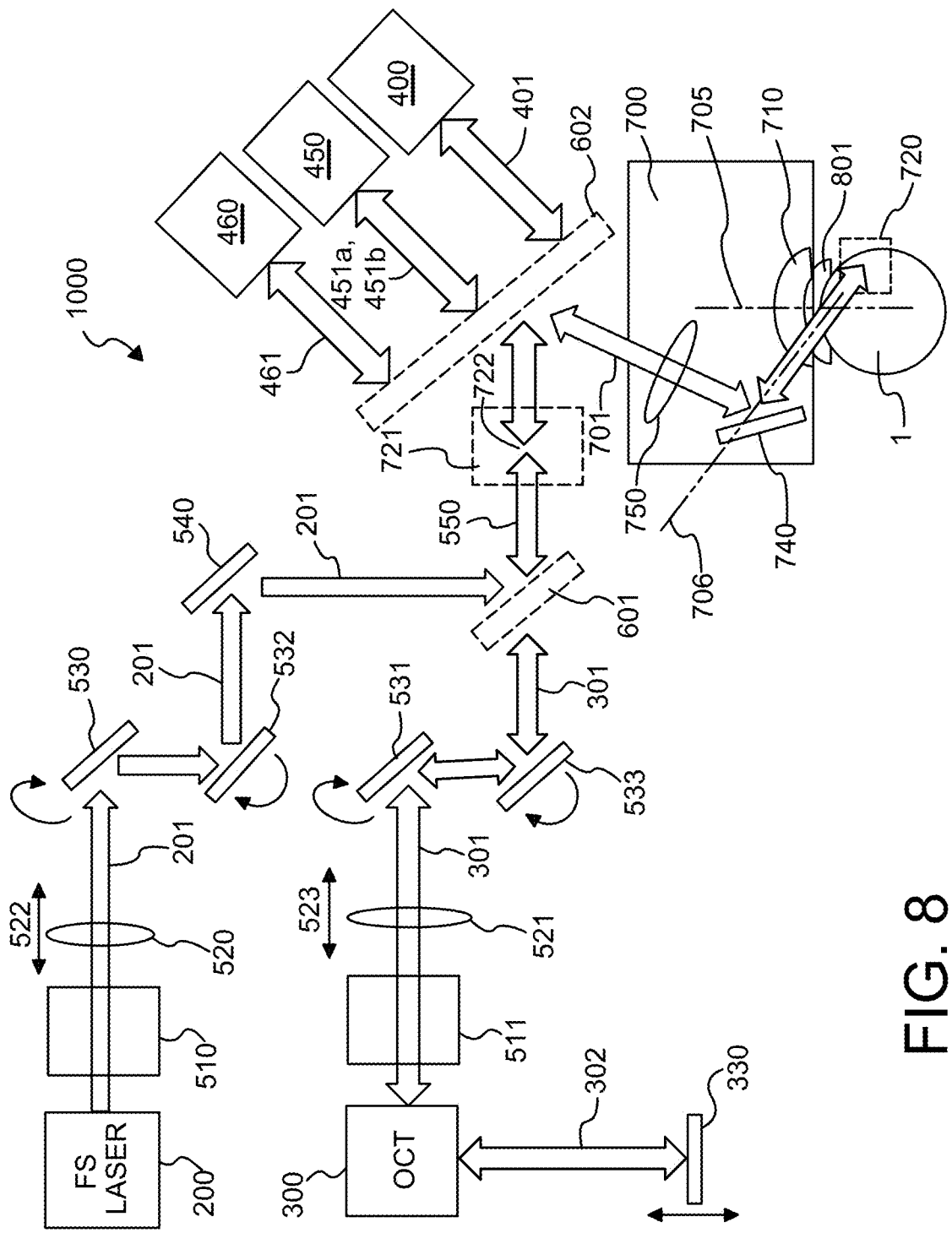
FIG. 8 is a detailed block diagram of the integrated surgical system of FIG. 7.

Referring to FIG. 8, in one embodiment, an integrated surgical system is configured to deliver each of a laser beam 201, an illumination beam 401, and a pair of aiming beams of light 451a, 451b in the distal direction toward an eye 1, and receive an illumination return beam 401 back from the eye 1. In another embodiment, an integrated surgical system is configured to deliver each of a laser beam 201, an OCT beam 301, an illumination beam 401, and a pair of aiming beams of light 451a, 451b in the distal direction toward an eye 1, and receive each of an OCT return beam 301 and an illumination return beam 401 back from the eye 1.

In another embodiment, an integrated surgical system is configured to deliver each of a laser beam 201 and an illumination beam 401 in the distal direction toward an eye 1, and receive an illumination return beam 401 and a second harmonic light beam 461 back from the eye 1. In another embodiment, an integrated surgical system is configured to deliver each of a laser beam 201, an OCT beam 301, and an illumination beam 401 in the distal direction toward an eye, and receive each of an OCT return beam 301, an illumination return beam 401, and a second harmonic light beam 461 back from the eye.

In another embodiment, an integrated surgical system is configured to deliver each of a laser beam 201, an illumination beam 401, a pair of aiming beams of light 451a, 451b, in the distal direction toward an eye 1, and receive an illumination return beam 401 and a second harmonic light beam 461 back from the eye 1. In another embodiment, an integrated surgical system is configured to deliver each of a laser beam 201, an OCT beam 301, an illumination beam 401, and a pair of aiming beams of light 451a, 451b in the distal direction toward an eye 1, and receive each of an OCT return beam 301, an illumination return beam 401 and a second harmonic light beam 461 back from the eye 1.

Regarding the delivery of a laser beam, a laser beam 201 output by the femtosecond laser source 200 passes through a beam conditioner 510 where the basic beam parameters, beam size, divergence are set. The beam conditioner 510 may also include additional functions, setting the beam power or pulse energy and shutter the beam to turn it on or off. After existing the beam conditioner 510, the laser beam 210 enters an axial scanning lens 520. The axial scanning lens 520, which may include a single lens or a group of lenses, is movable in the axial direction 522 by a servo motor, stepper motor or other control mechanism. Movement of the axial scanning lens 520 in the axial direction 522 changes the axial distance of the focus of the laser beam 210 at a focal point.

In a particular embodiment of the integrated surgical system, an intermediate focal point 722 is set to fall within, and is scannable in, the conjugate surgical volume 721, which is an image conjugate of the surgical volume 720, determined by the focusing objective 700. The surgical volume 720 is the spatial extent of the region of interest within the eye where imaging and surgery is performed. For glaucoma surgery, the surgical volume 720 is the vicinity of the irido-corneal angle 13 of the eye.

A pair of transverse scanning mirrors 530, 532 rotated by a galvanometer scanner scan the laser beam 201 in two essentially orthogonal transversal directions, e.g., in the x and y directions. Then the laser beam 201 is directed towards a dichroic or polarization beam splitter 540 where it is reflected toward a beam combining mirror 601 configured to combine the laser beam 201 with an OCT beam 301.

Regarding delivery of an OCT beam, an OCT beam 301 output by the OCT imaging apparatus 300 passes through a beam conditioner 511, an axially moveable focusing lens 521 and a transversal scanner with scanning mirrors 531 and 533. The focusing lens 521 is used set the focal position of the OCT beam in the conjugate surgical volume 721 and the real surgical volume 720. The focusing lens 521 is not scanned for obtaining an OCT axial scan. Axial spatial information of the OCT image is obtained by Fourier transforming the spectrum of the interferometrically recombined OCT return beam 301 and reference beams 302. However, the focusing lens 521 can be used to re-adjust the focus when the surgical volume 720 is divided into several axial segments. This way the optimal imaging spatial resolution of the OCT image can be extended beyond the Rayleigh range of the OCT signal beam, at the expense of time spent on scanning at multiple ranges.

Proceeding in the distal direction toward the eye 1, after the scanning mirrors 531 and 533, the OCT beam 301 is combined with the laser beam 201 by the beam combiner mirror 601. The OCT beam 301 and laser beam 201 components of the combined laser/OCT beam 550 are multiplexed and travel in the same direction to be focused at an intermediate focal point 722 within the conjugate surgical volume 721. After having been focused in the conjugate surgical volume 721, the combined laser/OCT beam 550 propagates to a second beam combining mirror 602 where it is combined with illumination beam 401 to form a combined laser/OCT/illumination beam 701. Regarding delivery of the illumination beam 401 and the pair of aiming beams of light 451a, 451b, details of the delivery of these beams is described in U.S. patent application Ser. No. 16/781,770, titled "System and Method for Locating a Surface of Ocular Tissue for Glaucoma Surgery Based on Dual Aiming Beams."

The combined laser/OCT/illumination/aiming beam 701 traveling in the distal direction then passes through a relay lens 750 included in the focusing objective 700, is reflected by a reflecting surface 740, which may be a planar beam-folding mirror or a facet inside an optic, and then passes through an exit lens 710 and a window 801 of a patient interface, where the intermediate focal point 722 of the laser beam within the conjugate surgical volume 721 is re-imaged into a focal point in the surgical volume 720. The focusing objective 700 re-images the intermediate focal point 722, through the window 801 of a patient interface, into the ocular tissue within the surgical volume 720.

A scattered OCT return beam 301 from the ocular tissue travels in the proximal direction to return to the OCT imaging apparatus 300 along the same paths just described, in reverse order. The reference beam 302 of the OCT imaging apparatus 300, passes through a reference delay optical path and return to the OCT imaging apparatus from a moveable mirror 330. The reference beam 302 is combined interferometrically with the OCT return beam 301 on its return within the OCT imaging apparatus 300. The amount of delay in the reference delay optical path is adjustable by moving the moveable mirror 330 to equalize the optical paths of the OCT return beam 301 and the reference beam 302. For best axial OCT resolution, the OCT return beam 301 and the reference beam 302 are also dispersion compensated to equalize the group velocity dispersion within the two arms of the OCT interferometer.

When the combined laser/OCT/illumination/aiming beam 701 is delivered through the cornea 3 and the anterior chamber 7, the combined beam passes through posterior and anterior surface of the cornea at a steep angle, far from normal incidence. These surfaces in the path of the combined laser/OCT/illumination/aiming beam 701 create excessive astigmatism and coma aberrations that need to be compensated for.

Figure 9B:
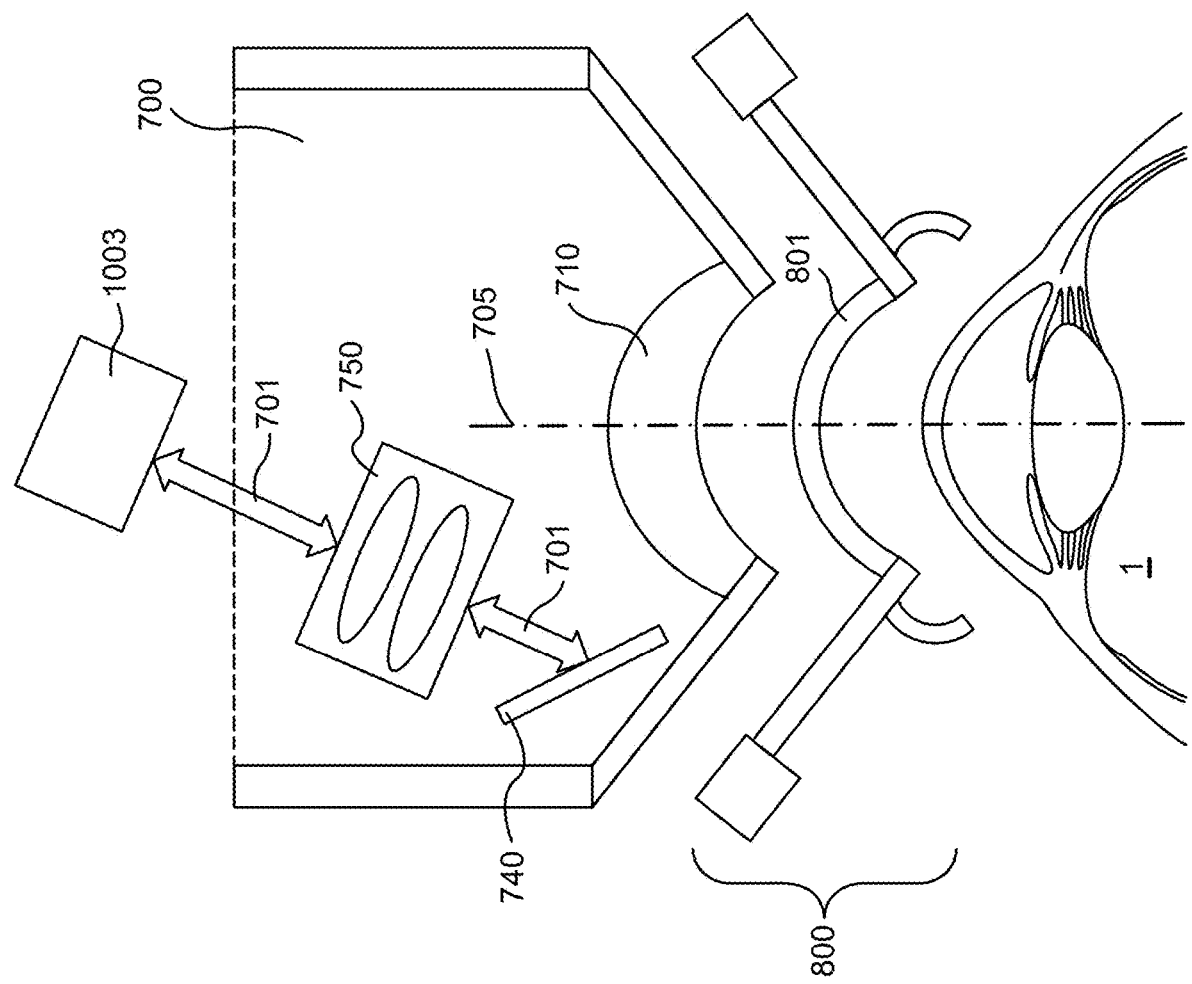

With reference to FIGS. 9a and 9b, in an embodiment of the integrated surgical system 1000, optical components of the focusing objective 700 and patient interface 800 are configured to minimize spatial and chromatic aberrations and spatial and chromatic distortions. FIG. 9a shows a configuration when both the eye 1, the patient interface 800 and the focusing objective 700 all coupled together. FIG. 9b shows a configuration when both the eye 1, the patient interface 800 and the focusing objective 700 all detached from one another.

The patient interface 800 optically and physically couples the eye 1 to the focusing objective 700, which in turn optically couples with other optic components of the integrated surgical system 1000. The patient interface 800 serves multiple functions. It immobilizes the eye relative to components of the integrated surgical system; creates a sterile barrier between the components and the patient; and provides optical access between the eye and the instrument. The patient interface 800 is a sterile, single use disposable device and it is coupled detachably to the eye 1 and to the focusing objective 700 of the integrated surgical system 1000.

Figure 9C:
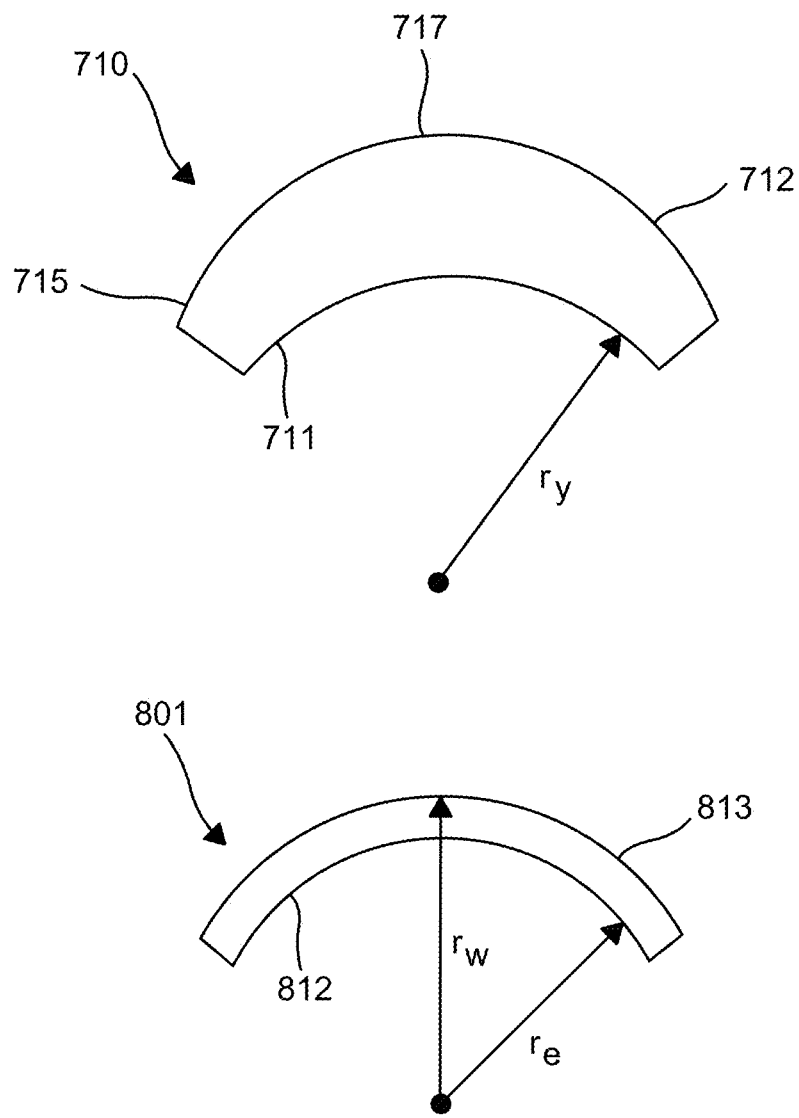
FIG. 9c is a schematic illustration of components of the focusing objective and the patient interface included in FIGS. 9a and 9b.

The patient interface 800 includes a window 801 having an eye-facing, concave surface 812 and an objective-facing, convex surface 813 opposite the concave surface. The window 801 thus has a meniscus form. With reference to FIG. 9c, the concave surface 812 is characterized by a radius of curvature $r_e$, while the convex surface 813 is characterized by a radius of curvature $r_w$. The concave surface 812 is configured to couple to the eye, either through a direct contact or through index matching material, liquid, or gel, placed in between the concave surface 812 and the eye 1. The window 801 may be formed of glass and has a refractive index $n_w$. In one embodiment, the window 801 is formed of fused silica and has a refractive index $n_w$ of 1.45. Fused silica has the lowest index from common inexpensive glasses. Fluoropolymers such as the Teflon AF are another class of low index materials that have refractive indices lower than fused silica, but their optical quality is inferior to glasses and they are relatively expensive for high volume production. In another embodiment the window 801 is formed of the common glass BK7 and has a refractive index $n_w$ of 1.50. A radiation resistant version of this glass, BK7G18 from Schott A G, Mainz, Germany, allows gamma sterilization of the patient interface 800 without the gamma radiation altering the optical properties of the window 801.

Returning to FIGS. 9a and 9b, the window 801 is surrounded by a wall 803 of the patient interface 800 and an immobilization device, such as a suction ring 804. When the suction ring 804 is in contact with the eye 1, an annular cavity 805 is formed between the suction ring and the eye. When vacuum applied to the suction ring 804 and the cavity via a vacuum tube a vacuum pump (not shown in FIGS. 9a and 9b), vacuum forces between the eye and the suction ring attach the eye to the patient interface 800 during surgery. Removing the vacuum releases or detach the eye 1.

The end of the patient interface 800 opposite the eye 1 includes an attachment interface 806 configured to attach to the housing 702 of the focusing objective 700 to thereby affix the position of the eye relative to the other components of the integrated surgical system 1000. The attachment interface 806 can work with mechanical, vacuum, magnetic or other principles and it is also detachable from the integrated surgical system.

The focusing objective 700 includes an aspheric exit lens 710 having an eye-facing, concave surface 711 and a convex surface 712 opposite the concave surface. The exit lens 710 thus has a meniscus form. While the exit lens 710 shown in FIGS. 9a and 9b is an aspheric lens giving more design freedom, in other configurations the exit lens may be a spherical lens. Alternatively, constructing the exit lens 710 as a compound lens, as opposed to a singlet, allows more design freedom to optimize the optics while preserving the main characteristics of the optical system as presented here. With reference to FIG. 9c, the concave surface 711 is characterized by a radius of curvature $r_y$, while the convex surface 712 is characterized by an aspheric shape. The aspheric convex surface 712 in combination with the spherical concave surface 711 result in an exit lens 710 having varying thickness, with the outer perimeter edges 715 of the lens being thinner than the central, apex region 717 of the lens. The concave surface 711 is configured to couple to the convex surface 813 of the window 801. In one embodiment, the exit lens 710 is formed of fused silica and has a refractive index $n_x$ of 1.45.

Figure 10A:
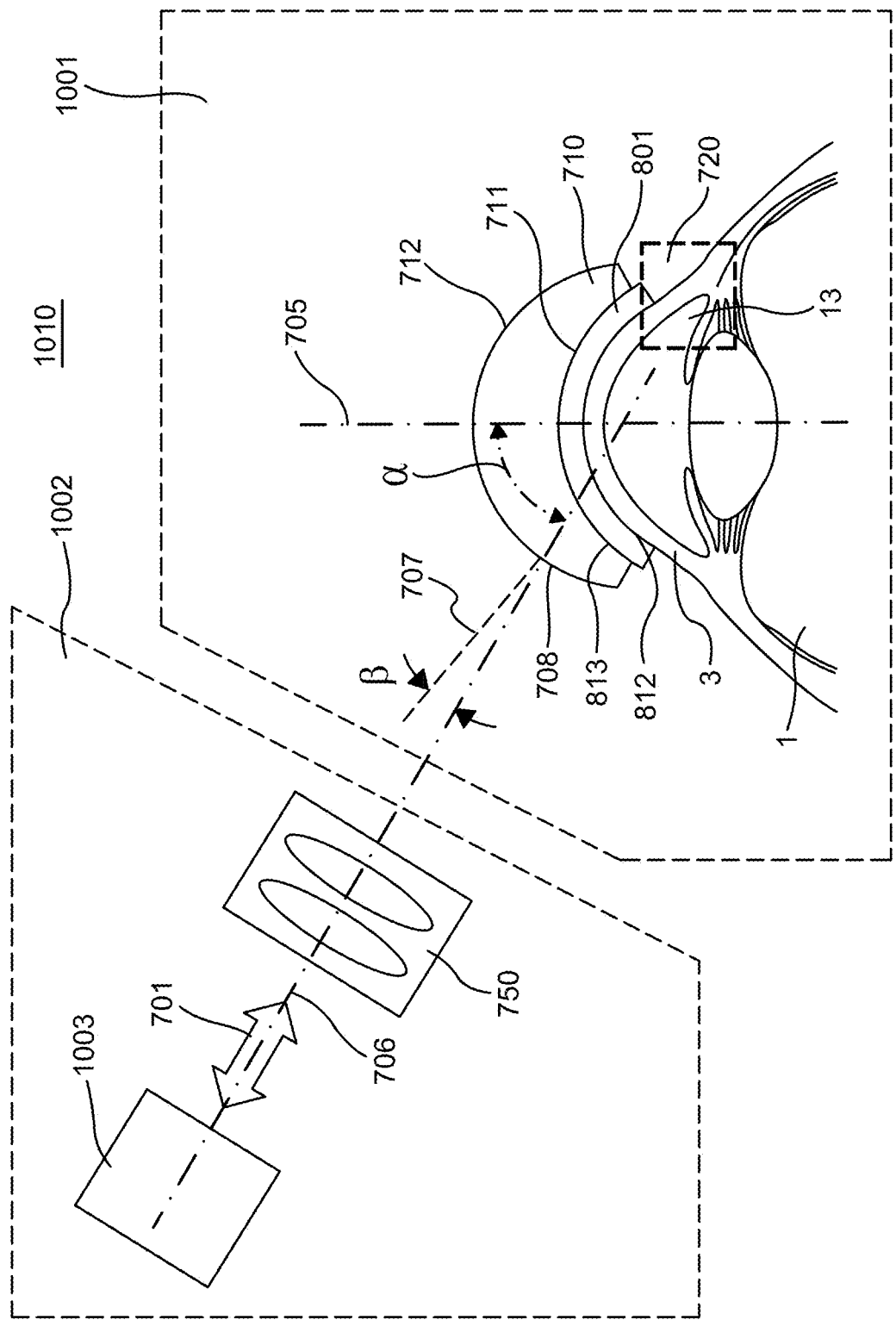
FIGS. 10a and 10b are schematic illustrations of components of the integrated surgical system of FIGS. 7 and 8 functionally arranged to form a first optical system and a second optical subsystem that enable access to the to the irido-corneal angle along the angled beam path of FIG. 6.
Figure 10B:
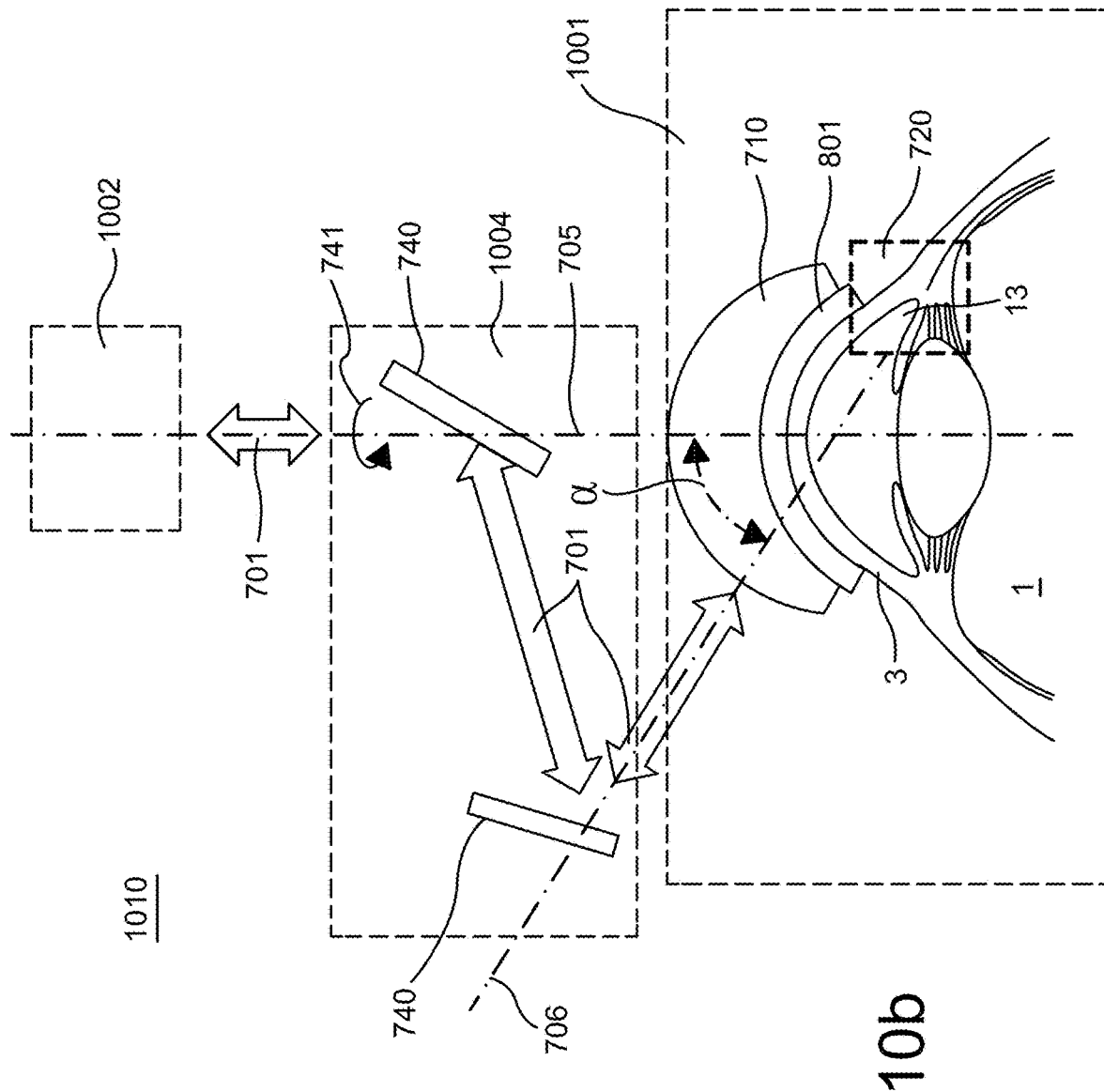
Figure 10C:
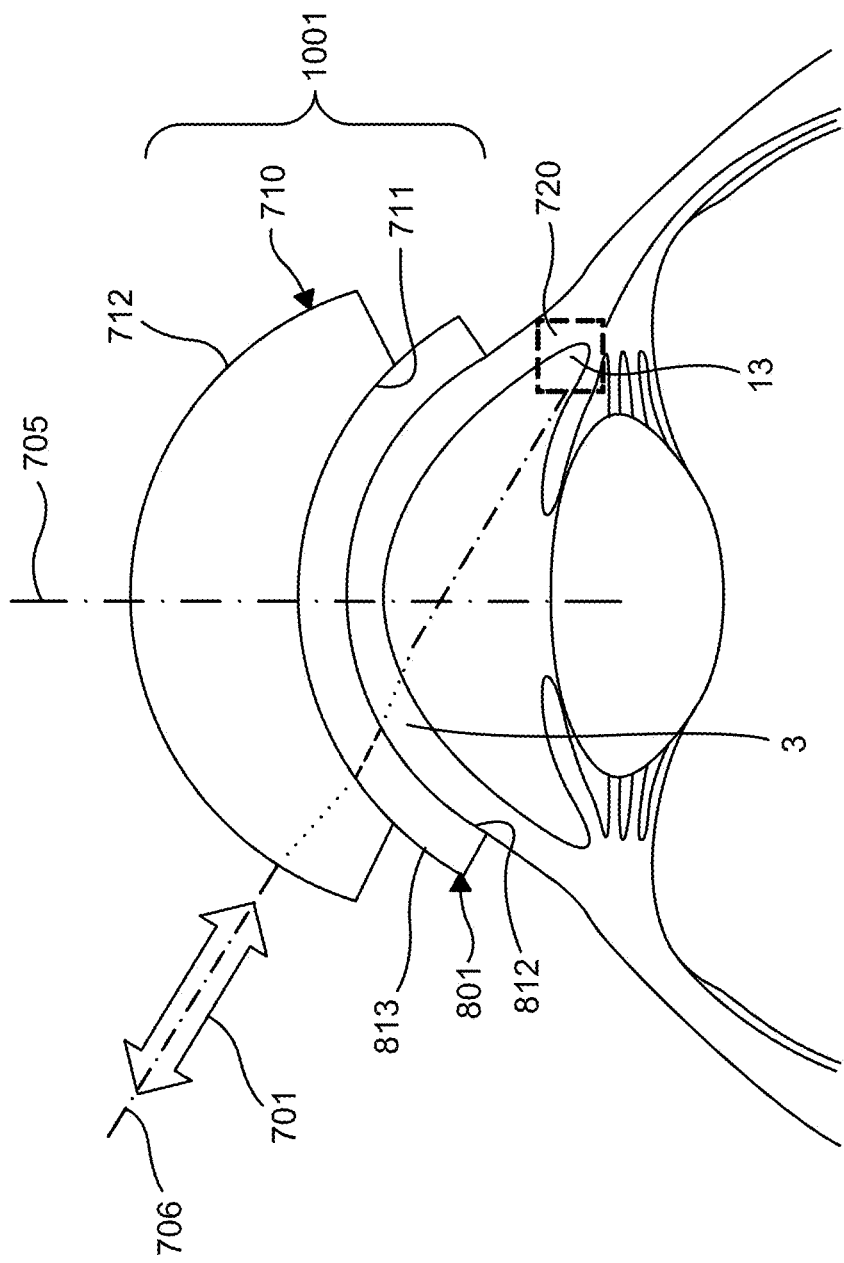
FIG. 10c is a schematic illustration of a beam passing through the first optical subsystem of FIGS. 10a and 10b and into the eye.

FIGS. 10a and 10b are schematic illustrations of components of the integrated surgical system of FIGS. 7 and 8 functionally arranged to form an optical system 1010 having a first optical subsystem 1001 and a second optical subsystem 1002 that enable access to a surgical volume 720 in the irido-corneal angle. Each of FIGS. 10a and 10b include components of the focusing objective 700 and the patient interface 800 of FIG. 9a. However, for simplicity, the entirety of the focusing objective and the patient interface are not included in FIGS. 10a and 10b. Also, for additional simplicity in FIG. 10a, the reflecting surface 740 of FIGS. 9a and 9b is not included and the combined laser/OCT/visual beam 701 shown in FIG. 9a is unfolded or straightened out. It is understood by those skilled in the art that adding or removing planar beam folding mirrors does not alter the principal working of the optical system formed by the first optical subsystem and the second optical subsystem. FIG. 10c is a schematic illustration of a beam passing through the first optical subsystem of FIGS. 10a and 10b.

With reference to FIG. 10a, a first optical subsystem 1001 of the integrated surgical system 1000 includes the exit lens 710 of a focusing objective 700 and the window 801 of a patient interface 800. The exit lens 710 and the window 801 are arranged relative to each other to define a first optical axis 705. The first optical subsystem 1001 is configured to receive a beam, e.g., a combined laser/OCT/visual beam 701, incident at the convex surface 712 of the exit lens 710 along a second optical axis 706, and to direct the beam toward a surgical volume 720 in the irido-corneal angle 13 of the eye.

During a surgical procedure, the first optical subsystem 1001 may be assembled by interfacing the convex surface 813 of the window 801 with the concave surface 711 of the exit lens 710. To this end, a focusing objective 700 is docked together with a patient interface 800. As a result, the concave surface 711 of the exit lens 710 is coupled to the convex surface 813 of the window 801. The coupling may be by direct contact or through a layer of index matching fluid. For example, when docking the patient interface 800 to focusing objective 700, a drop of index matching fluid can be applied between the contacting surfaces to eliminate any air gap that may be between the two surfaces 711, 813 to thereby help pass the combined laser/OCT/visual beam 701 through the gap with minimal Fresnel reflection and distortion.

In order to direct the beam toward the surgical volume 720 in the irido-corneal angle 13 of the eye, the first optical subsystem 1001 is designed to account for refraction of the beam 701 as it passes through the exit lens 710, the window 801 and the cornea 3. To this end, and with reference to FIG. 10c, the refractive index $n_x$ of the exit lens 710 and the refractive index $n_w$ of the window 801 are selected in view of the refractive index $n_c$ of the cornea 3 to cause appropriate beam bending through the first optical subsystem 1001 so that when the beam 701 exits the subsystem and passes through the cornea 3, the beam path is generally aligned to fall within the irido-corneal angle 13.

Continuing with reference to FIG. 10c and beginning with the interface between the window 801 and the cornea 3. Too steep of an angle of incidence at the interface where the combined laser/OCT/visual beam 701 exits the window 801 and enters the cornea 3, i.e., at the interface between the concave surface 812 of the window and the convex surface of the cornea 3, can create excessive refraction and distortion. To minimize refraction and distortion at this interface, in one embodiment of the first optical subsystem 1001, the refractive index of the window 801 is closely matched to the index of the cornea 3. For example, as describe above with reference to FIGS. 9a and 9b, the window 801 may have a refractive index lower than 1.42 to closely match the cornea 3, which has a refractive index of 1.36.

Excessive refraction and distortion at the interface where the combined laser/OCT/visual beam 701 exits the window 801 and enters the cornea 3 may be further compensated for by controlling the bending of the beam 701 as it passed through the exit lens 710 and the window 801. To this end, in one embodiment of the first optical subsystem 1001 the index of refraction $n_w$ of the window 801 is larger than each of the index of refraction $n_x$ of the exit lens 710 and the index of refraction $n_c$ of the cornea 3. As a result, at the interface where the combined laser/OCT/visual beam 701 exits the exit lens 710 and enters the window 801, i.e., interface between the concave surface 711 of the exit lens and the convex surface 813 of the window, the beam passes through a refractive index change from high to low that cause the beam to bend in a first direction. Then, at the interface where the combined laser/OCT/visual beam 701 exits the window 801 and enters the cornea 3, i.e., interface between the concave surface 812 of the exit lens and the convex surface of the cornea, the beam passes through a refractive index change from low to high that cause the beam to bend in a second direction opposite the first direction.

The shape of the window 801 is chosen to be a meniscus lens. As such, the incidence angle of light has similar values on both surfaces 812, 813 of the window 801. The overall effect is that at the convex surface 813 the light bends away from the surface normal and at the concave surface 812 the light bends towards the surface normal. The effect is like when light passes through a plan parallel plate. Refraction on one surface of the plate is compensated by refraction on the other surface a light passing through the plate does not change its direction. Refraction at the entering, convex surface 712 of the exit lens 710 distal to the eye is minimized by setting the curvature of the entering surface such that angle of incidence β of light 701 at the entering surface is close to a surface normal 707 to the entering surface at the intersection point 708.

Here, the exit lens 710, the window 801, and the eye 1 are arranged as an axially symmetric system with a first optical axis 705. In practice, axial symmetry is an approximation because of manufacturing and alignment inaccuracies of the optical components, the natural deviation from symmetry of the eye and the inaccuracy of the alignment of the eye relative to the window 801 and the exit lens 710 in a clinical setting. But, for design and practical purposes the eye 1, the window 801, and the exit lens 710 are considered as an axially symmetric first optical subsystem 1001.

With continued reference to FIG. 10a, a second optical subsystem 1002 is optically coupled to the first optical subsystem 1001 at an angle α relative to the first optical axis 705 of the first optical subsystem 1001. The advantage of this arrangement is that both optical subsystems 1001, 1002 can be designed at a much lower numerical aperture compared to a system where all optical components are designed on axis with a common optical axis.

The second optical subsystem 1002 includes a relay lens 750 that, as previously described with reference to FIG. 8, generates a conjugate surgical volume 721 of the surgical volume 720 within the eye. The second optical subsystem 1002 includes various other components collectively indicated as an optical subsystem step 1003. Referring to FIG. 8, these components may include a femtosecond laser source 200, an OCT imaging apparatus 300, a visual observation device 400, beam conditioners and scanners 500, and beam combiners 600.

The second optical subsystem 1002 may include mechanical parts (not shown) configured to rotate the entire second optical subsystem around the first optical axis 705 of the first optical subsystem 1001. This allows optical access to the whole 360-degree circumference of the irido-corneal angle 13 of the eye 1. This embodiment of the integrated surgical system 1000 is described later below with reference to FIGS. 22 and 23.

With reference to FIG. 10b, flexibility in arranging the first and second optical subsystems 1001, 1002, relative to each other may be provided by an optical assembly 1004 interposed between the optical output of the second optical subsystem 1002 and the optical input of the first optical subsystem 1001. In one embodiment, the optical assembly 1004 may include one or more reflecting surfaces 740, which may be a planar beam-folding mirrors, facets inside an optic (not shown), prisms (not shown) or optical gratings (not shown) configured to receive the optical output, e.g., combined laser/OCT/visual beam 701, of the second optical subsystem 1002, change or adjust the direction of the combined laser/OCT/visual beam, and direct the beam to the optical input of the first optical subsystem 1001 while preserving the angle α between the first optical axis 705 and the second optical axis 706.

In another configuration, the optical assembly 1004 with the reflective surface 740 further includes mechanical parts (not shown) configured to rotate the assembly around the first optical axis 705 of the first optical subsystem 1001 while keeping the second optical subsystem 1002 stationary. Accordingly, the second optical axis 706 of the second optical subsystem 1002 can be rotated around the first optical axis 705 of the first optical subsystem 1001. This allows optical access to the whole 360-degree circumference of the irido-corneal angle 13 of the eye 1.

With considerations described above with reference to FIGS. 9a, 9b and 9c, the design of the first optical subsystem 1001 is optimized for angled optical access at an angle α relative to the first optical axis 705 of the first optical subsystem 1001. Optical access at the angle α compensates for optical aberrations of the first optical subsystem 1001. Table 1 shows the result of the optimization at access angle α=72 degrees with Zemax optical design software package. This design is a practical embodiment for image guided femtosecond glaucoma surgery.

TABLE 1

| Surface | Structure and Material | Refractive index | Radius [mm] | Center Thickness [mm] |
|---|---|---|---|---|
| concave surface 711, convex surface 712 | Exit lens 710 of focusing objective. Fused silica | 1.45 | −10 | 4.5 |
| concave surface 812, convex surface 813 | Window 801 of patient interface. BK7G18 | 1.50 | −10.9 | 1.0 |
| 3 | Cornea | 1.36 | −7.83 | 0.54 |
| 8 | Aqueous humor | 1.32 | −6.53 | 3.5 |
| Target | Ophthalmic tissue | 1.38 | N/A | 0 to 1 mm |

This design produces diffraction limited focusing of 1030 nm wavelength laser beams and 850 nm wavelength OCT beams with numerical aperture (NA) up to 0.2. In one design, the optical aberrations of the first optical subsystem are compensated to a degree that the Strehl ratio of the first optical subsystem for a beam with numerical aperture larger than 0.15 at the irido-corneal angle is larger than 0.9. In another design, the optical aberrations of the first optical subsystem are partially compensated, the remaining uncompensated aberrations of the first optical system are compensated by the second optical subsystem to a degree that the Strehl ratio of the combined first and second optical subsystem for a beam with numerical aperture larger than 0.15 at the irido-corneal angle is larger than 0.9.

Laser Surgical Treatments

The integrated surgical system 1000 enables laser treatment of tissues, especially ocular tissue structures in the irido-corneal angle of the eye. In one embodiment, the laser is a femtosecond laser. A femtosecond laser provides highly localized, non-thermal photo-disruptive laser-tissue interaction with minimal collateral damage to surrounding ocular tissue. Photo-disruptive interaction of the laser is utilized in optically transparent tissue. The principal mechanism of laser energy deposition into the ocular tissue is not by absorption but by a highly nonlinear multiphoton process. This process is effective only at the focus of the pulsed laser where the peak intensity is high. Regions where the beam is traversed but not at the focus are not affected by the laser. Therefore, the interaction region with the ocular tissue is highly localized both transversally and axially along the laser beam.

Prior to laser treatment, the user specifies the size and shape of the treatment pattern to be scanned by the femtosecond laser beam. The specification of the treatment pattern includes the length, width, and depth of the pattern as well as the separation between photo-disruption sites in a single depth and plane or layer separation of photo-disruption sites at different depths. The specifications are inputted to a processor that analyzes the specification data to compute the three-dimensional (3D) location of each photo-disruption site within the treatment pattern. In addition, for each 3D location the processor determines whether the delivery of optical energy to that location is sufficient to affect ocular tissue. As a result of this analysis, each photo-disruption site is assigned a four-dimensional coordinate. The first three coordinates define the 3D location of a single photo-disruption site. These first three coordinates may be represented in Cartesian, Spherical, or other coordinate representation. The fourth coordinate is a binary bit that determines whether the delivery of optical energy to the location specified by the proceeding three coordinates is sufficient to affect ocular tissue. The processor then saves the four-dimensional coordinate in a memory of the processor. The processor continues to compute and save a four-dimensional coordinate for each photo-disruption site within the treatment pattern until the pattern has been exhausted. The final result is N four-dimensional coordinates, where N is the total number of photo-disruption sites in the treatment pattern, saved into memory. The aggregate of these coordinates represents the computational specification of the treatment pattern broken down by individual sites within a treatment plane at a specified depth and by the separation between adjacent treatment planes.

During a laser surgical treatment, a laser focus is scanned in accordance with a computed specification of the treatment pattern saved in memory. For each photo-disruption site, the processor moves the scanning device to focus the femtosecond laser to the computed 3D location. The processor then checks the fourth coordinate to determine if the delivery of optical energy to the location should be sufficient to affect ocular tissue. If the fourth bit allows that such energy should be delivered, then processor enables the delivery of optical energy to the location sufficient to affect ocular tissue, and then reads the next set of coordinates for the treatment pattern. If the fourth bit prohibits such energy, then the processor implements additional components for preventing optical energy from affecting tissue at this location. In this manner, a number of photo-disruptions sites, or spots, affecting tissue in layers or planes, each plane being located at a different depth in ocular tissue is generated.

At instances during the scanning specified by the computed treatment pattern, the laser delivers optical energy sufficient to affect a cell or spot of ocular tissue. The size of a spot or cell is determined by the extent of the influence of laser-tissue interaction, and in the case of a femtosecond laser is on the order of a few micrometers (μm). The cumulation of these spots over the course of scanning through a number of tissue planes results in a three-dimensional volume of ocular tissue comprising multiple sheets or layers of affected tissue.

Because the laser interaction volume is small, the interaction of ocular tissue with each laser shot of a repetitive laser breaks down ocular tissue locally at the focus of the laser. The pulse duration of the laser for photo-disruptive interaction in ocular tissue can range from several femtoseconds to several nanoseconds and pulse energies from several nanojoules to tens of microjoules. The laser pulses at the focus, through multiphoton processes, breaks down chemical bonds in the molecules, locally photo-dissociate tissue material and create gas bubbles in wet tissue. The breakdown of tissue material and mechanical stress from bubble formation fragments the tissue and create clean continuous cuts when the laser pulses are laid down in proximity to one another along geometrical lines and surfaces.

Figure 11:
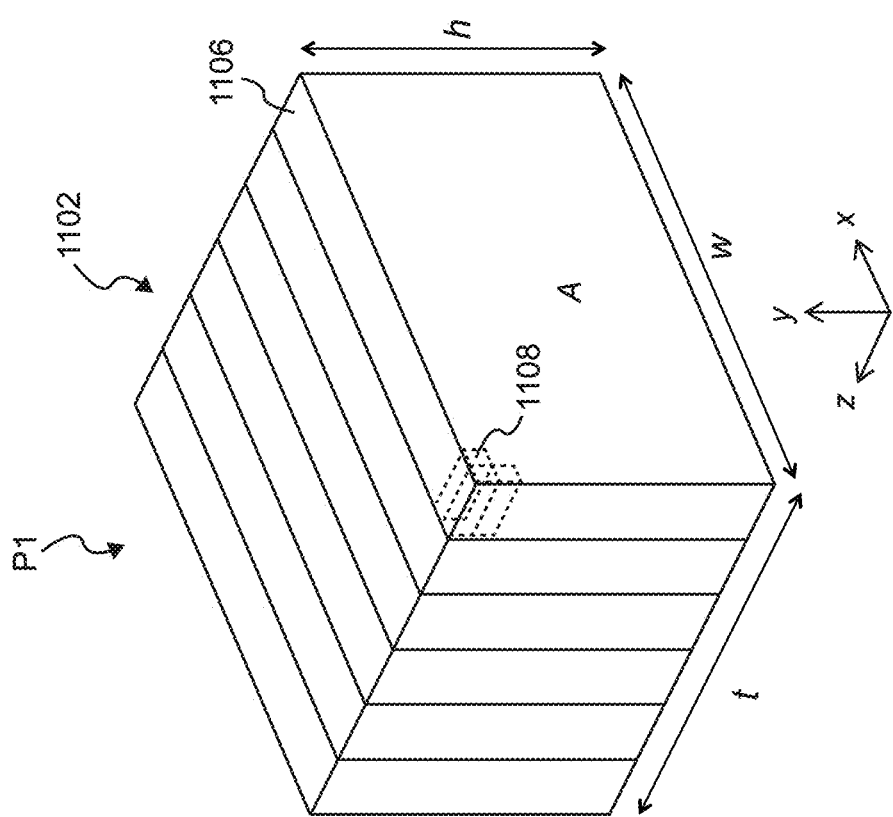
FIG. 11 is an illustration of example laser treatment patterns formed by a number of treatment planes and used by the integrated surgical system of FIG. 7 to treat a target volume of tissue.

The instances at which optical energy is delivered during a laser treatment are defined by a laser treatment pattern. With reference to FIG. 11, a treatment pattern P1 may be in the form of any geometric structure, e.g., an extended rectangle 1102, and may encompass a number of sheets or layers, referred to herein as treatment planes 1106, adjacent each other. Each treatment plane 1106, in turn, encompasses individual cells 1108 arranged in regularly spaced rows and columns. A treatment pattern P1 may be characterized by x, y, z dimensions, with x, y, z coordinates of the cells 1108 being calculated sequentially from neighbor to neighbor in the order of a column location (x coordinate), a row location (y coordinate), and a layer location (z coordinate). A treatment pattern P1 as such, defines a three-dimensional model of ocular tissue to be modified by a laser. Additional example treatment patterns are disclosed in U.S. patent application Ser. No. 16/838,858, titled "Method, System, and Apparatus for Generating Three-Dimensional Treatment Patterns for Laser Surgery of Glaucoma," the disclosure of which is incorporated by reference herein.

The integrated surgical system 1000 disclosed herein is configured to scan its laser focus in a scanning pattern. The scanning pattern may be characterized by a geometry and movement of the laser focus. For example, the geometry may be symmetric like a rectangle, square or circle or it may be non-symmetric and may be defined by x and y dimensions. Movement of the laser focus through a geometry may be raster like, circular, spiral, zig-zag, etc. Accordingly, the scanning pattern of the integrated surgical system 1000 may be referred to as having a raster pattern, a circular pattern, a spiral pattern, or a non-symmetric pattern.

Figure 12:
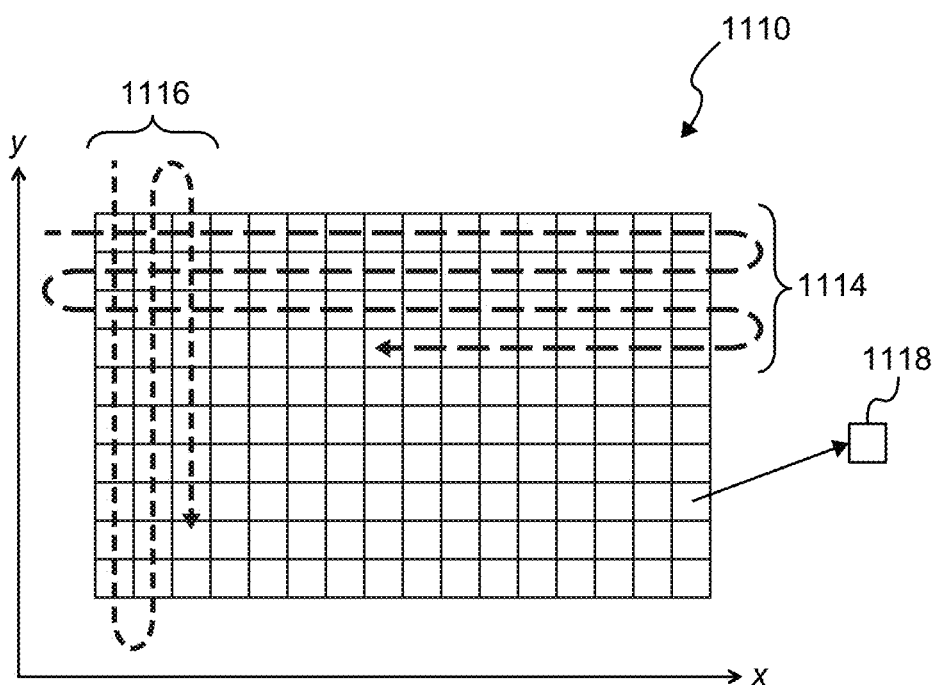
FIG. 12 is a schematic illustration of an example scanning pattern used by the integrated surgical system of FIG. 7 when scanning a laser focus and comprised of a two-dimensional array of instances during which optical energy may be delivered to tissue.

With reference to FIG. 12, a scanning pattern 1110 having a rectangular geometry and a raster movement pattern is shown. The geometry of the scanning pattern 1110 is defined by a horizontal dimension x and a vertical dimension y, which dimensions are typically pre-set or programmed in the control system 100 of the integrated surgical system 1000 for a given laser. For example, a femtosecond laser may have a scanning pattern 1110, where x=800 μm and y=300 μm. During laser treatment, the laser focus is located at a depth in tissue and then scanned either in a horizontal scan 1114 or a vertical scan 1116 to define a layer or plane of laser scanning.

The integrated surgical system 1000 is also configured to deliver optical energy during laser scanning. To this end, the system is programmed to deliver a pulse shot of the laser at each of a plurality of instances 1118 as pre-computed by a processor during a horizontal scan 1114 or vertical scan 1116, whichever the case may be. For example, with reference to FIG. 12, during a horizontal scan 1114 a laser shot sufficient to affect a cell or spot of ocular tissue may be delivered to tissue at each instance 1118 represented by a square. As described above, these instances 1118 are pre-computed by the processor. The delivery of laser shots at each instance 1118 is repeated for each row in a horizontal scan 1114. When scanning is complete, the multiple instances 1118 of optical energy delivery produce a layer of laser-affected tissue. The thickness of the layer of laser-affected tissue is a function of the energy of the laser shots. For example, a femtosecond laser with a pulse energy between 3-5 μJ. may result in a layer thickness of between 3-4 μm.

With reference to FIGS. 13-16, a treatment pattern P1 is typically defined by a set of surgical parameters. The surgical parameters may include a treatment area A that represents a surface area or layer of ocular tissue through which the laser will travel. The treatment area A is determined by the treatment height, h, and the width or lateral extent or circumferential extent of the treatment, w. The width or lateral extent may be defined in terms of a measure or length along a portion of the circumference of the irido-corneal angle. The circumference of the irido-corneal angle is also referred to herein as the circumferential angle. For example, the width w may be defined in terms of an angle, e.g., 90 degrees, around the circumferential angle. Movement in a direction along the width or circumferential extent, w is referred to herein as movement in a "circumferential" direction. Movement in a direction along the height, h, is referred to herein as movement in an "azimuthal" direction.

The surgical parameters may also include a treatment thickness t that represents the level to which the laser will cut into the ocular tissue from a distal extent 60 or border of the treatment volume at or near Schlemm's canal 18 to a proximal extent 62 or border at or near the surface of the trabecular meshwork 12. Thus, a laser applied in accordance with a treatment pattern may affect or produce a surgical volume that resembles the three-dimensional model of the treatment pattern.

Figure 13:
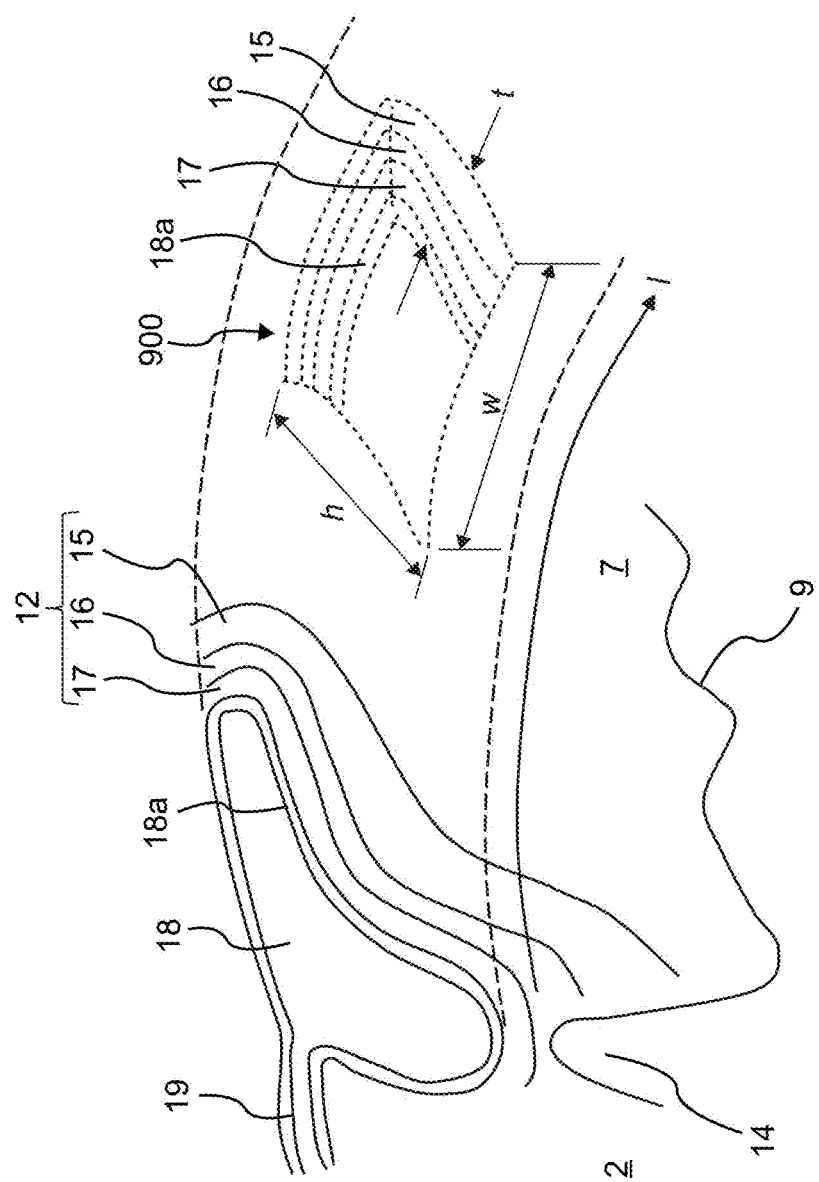
FIG. 13 is a three-dimensional schematic illustration of anatomical structures in the irido-corneal angle, including the trabecular meshwork, Schlemm's canal, a collector channel branching from the Schlemm's canal, and a cubic surgical volume of ocular tissue to be treated by the integrated surgical system of FIG. 7.
Figure 14:
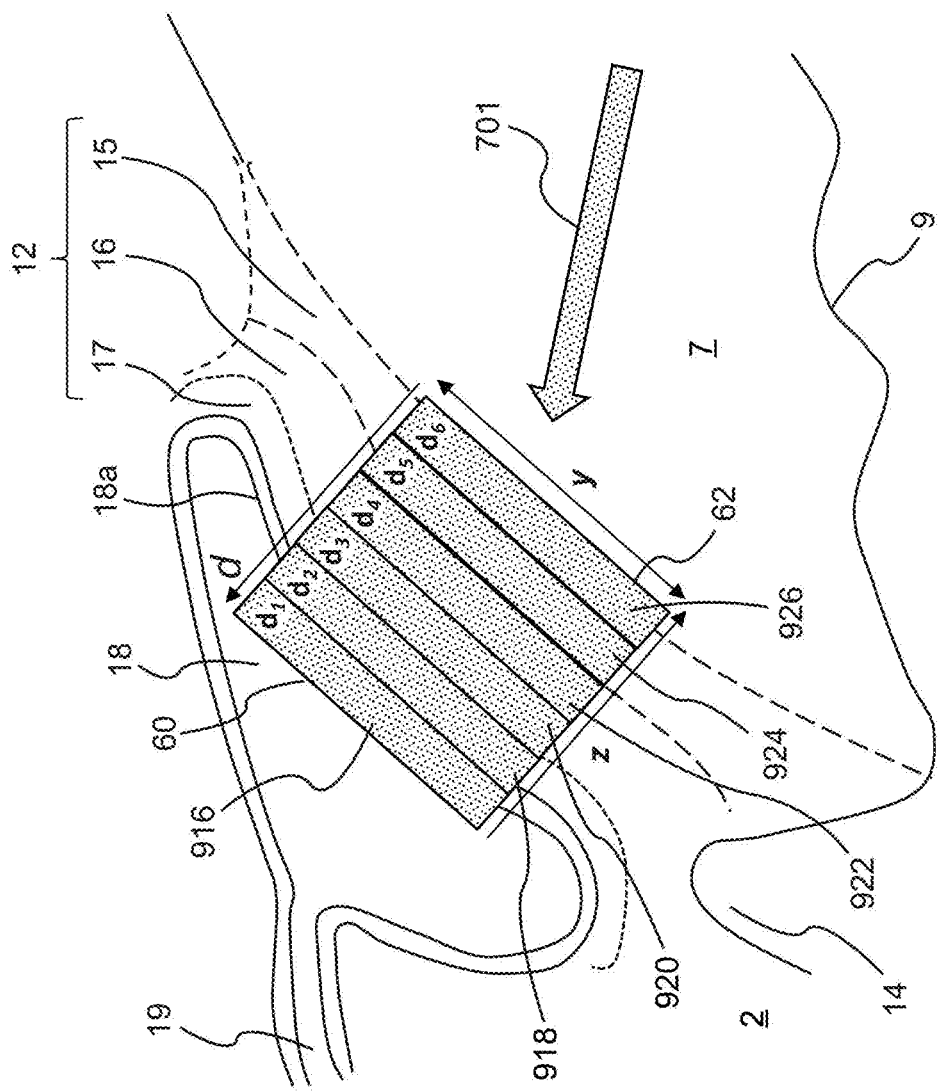
FIG. 14 is a two-dimensional schematic illustration of anatomical structures in the irido-corneal angle and a three-dimensional illustration of a laser treatment pattern to be applied by the integrated surgical system of FIG. 7 to affect the surgical volume of ocular tissue shown in FIG. 13.
Figure 14:
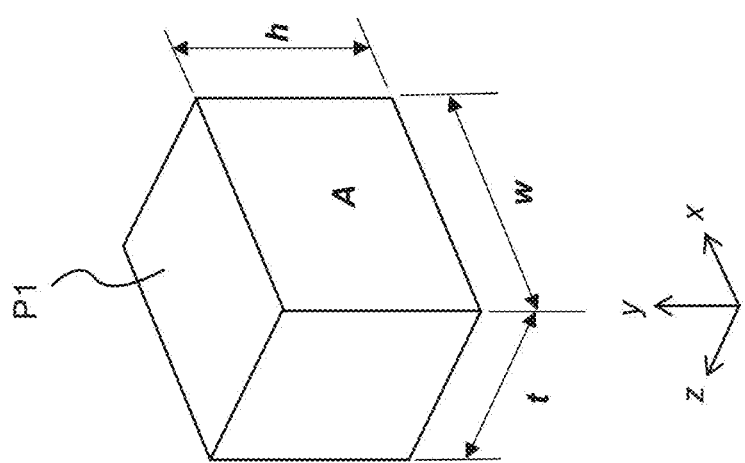

Additional surgical parameters define the placement of the surgical volume or affected volume within the eye. For example, placement parameters may include one or more of a location l, as shown in FIG. 13, that represents where the treatment is to occur relative to the circumferential angle of the eye, and a treatment depth d, as shown in FIG. 14, that represents a position of the three-dimensional model of ocular tissue relative to a reference eye structure. In the following, the treatment depth d is shown and described relative to the region where the anterior chamber 7 meets the trabecular meshwork 12. Together, the treatment pattern and the placement parameters define a treatment plan.

Different shapes and sizes of volumes of ocular tissue may be affected by controlling the delivery of optical energy to tissue during laser scanning based on different corresponding treatment patterns. For example, with reference to FIGS. 13-16, a cubic surgical volume 900 of ocular tissue may be treated in accordance with a treatment pattern P1, like the one shown in FIG. 11a. The surgical volume 900 of ocular tissue may comprise portions of the trabecular meshwork 12 and the Schlemm's canal 18. For example, the surgical volume 900 of ocular tissue shown in FIG. 13 includes portions of the uveal 15, the corneoscleral meshwork 16, the juxtacanalicular tissue 17, and the inner wall 18a of the Schlemm's canal 18.

Figure 15:
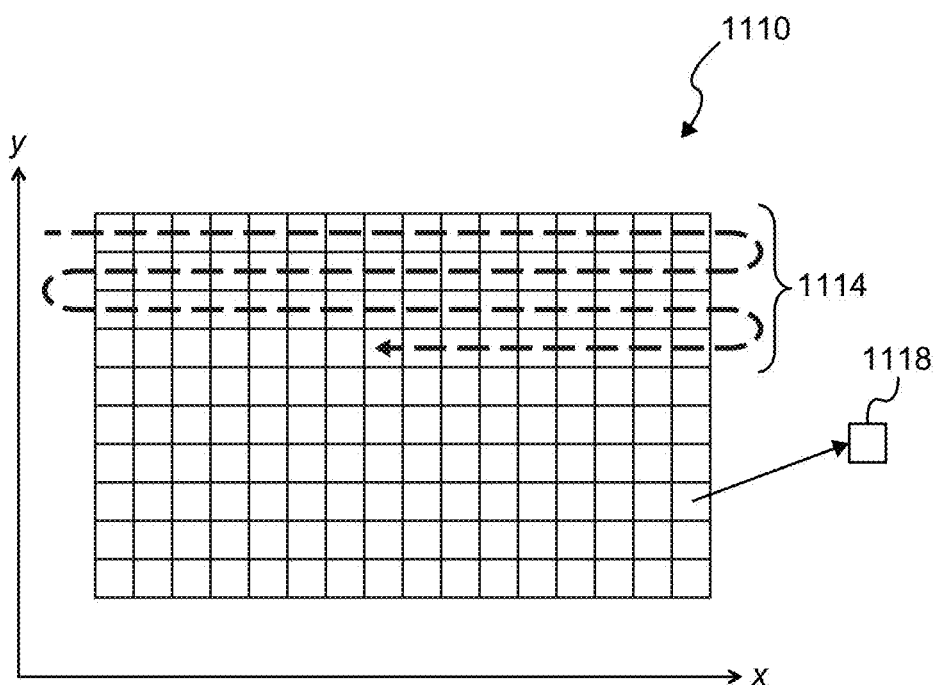
FIG. 15 is an illustration of a horizontal scan that includes a delivery of optical energy at each instance the pattern of FIG. 12.

With reference to FIG. 14, during a laser scanning procedure in accordance with treatment pattern P1, the focus of the laser beam 701 is initially located at a depth $d_1$. This depth $d_1$ places the laser focus in an initial layer 916 of tissue. Once the laser focus is positioned at the initial depth $d_1$, the focus is scanned in accordance with a horizontal scan 1114 through the scanning pattern 1110, with optical energy being delivered at each instance 1118 during the scan, as shown in FIG. 15. These instances 1118 where optical energy is delivered to tissue result in the photodisruption of the initial layer 916 of tissue and define an initial treatment plane at the initial layer of tissue.

With continued reference to FIG. 14, the focus of the laser beam 701 is then moved in the z direction toward the anterior chamber 7 to a subsequent depth $d_2$. The subsequent depth $d_2$ places the laser focus at a subsequent layer 918 of tissue. Once the laser focus is positioned at the subsequent depth $d_2$, the focus is scanned in accordance with a horizontal scan 1114 through the scanning pattern 1110, with optical energy being delivered at each instance 1118 during the scan, as shown in FIG. 15. These instances 1118 of optical energy delivery result in the photodisruption of the subsequent layer 918 of tissue and define a subsequent treatment plane at the subsequent layer of tissue. The foregoing movement of the focus of the laser beam 701 and laser scanning and optical energy delivery is repeated at depths $d_3$, $d_4$, $d_5$, and $d_6$ resulting in photodisruption of the subsequent layers 918, 920, 922, 924, 926 of tissue.

Figure 16:
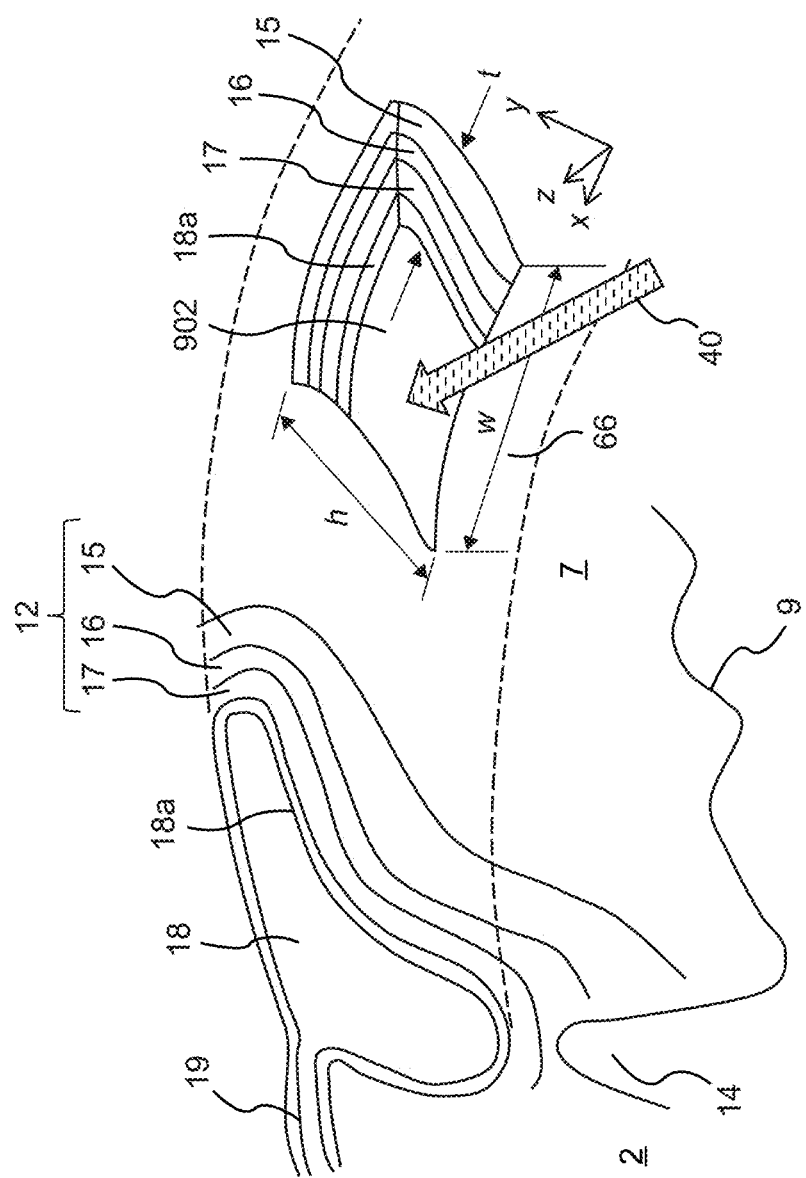
FIG. 16 is a three-dimensional schematic illustration of FIG. 11 subsequent to treatment of the surgical volume of ocular tissue by a laser based on the laser treatment pattern of FIG. 14 that forms an opening between the Schlemm's canal and the anterior chamber.

With reference to FIG. 16, photodisruption of the multiple layers forms an opening 902 between the anterior chamber 7 and the Schlemm's canal 18, thus completing the laser treatment procedure. The opening 902 resulting from laser application of the treatment pattern P1 resembles the surgical volume 900 and is characterized by an area A and thickness t similar to those of the surgical volume and the treatment pattern. The thickness t of the resulting opening 902 extends from the anterior chamber 7 and through the inner wall 18a of the Schlemm's canal 18, while the area A defines the cross-section size of the opening 902.

OCT Imaging of the Irido-Corneal Angle

In accordance with embodiments disclosed herein, as part of a laser surgical procedure, one or more OCT images of the irido-corneal angle may be obtained by the integrated surgical system 1000 and used to determine parameters of a surgical treatment pattern. To this end, and with reference to FIGS. 17, 18 and 22, a method of imaging and treating ocular tissue of an eye having a cornea, an iris, an anterior chamber, an irido-corneal angle, and a direction of view is disclosed.

Figure 17:
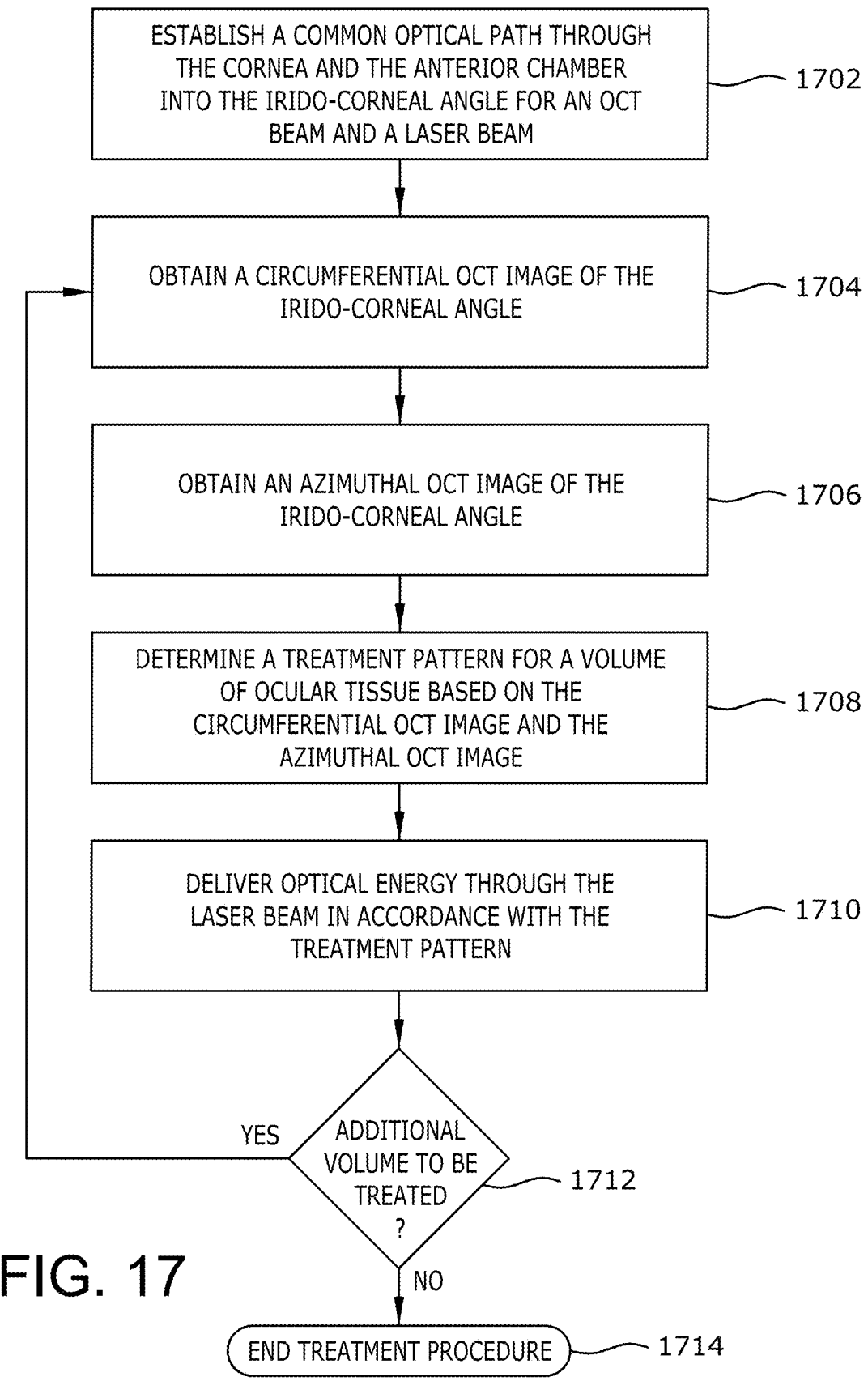
FIG. 17 is a flowchart of a method of imaging and treating ocular tissue of an eye.

At block 1702 of FIG. 17, and with additional reference to FIGS. 9a, 9b, 18, and 22, a common optical path for each of an OCT beam 301 and a laser beam 201 is established through the cornea and the anterior chamber into the irido-corneal angle. The beams 201, 301 may be so aligned by a first optical subsystem 1001 having optics including a reflective surface 740 and an exit lens 710, both which may be part of a focusing objective 700, and a window 801 of a patient interface 800. Optical features of the exit lens 710 and the window 801 are described above with reference to FIGS. 10a-10c. With reference to FIG. 10c, the optical path of the OCT beam 301 and the laser beam 201 into the irido-corneal angle 13 passes through the cornea at an angle offset from an optical axis 705 within the direction of view of the eye 1, and without passing through the scleral spur.

Figure 18:
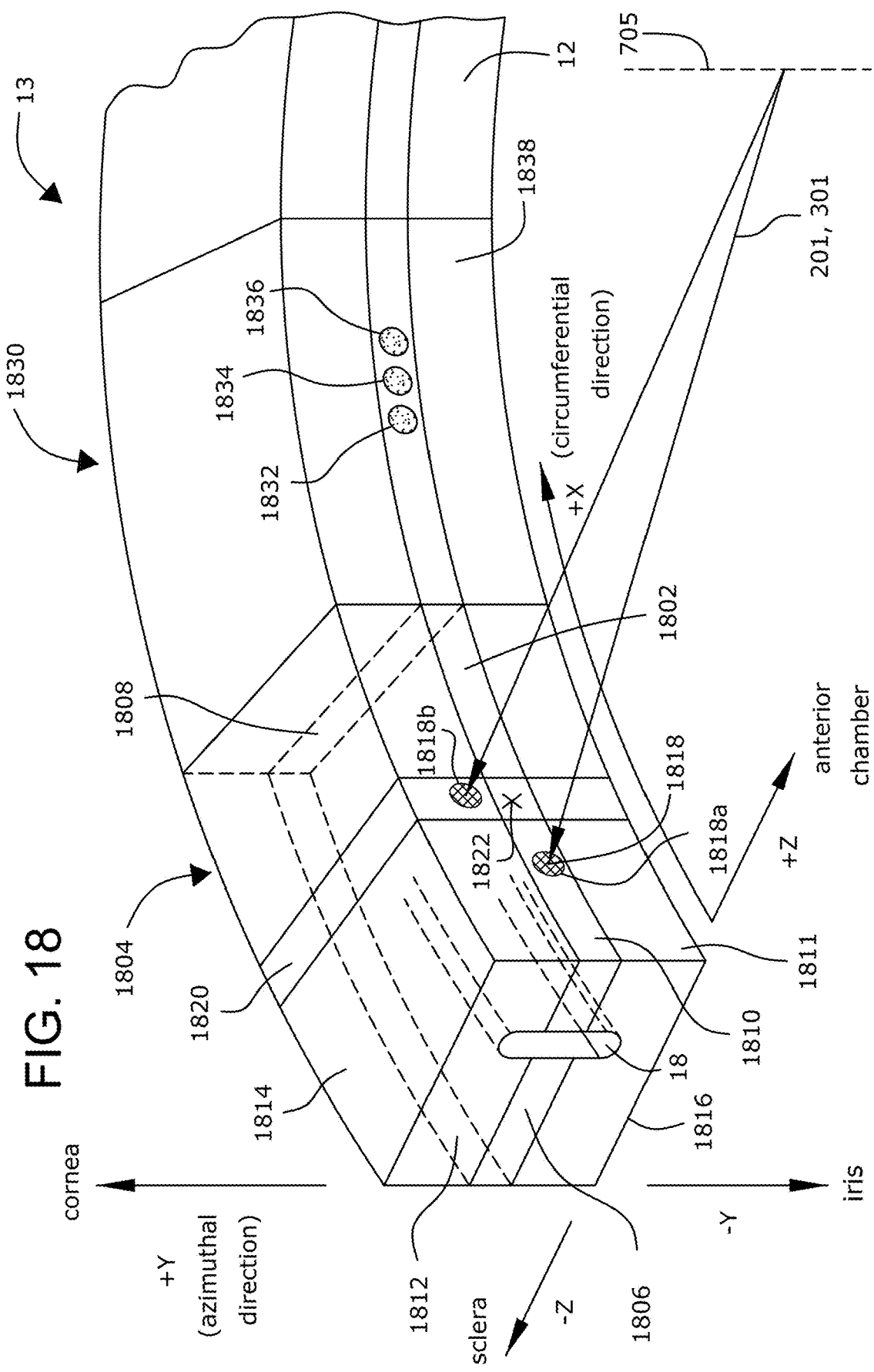
FIG. 18 is a three-dimensional schematic illustration of a portion of ocular tissue of the irido-corneal angle including the trabecular meshwork and the Schlemm's canal.
Figure 19A:
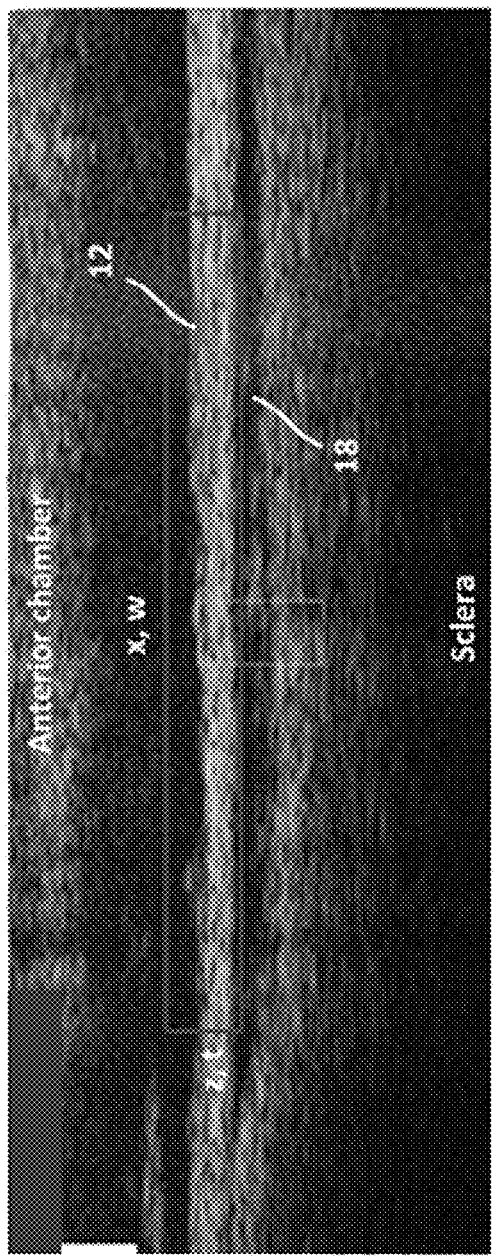
FIG. 19*a* is a circumferential OCT image of a portion of the irido-corneal angle.

At block 1704 of FIG. 17, and with additional reference to FIG. 18, a circumferential OCT image of the irido-corneal angle 13 may be obtained by scanning the OCT beam 301 through a circumferential plane 1802 of a segment 1804 of ocular tissue. The segment 1804 of ocular tissue may be all or part of the circumferential angle of the eye. All or a portion of this segment 1804 of ocular tissue may correspond to a target volume of ocular tissue that is to be treated with a laser. The circumferential plane 1802 is bound by a first circumferential boundary 1806, a second circumferential boundary 1808, an anterior-chamber boundary 1810 adjacent the anterior chamber, and a sclera boundary 1812 adjacent the sclera. The circumferential plane 1802 is located between a corneal boundary 1814 adjacent the cornea and an iris boundary 1816 adjacent the iris. For example, the azimuthal or height location of the circumferential plane 1802 may be located at or near the center of the height of the segment 1804 of ocular tissue, or in other words, midway between the corneal boundary 1814 and the iris boundary 1816. An example circumferential OCT image 1902 is shown in FIG. 19a. Anatomical landmarks visible in this circumferential OCT image 1902 include the trabecular meshwork 12 and the Schlemm's canal 18. From this circumferential OCT image 1902, the width or circumferential extent, w, and the thickness, t, of a treatment pattern P1 may be determined.

Because the laser beam 201 and the OCT beam 301 share the same scanning component 830, the laser beam is preferably maintained inactive during circumferential scanning of the OCT beam to avoid potential interference with the OCT beam. To this end, the laser source 200 that outputs the laser beam 201 may be turned off entirely so no laser beam is present, or the energy level of the laser source may be reduced so that the laser beam, while present together with the OCT beam, does not affect ocular tissue. In either case, laser treatment does not take place during the scanning of the OCT beam. Alternatively, the integrated surgical system 1000 may be configured with a separate scanning component 830 for the each of the laser beam 201 and the OCT beam 301, which would enable simultaneous delivery and scanning of an OCT beam and a laser beam.

With reference to FIG. 18, scanning the OCT beam 301 through the circumferential plane 1802 includes moving a focus 1818 of the OCT beam in the circumferential direction to each of a plurality of circumferential points or spots between the first circumferential boundary 1806 and the second circumferential boundary 1808. At each of the plurality of circumferential points 1818a between the first circumferential boundary 1806 and the second circumferential boundary 1808, the focus 1818 of the OCT beam 301 is moved in the z direction to each of a plurality of points or spots between the anterior-chamber boundary 1810 and the sclera boundary 1812.

The respective distances between the various boundaries may correspond to the scanning range of the OCT beam 301. For example, the distance between the first circumferential boundary 1806 and the second circumferential boundary 1808 may correspond to the scanning range of the OCT beam 301 in the x direction, i.e., the circumferential direction. The distance between the anterior-chamber boundary 1810 and the sclera boundary 1812, may corresponds to the scanning range of the OCT beam in the z direction. The distance between the corneal boundary 1814 and the iris boundary 1816 may correspond to the scanning range of the OCT beam 301 in the y direction, i.e., the azimuthal direction.

Regarding the scanning ranges of the OCT beam 301, and with reference to FIG. 22 (which is described in detail later below), the scanning range of the OCT beam 301 in the azimuthal direction typically depends on the scanning range of a scanning component 830, e.g., scanning mirrors, of the integrated surgical system 1000. The azimuthal scanning range may be between 0.01 mm and 2.00 mm, and is typically about 0.300 mm. The scanning range of the OCT beam 301 in the depth direction, i.e., the z direction, typically depends on the range of movement of the focusing optics in the z direction. The depth scanning range may be between 0.5 mm and 1.5 mm, and is typically about 1 mm. As described later below with reference to FIG. 22, focusing optics are located on a plate 844 that is configured to move back and forth in the z direction.

With respect to the range of circumferential scanning, in one configuration the scanning range of the OCT beam 301 depends on the scanning range of the scanning component 830, e.g., scanning mirrors, of the integrated surgical system 1000. The circumferential scanning range may be between 1 mm and 4 mm, and is typically about 2 mm. The circumferential scanning range may also be characterized in terms of degrees around the circumferential angle of the eye. The circumferential scanning range of the scanning mirrors 830 may be between 4 degrees and 20 degrees. The circumferential scanning range can be made as small as desired. The minimum length of 1 mm is a convenient distance that corresponds to about 4 degrees of irido-corneal angle.

In another configuration, the circumferential scanning range of the integrated surgical system 1000 is increased beyond that of scanning mirrors 830. In this configuration, the focus 1818 of the OCT beam 301 is moved to each of a plurality of circumferential points 1818*a* around the circumferential angle of the eye by rotation of a second optical subsystem 1002 relative to the optical axis 705. The rotation may be between the first circumferential boundary 1806 and the second circumferential boundary 1808, or between the first circumferential boundary and another boundary beyond the second circumferential boundary 1808. For example, the OCT beam 301 may be rotated 360 degrees around the circumferential angle of the eye. As described later below with reference to FIG. 22, the second optical subsystem 1002 includes an OCT imaging apparatus 300 that outputs the OCT beam 301 at points around the circumferential angle of the eye, and a focusing objective 700 that moves the focus 1818 of the OCT beam in the z direction to each of a plurality of points between the anterior-chamber boundary 1810 and the sclera boundary 1812.

Figure 19B:
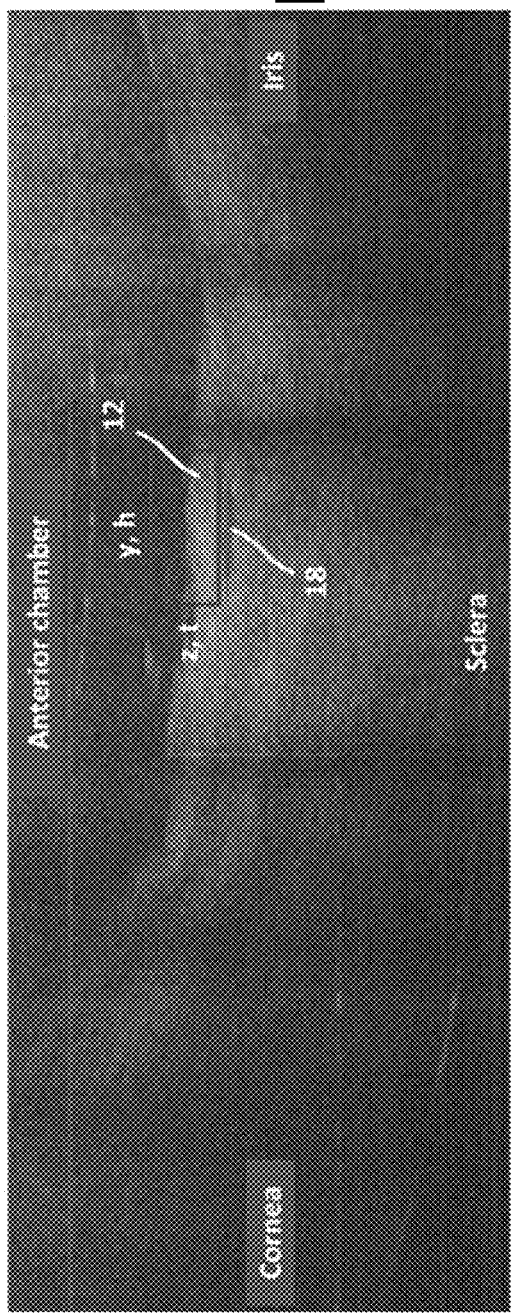
FIG. 19*b* is an azimuthal OCT image of a portion of the irido-corneal angle.

Returning to FIG. 17, and with additional reference to FIG. 18, at block 1706, an azimuthal OCT image of the irido-corneal angle 13 may be obtained by scanning the OCT beam 301 through an azimuthal slice 1820 of the segment 1804 of ocular tissue. The azimuthal slice 1820 is bound by the anterior-chamber boundary 1810, the sclera boundary 1812, the corneal boundary 1814, and the iris boundary 1816. The azimuthal slice 1820 is located between the first circumferential boundary 1806 and the second circumferential boundary 1808. An example azimuthal OCT image 1904 is shown in FIG. 19*b*. Anatomical landmarks visible in this azimuthal OCT image 1904 include the trabecular meshwork 12 and the Schlemm's canal 18. For example, the circumferential location of the azimuthal slice 1820 may be located at or near the circumferential center of the segment 1804 of ocular tissue, or in other words, midway between the first circumferential boundary 1806 and the second circumferential boundary 1808. From this azimuthal OCT image 1904 the height, h, and the thickness, t, of a treatment pattern may be determined.

Because the laser beam 201 and the OCT beam 301 share the same scanning component 830, the laser beam is preferably maintained inactive during azimuthal scanning of the OCT beam to avoid potential interference with the OCT beam. To this end, the laser source 200 that outputs the laser beam 201 may be turned off entirely so no laser beam is present, or the energy level of the laser source may be reduced so that the laser beam, while present together with the OCT beam, does not affect ocular tissue. In either case, laser treatment does not take place during the scanning of the OCT beam. Alternatively, the integrated surgical system 1000 may be configured with a separate scanning component 830 for the each of the laser beam 201 and the OCT beam 301, which would enable simultaneous OCT beam scanning and laser beam scanning.

With reference to FIG. 18, scanning the OCT beam 301 through the azimuthal slice 1820 includes moving the focus 1818 of the OCT beam to each of a plurality of azimuthal points 1818*b* between the iris boundary 1816 and the corneal boundary 1814. At each of the plurality of azimuthal points 1818*b*, the focus 1818 of the OCT beam 301 is moved in the +/−z direction to each of a plurality of points (not shown) between the anterior-chamber boundary 1810 and the sclera boundary 1812.

Returning to FIG. 17, and with additional reference to FIGS. 19*a* and 19*b*, at block 1708, a treatment pattern for a volume of ocular tissue is determined based on the circumferential OCT image 1902 and the azimuthal OCT image 1904. The volume of tissue to be treated may correspond to all or a portion of the segment 1804 of ocular tissue that was imaged. For example, a first dimension parameter and a second dimension parameter of the treatment pattern P1 may be derived from the azimuthal OCT image 1904. The first dimension parameter may be the thickness, t, of the treatment pattern in the z direction. The second dimension parameter may be the height, h, of the treatment pattern P1 in the y or azimuthal direction. A third dimension parameter of the treatment pattern P1 may be derived from the circumferential OCT image 1902. The third dimension parameter may be the width, w, of the treatment pattern P1 in the x or circumferential direction.

At block 1710 of FIG. 17, and with additional reference to FIG. 18, optical energy is delivered through the laser beam 201 in accordance with the determined treatment pattern P1. To this end, a focus of the laser beam 201 is placed at an initial depth in a target volume of ocular tissue bound by the first, second and third dimension parameters of the treatment pattern P1. Optical energy sufficient to affect ocular tissue is delivered during a three-dimensional scanning of the laser beam 201 through the treatment pattern P1, to thereby affect the target volume of ocular tissue. Three-dimensional scanning of the laser beam 201 through a treatment pattern P1 is described in detail above with reference to FIG. 14, and is not repeated here.

Because the laser beam 201 and the OCT beam 301 share the same scanning component 830, the OCT beam 301 is preferably maintained inactive during scanning of the laser beam 201 to avoid potential interference with the laser beam. To this end, the OCT imaging apparatus 300 that outputs the OCT beam 301 may be turned off entirely so no OCT beam is present, or the energy level of the OCT imaging apparatus may be reduced so that the OCT beam, while present together with the laser beam 201, does interfere with laser treatment. In either case, OCT imaging does not take place during the scanning of the laser beam 201. Alternatively, the integrated surgical system 1000 may be configured with a separate scanning component 830 for the each of the laser beam 201 and the OCT beam 301, which would enable simultaneous OCT beam scanning and laser beam scanning.

At block 1712 of FIG. 17, if an additional volume of ocular tissue is to be treated, the process returns to block 1704 and is repeated. If no additional volume is to be treated, the process ends at block 1714.

In accordance with embodiments disclosed herein, as part of an imaging procedure, one or more circumferential OCT images of the irido-corneal angle may be obtained by the integrated surgical system 1000 around the entire circumference of the irido-corneal angle. To this end, and with reference to FIGS. 18, 20, and 22, a method of imaging ocular tissue of an eye having a cornea, an iris, an anterior chamber, an irido-corneal angle, and a direction of view is disclosed.

Figure 20:
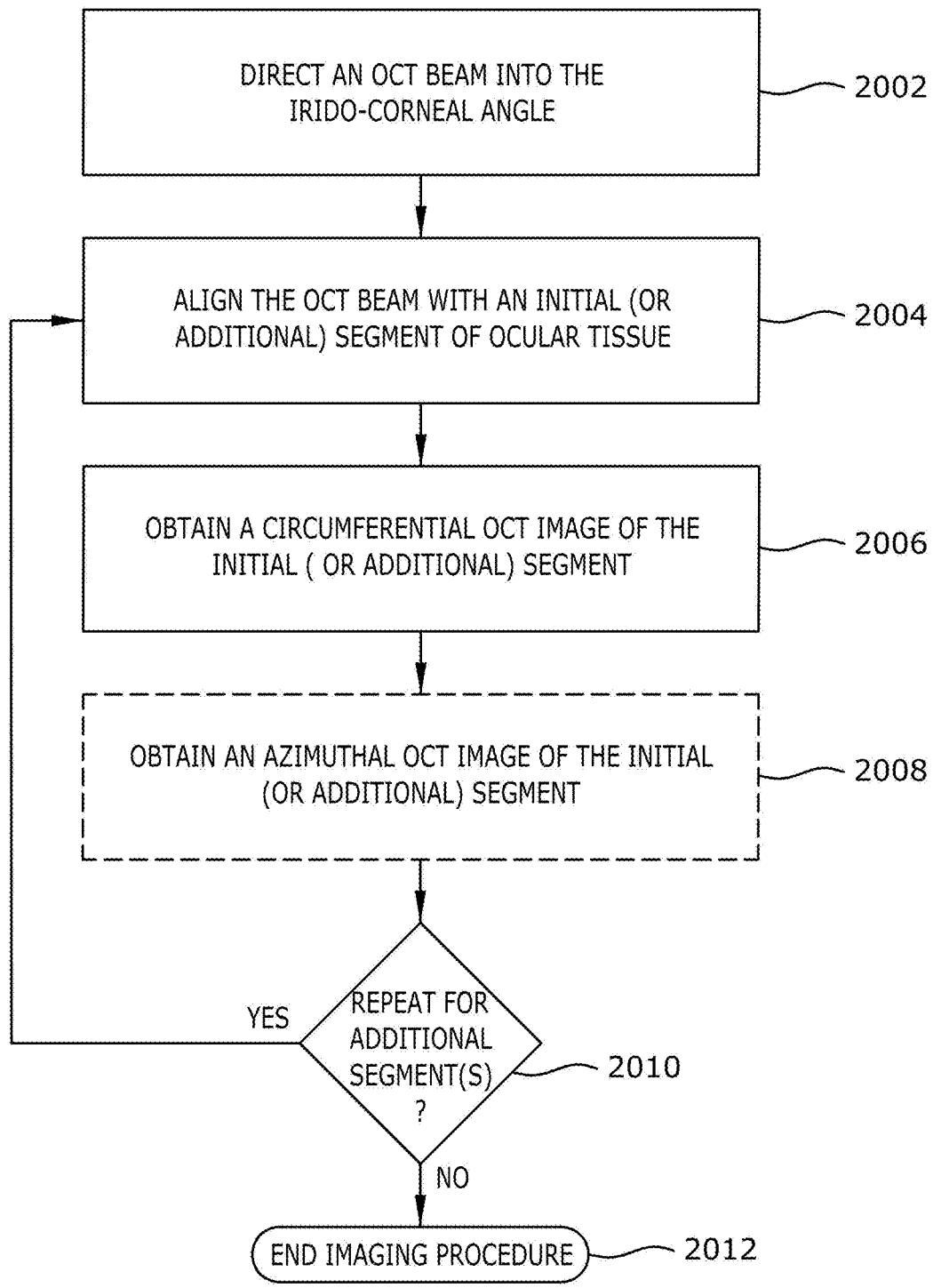
FIG. 20 is a flowchart of a method of imaging ocular tissue of an eye.

At block 2002 of FIG. 20, and with additional reference to FIGS. 9*a*, 9*b*, 18, and 22, an OCT beam 301 is directed through the cornea and the anterior chamber into the irido-corneal angle. The beams 301 may be so directed by a first optical subsystem 1001 having optics including a reflective surface 740 and an exit lens 710, which may be part of a focusing objective 700, and a window 801 of a patient interface 800. Optical features of the exit lens 710 and the window 801 are described above with reference to FIGS. 10a-10c. With reference to FIG. 10c, the optical path of the OCT beam 301 into the irido-corneal angle 13 passes through the cornea at an angle offset from an optical axis 705 within the direction of view of the eye 1, and without passing through the scleral spur.

At block 2004 of FIG. 20, and with additional reference to FIG. 18, the OCT beam 301 is aligned with an initial segment 1804 of ocular tissue of the irido-corneal angle. To this end, a second optical subsystem 1002 that includes an OCT imaging apparatus 300 that outputs the OCT beam 301, may be rotated relative to the optical axis 705. The second optical subsystem 1002 is rotated to place the optical path of the OCT beam 301 at a target point 1822 of the initial segment 1804. The target point 1822 may be at or near a midpoint between a first circumferential boundary 1806 of the initial segment 1804 and a second circumferential boundary 1808 of the initial segment. The target point 1822 may be at or near a midpoint between a corneal boundary 1814 of the initial segment 1804 and an iris boundary 1816 of the initial segment. The target point 1822 may be at the center of an anterior surface 1811 of the initial segment 1804. For example, the target point 1822 may be at the intersection of the midpoint of the initial segment 1804 in the circumferential direction and the midpoint of the initial segment in the azimuthal direction.

At block 2006 of FIG. 20, and with additional reference to FIG. 18, a circumferential OCT image of the initial segment 1804 of ocular tissue is obtained. The circumferential OCT image may be a 2D image, such as shown in FIG. 19a. To this end, the OCT beam 301 is scanned through a single circumferential plane 1802 of the initial segment 1804 of ocular tissue. The circumferential plane 1802 is bound by a first circumferential boundary 1806, a second circumferential boundary 1808, an anterior-chamber boundary 1810 adjacent the anterior chamber, and a sclera boundary 1812 adjacent the sclera; and is located in the y direction or azimuthal direction, somewhere between a corneal boundary 1814 adjacent the cornea, and an iris boundary 1816 adjacent the iris. The OCT beam 301 may be scanned through a circumferential plane 1802 a single time to obtain OCT data to construct a circumferential OCT image. The OCT beam 301 may be scanned through a single circumferential plane 1802 a plurality of times to obtain a corresponding plurality of OCT data to construct a corresponding plurality of circumferential OCT images. These plurality of circumferential OCT images may be processed together, e.g., averaged, to obtain a single circumferential OCT image.

In another embodiment, the circumferential OCT image may be a 3D image. To this end, the OCT beam 301 is scanned through each of a plurality of circumferential planes 1802 of the initial segment 1804 to obtain 2D OCT image data, e.g., voxels, for each circumferential plane. The plurality of circumferential planes 1802 may be adjacent each other. For example, with reference to FIG. 18, the plurality of circumferential planes 1802 may be stacked, one on top of the other, in the +/−y direction. A three-dimensional OCT image is constructed from the 2D OCT image data. For example, corresponding voxels from each circumferential plane 1802 may be stacked along a y axis or azimuthal axis to construct a 3D OCT image. The obtained 2D or 3D circumferential OCT image may be displayed in real-time, delayed by the time it takes to construct the 2D or 3D image.

At optional block 2008 of FIG. 20, and with additional reference to FIG. 18, an azimuthal OCT image of the initial segment 1804 of ocular tissue may be obtained. The azimuthal OCT image may be a 2D image, such as shown in FIG. 19b. To this end, the OCT beam 301 is scanned through an azimuthal slice 1820 of the initial segment 1804 of ocular tissue. The azimuthal slice 1820 may be bound by an anterior-chamber boundary 1810 adjacent the anterior chamber, a sclera boundary 1812 adjacent the sclera, a corneal boundary 1814 adjacent the cornea, and an iris boundary 1816 adjacent the iris; and is located in the x direction or circumferential direction somewhere between a first circumferential boundary 1806 and a second circumferential boundary 1808. The OCT beam 301 may be scanned through an azimuthal slice 1804 a single time to obtain OCT data to construct an azimuthal OCT image. The OCT beam 301 may be scanned through an azimuthal slice 1804 a plurality of times to obtain a corresponding plurality of OCT data to construct a corresponding plurality of azimuthal OCT images. These plurality of azimuthal OCT images may be processed together, e.g., averaged, to obtain a single azimuthal OCT image.

In another embodiment, the azimuthal OCT image may be a 3D image. To this end, the OCT beam 301 is scanned through each of a plurality of azimuthal slices 1820 of the initial segment 1804 to obtain 2D OCT image data, e.g., voxels, for each azimuthal slice. The plurality of azimuthal slices 1820 may be adjacent each other. For example, with reference to FIG. 18, the plurality of azimuthal slices may be arranged, side-by-side, in the +/−x direction. A three-dimensional OCT image is constructed from the 2D OCT image data. For example, corresponding voxels from each azimuthal slice 1820 may be aligned along the x axis or circumferential axis to construct a 3D OCT image. The obtained azimuthal OCT image may be displayed in real-time, delayed by the time it takes to construct the 2D or 3D image.

At block 2010 of FIG. 20, and with additional reference to FIG. 18, if additional segments 1830 of ocular tissue are to be imaged, the process returns to block 2004 and the aligning and obtaining are repeated. For example, the aligning and obtaining may be repeated for a plurality of additional segments 1830 around an entire circumference of the irido-corneal angle. To this end, the second optical subsystem 1002 may be rotated to place the optical path of the OCT beam 301 at a target point 1832 of an additional segment 1830. The target point 1832 may be at or near the center of an anterior surface 1838 of the additional segment. The target point 1832 may be, for example, at the intersection of the midpoint of the additional segment in the circumferential direction and the midpoint of the additional segment in the azimuthal direction. The process may be repeated for a plurality of additional segments around the entire circumferential angle. The series of 2D or 3D circumferential OCT images may be pieced together to obtain an 360-degree 2D or 3D circumferential OCT image of the irido-corneal angle.

Returning to block 2010, if no additional segments of ocular tissue are to be imaged, the process proceeds to block 2012 and the imaging procedure ends.

In accordance with embodiments disclosed herein, as part of an imaging procedure, a circumferential OCT image of the irido-corneal angle may be obtained by the integrated surgical system 1000 around the entire circumference of the irido-corneal angle. To this end, and with reference to FIGS. 18, 21, and 22, a method of imaging ocular tissue of an eye having a cornea, an iris, an anterior chamber, and a direction of view is disclosed.

Figure 21:
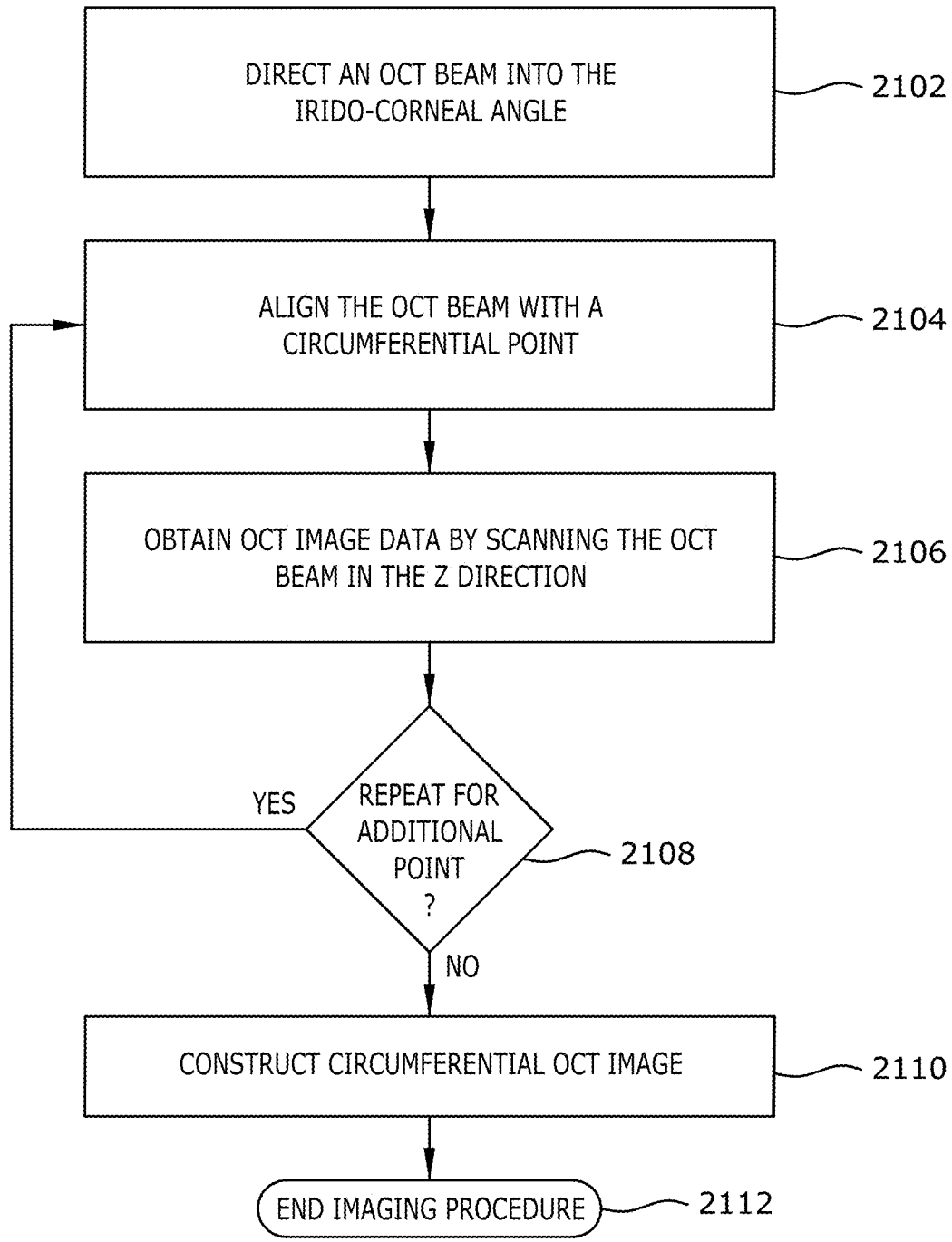
FIG. 21 is a flowchart of another method of imaging and treating ocular tissue of an eye.

At block 2102 of FIG. 21, and with additional reference to FIGS. 9a, 9b, 18, and 22, an OCT beam 301 is directed through the cornea and the anterior chamber into the irido-corneal angle. The beams 301 may be so directed by a first optical subsystem 1001 having optics including a reflecting surface 740 and an exit lens 710, which may be part of a focusing objective 700, and a window 801 of a patient interface 800. Optical features of the exit lens 710 and the window 801 are described above with reference to FIGS. 10a-10c. With reference to FIG. 10c, the optical path of the OCT beam 301 into the irido-corneal angle 13 passes through the cornea at an angle offset from an optical axis 705 within the direction of view of the eye 1, and without passing through the scleral spur.

At block 2104 of FIG. 21, and with additional reference to FIG. 18, for each of a plurality of circumferential points 1832, 1834, 1836 along a circumferential extent of the irido-corneal angle, the OCT beam 301 is aligned at a circumferential point. The circumferential extent may comprise all or a portion of the circumference of the irido-corneal angle, and the circumferential points 1832, 1834, 1836 are spaced apart along the extent. For example, adjacent circumferential points 1832, 1834, 1836 may be separated by ten microns.

At block 2106 of FIG. 21, and with additional reference to FIG. 18, while the OCT beam 301 is at the circumferential point 1832, 1834, 1836, the OCT beam is scanned in the +/−z direction between an anterior-chamber boundary 1810 adjacent the anterior chamber and a sclera boundary 1812 adjacent the sclera. In one configuration, the OCT beam 301 is aligned in place at each circumferential point 1832, 1834, 1836 for a time sufficient to allow scanning in the +/−z direction. The duration for which the OCT beam 301 is parked in place a circumferential point 1832, 1834, 1836 is so brief that it appears that the physical structure, e.g., a rotating turret assembly as described below with reference to FIGS. 22 and 23, that aligns the OCT beam 301 is continuously moving.

At block 2108 of FIG. 21, and with additional reference to FIG. 18, if additional circumferential points 1832, 1834, 1836 remain, the process returns to block 2104 and the aligning and obtaining are repeated. For example, the aligning and obtaining may be repeated for a plurality of additional circumferential points 1832, 1834, 1836 around all or a portion of an entire circumference of the irido-corneal angle.

Returning to block 2108, if no additional circumferential points 1832, 1834, 1836 remain, the process proceeds to block 2110 where a circumferential OCT image is constructed based on the obtained OCT image data. The process then proceeds to block 2112 and the imaging procedure ends.

The circumferential OCT image may be a 2D image, such as shown in FIG. 19a. To this end, the OCT beam 301 is scanned through a single circumferential plane 1802 around all or a portion of an entire circumference of the irido-corneal angle. The circumferential plane 1802 is bound by an anterior-chamber boundary 1810 adjacent the anterior chamber, and a sclera boundary 1812 adjacent the sclera; and is located in the y direction or azimuthal direction, somewhere between a corneal boundary 1814 adjacent the cornea, and an iris boundary 1816 adjacent the iris.

In another embodiment, the circumferential OCT image may be a 3D image. To this end, the OCT beam 301 is scanned through each of a plurality of circumferential planes 1802 around all or a portion of an entire circumference of the irido-corneal angle to obtain 2D OCT image data, e.g., voxels, for each circumferential plane. The plurality of circumferential planes 1802 may be adjacent each other. For example, with reference to FIG. 18, the plurality of circumferential planes 1802 may be stacked, one on top of the other, in the +/−y direction. A three-dimensional OCT image is constructed from the 2D OCT image data. For example, corresponding voxels from each circumferential plane 1802 may be stacked along a y axis or azimuthal axis to construct a 3D OCT image. The obtained 2D or 3D circumferential OCT image may be displayed in real-time, delayed by the time it takes to construct the 2D or 3D image.

Figure 22:
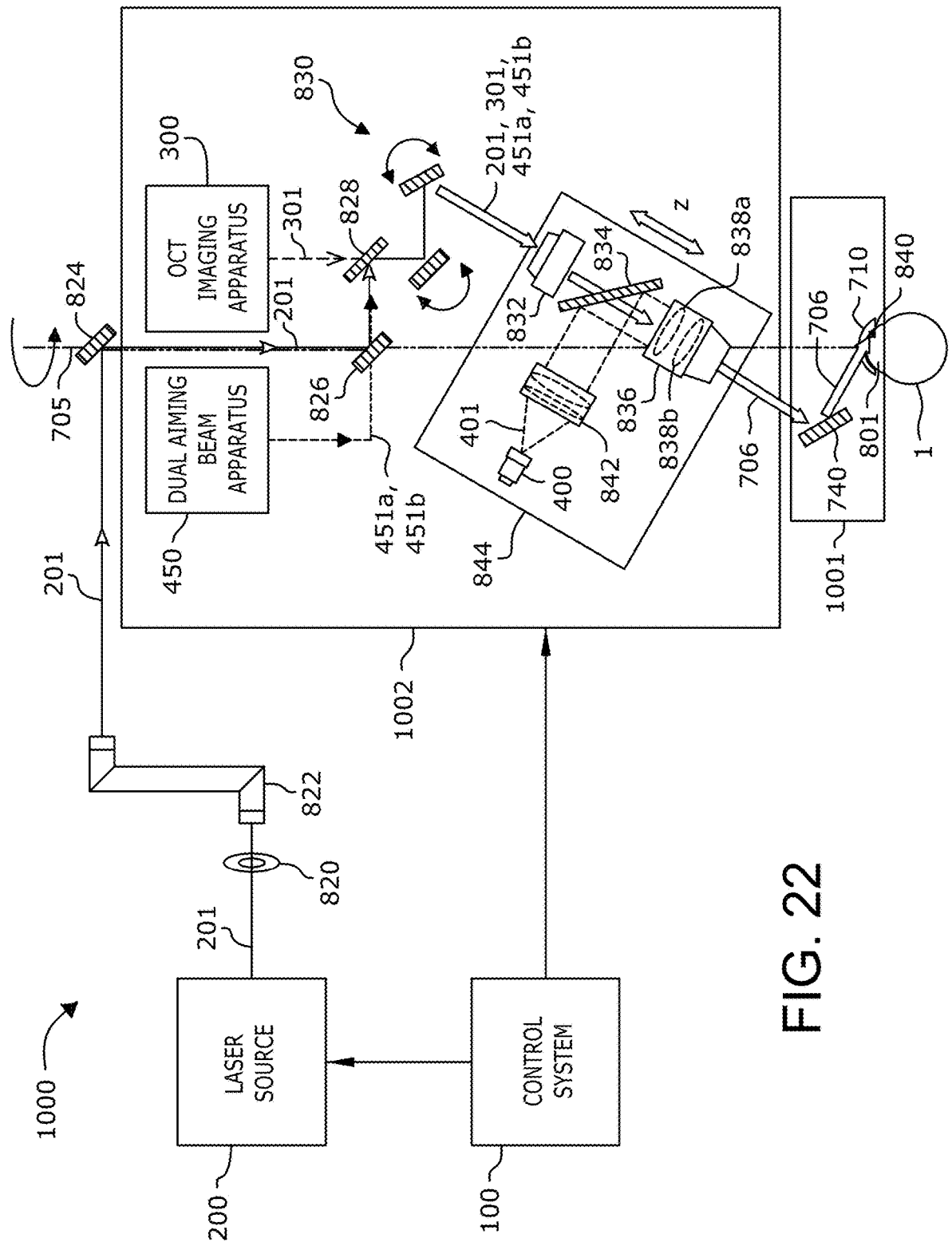
FIG. 22 is a detailed block diagram of the integrated surgical system of FIG. 7 including a rotatable optical subsystem that enables imaging and surgical scanning of the irido-corneal angle of the eye around the entire circumferential angle of the eye.
Figure 23:
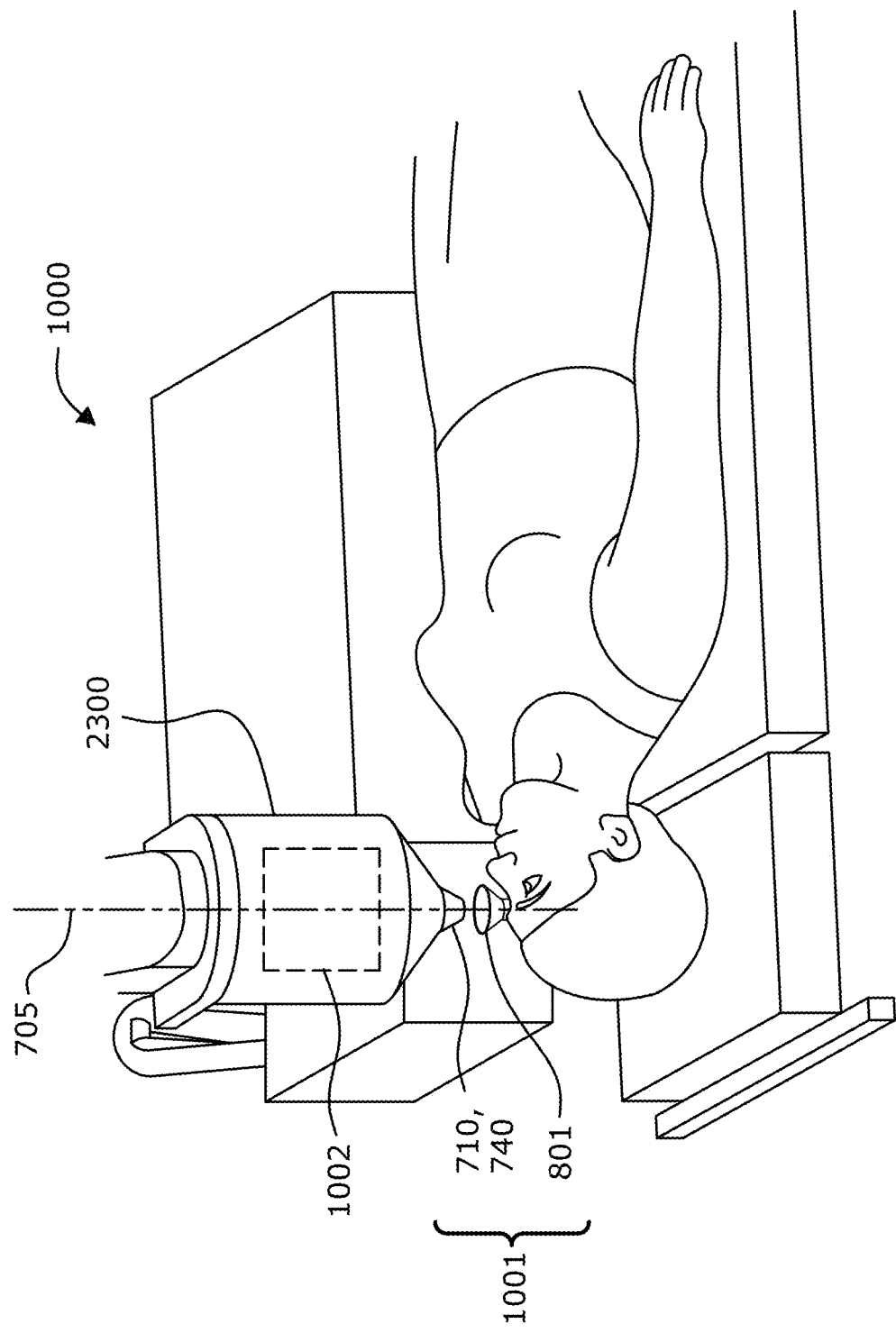
FIG. 23 is an illustration of a patient positioned on a surgical bed in proximity with an integrated surgical system.

Having thus described various methods of imaging and treating ocular tissue of an eye, a configuration of the integrated surgical system 1000, that enables the methods is disclosed with reference to FIGS. 22 and 23. This embodiment of the integrated surgical system 1000 includes a laser source 200 and a rotatable second optical subsystem 1002, also referred to as a turret assembly, that is optically coupled with a first optical subsystem 1001.

The first optical subsystem 1001 includes optics configured to establish a common optical axis 706 or common optical path through the cornea and the anterior chamber into the irido-corneal angle for each of an OCT beam 301 and a laser beam 201. The common optical axis 706 is offset from an optical axis 705 within the direction of view. In one configuration, the first optical subsystem 1001 includes a reflecting surface 740 in the form of a beam-folding mirror, an exit lens 710, and a window 810. In another configuration, the first optical subsystem 1001 includes a facet inside an optic that has a specialized coating for broadband reflection (visible, OCT and femtosecond) and low difference between s and p polarization group delay dispersion (GDD), an exit lens 710 associated with the optic, and a window 810. With reference to FIGS. 9a, 9b and 10b, components of the first optical subsystem 1001 may be included in different physical structures. For example, the exit lens 710 and the reflective surface 740 may be part of a focusing objective 700 and the window 801 may be part of a patient interface 800.

The second optical subsystem 1002 includes an OCT imaging apparatus 300, an optional dual aiming beam apparatus 450, a scanner component 830 that may comprise a pair of galvanometer scanning mirrors, a visual observation apparatus 400, and various optical components mounted on a plate 844 that is instrumented with a motorized scanner configured to move the optical axis 706 of the components back and forth in the z direction. The optical components mounted on the plate 844 include a dichroic mirror 834, a telescope 842, and focusing optics, e.g., a back-end objective 832 having two lenses (not shown) and a front-end objective 836 with a first objective lens 838a and a second objective lens 838b. The visual observation apparatus 400 is also mounted in the plate 844.

Other optical components not mounted on the plate 844, e.g., a mirror 826 and a first dichroic mirror 828, included in the second optical subsystem 1002 are configured to optically couple various beams output by the laser source 200, the OCT imaging apparatus 300, and the dual aiming beam apparatus with the focusing optics 832, 836. A fixed turning mirror 824 separate from the second optical subsystem 1002 is arranged relative to the laser source 200 and the second optical subsystem to direct a laser beam 201 toward components of the second optical subsystem. The second optical subsystem 1002 is configured to rotate relative to an optical axis 705. This rotation enables optical access to the whole 360-degree circumference of the irido-corneal angle 13 of the eye 1. To this end, and with reference to FIG. 23, the second optical subsystem 1002 is housed within a turret 2300 mounted to rotate about the optical axis 705.

Returning to FIG. 22, the OCT imaging apparatus 300 included in the second optical subsystem 1002 is configured to transmit an OCT (near infrared) beam 301 onto the first dichroic mirror 828, which transmits the OCT beam. The OCT beam 301 and a laser beam 201 emitted by the laser source 200 are arranged such that both the OCT beam and laser beam are co-aligned and parallel upon emerging from the first dichroic mirror 828. The OCT beam 301 is directed into the scanner component 830 and into the back-end objective 832. The back-end objective 832 functions as an expanding telescope that increases the diameter of the OCT beam 301 and also pre-compensates for astigmatism that will be introduced by the human cornea. The expanded OCT beam is then incident onto the second dichroic mirror 834. The second dichroic mirror 834 is configured to transmit the OCT wavelength, e.g., 850 nm, and to not reflect the OCT wavelength. The second dichroic mirror 834 is further configured to transmit near-infrared and infrared light. The second dichroic mirror 834 is also configured to reflect visible light. The expanded OCT beam is then incident into the first objective lens 838a included in the front-end objective 836. The OCT beam continues to diverge as it passes through the first objective lens 838a.

The OCT beam is then incident into the second objective lens 838b. The OCT beam 301 exits the second objective lens 838b and enters the first optical subsystem 1001. The OCT beam 301 may be directed into a reflective surface 740 in the form of a beam-folding mirror, through the exit lens 710 and the window 801, and into the irido-corneal angle. In the case of a reflective surface 740 in the form of a facet in an optic that has a specialized coating for broadband reflection (visible, OCT and femtosecond) and low difference between s and p polarization GDD, the OCT beam 301 refracts through a convex surface of the optic, strikes the facet and internally reflects through the optic and then exits through a concave surface corresponding to the exit lens 710. The OCT beam 301 then passes through the window 801, the cornea, and the anterior chamber, and to a spot 840 in the irido-corneal angle at a predetermined distance from the exit surface of the second objective lens 838b.

As described above with reference to FIGS. 18 and 21, during OCT scanning an OCT image of the entire circumferential angle may be obtained by rotating the second optical subsystem 1002, and thus the focus 1818 of the OCT beam 301, around the entire circumferential angle. While the rotation may appear continuous, it comprises a series of discrete movements of the second optical assembly 1002 during which the assembly is rotated to a circumferential point 1832 along the circumferential angle, stopped or parked for a brief period of time to allow scanning of the OCT beam in the +/−z direction, and then rotated to the next circumferential point 1834, 1836.

Alternatively, as described above with reference to FIGS. 18 and 20, during OCT scanning a series of individual OCT images, each corresponding to a segment 1804, 1830 of the circumferential angle, may be obtained. For example, individual OCT images may correspond to 4 to 20 degree segments of ocular tissue of the irido-corneal angle. As previously mentioned, the circumferential scanning range can be made as small as desired. The minimum length of 1 mm is a convenient distance that corresponds to about 4 degrees of the irido-corneal angle. In this case, the second optical subsystem 1002 may be parked at or near the center of a segment 1804, 1830 of ocular tissue and the circumferential OCT image is obtained by scanning the OCT beam within the segment using the scanning mirrors 830. This type of scanning is more efficient in cases where OCT images of only one or more particular segments 1804, 1830 of the circumferential angle are desired. Whereas, OCT scanning through rotation of the second optical subsystem 1002 is more desirable in cases where the surgeon wants to initially scan the entire circumferential angle to identify target areas for surgical treatment.

Returning to FIG. 22, the laser source 200 is configured to emit a laser beam 201 of femtosecond light pulses through a control shutter 820 and into an articulated arm 822. The articulated arm 822 transmits the laser beam 201 onto the turning mirror 824 that reflects the laser wavelength onto the mirror 826 that reflects the laser wavelength onto the first dichroic mirror 828. The mirror 826 may be a dichroic mirror.

The laser beam 201 is directed into the scanning component 830 and into the back-end objective 832. The back-end objective 832 functions as an expanding telescope that increases the diameter of the laser beam 201 and pre-compensates for astigmatism that will be introduced by the human cornea. The expanded laser beam is then incident onto a second dichroic mirror 834. The second dichroic mirror 834 is configured to transmit the laser wavelength, e.g., 1030 nm in the case of a femtosecond laser, and to not reflect the laser wavelength. The expanded laser beam is then incident into the first objective lens 838a included in the front-end objective 836. The laser beam 201 continues to diverge as it passes through the first objective lens 838a.

The laser beam 201 is then incident into the second objective lens 838b. The laser beam 201 exits the second objective lens 838b and enters the first optical subsystem 1001. The laser beam 201 may be directed into a reflective surface 740 in the form of a beam-folding mirror, through the exit lens 710 and the window 801, and into the irido-corneal angle. In the case of a reflective surface 740 in the form of a facet in an optic that has a specialized coating for broadband reflection (visible, OCT and femtosecond) and low difference between s and p polarization GDD, the laser beam 201 refracts through a convex surface of the optic, strikes the facet and internally reflects through the optic and then exits through a concave surface corresponding to the exit lens 710. The laser beam 201 then passes through the window 801, the cornea, and the anterior chamber, and to a spot 840 in the irido-corneal angle at a predetermined distance from the exit surface of the second objective lens 838b.

Regarding the diameter of the expanded laser beam, the diameter of the beam when it enters the first objective lens 838a in the front-end objective 836 determines the final numerical aperture of the laser beam. The larger the diameter of the expanded laser beam, the greater the numerical aperture. In general, laser beams with greater numerical apertures are focused onto smaller points 840. The beam diameter and the numerical aperture are design choices that depend on the intended use of the device. In the integrated surgical system 1000, the diameter of the expanded laser beam is about 6 mm.

With reference to FIG. 18, during laser scanning, laser treatment may be delivered to a series of volumes of ocular tissue, each volume generally corresponding to a segment 1804, 1830 of the circumferential angle. To this end, the second optical subsystem 1002 may be rotated and parked to align the laser beam 201 at or near the center of a first segment 1804 of ocular tissue. The laser beam 201 is then scanned in accordance with a treatment pattern derived for the first segment 1804 using the scanning component 830.

The second optical subsystem 1002 is then rotated and parked to align the laser beam 201 at or near the center of the next segment 1830 of ocular tissue and the laser is scanned in accordance with a treatment pattern derived for that segment 1830. The rotating and scanning process may be repeated until all or a portion of the circumferential angle is treated.

The visual observation apparatus 400 enables visualization of the circumferential angle. In one configuration, the visual observation apparatus 400 includes an illumination source and a video camera. The illumination source component of the visual observation apparatus 400 shines an illumination beam 401 through the telescope 842 and onto the second dichroic mirror 834. The illumination beam 401 reflects from the second dichroic mirror 834 into the first objective lens 838a included in the front-end objective 836. The illumination beam 401 passes through the first objective lens 838a and into the second objective lens 838b. The second objective lens 838b focuses visible light from the illumination beam 401 to illuminate an area within the circumferential angle. The illumination beam 401 diffuses scatters inside the tissue and back-scattered light that exits the tissue is reflected off the facet inside the superdome, returning back through the front-end objective 836 and onto the second dichroic mirror 834. The returning illumination beam 401 of light is focused by the telescope 842 onto the video camera component of the visual observation apparatus 400 where it forms an image of the circumferential angle. An aperture is located at the entrance of the visual observation apparatus to limit the solid angle of collection to provide the required depth of field and form a high resolution image across the field-of-view.

The dual aiming beam apparatus 450 enables detection of an anterior surface 1811, 1834 of the trabecular meshwork 12 facing the anterior chamber. To this end, the dual aiming beam apparatus 450 transmits two separate aiming beams of light 451a, 451b toward the mirror 826. In one embodiment, the mirror 826 is sized and positioned so the dual aiming beams of light 451a, 451b do not hit or interact with the mirror, and instead are transmitting directly onto the first dichroic mirror 828. In another embodiment, the dual aiming beams of light 451a, 451b do interact with the mirror and the mirror 826 is configured to transmit the dual aiming beams 451a, 451b onto the first dichroic mirror 828. The dual aiming beams 451a, 451b and laser beam 201, if present, are arranged such that both the aiming beam and laser beam are co-aligned and parallel upon emerging from the first dichroic mirror 828. The OCT beam 301 and dual aiming beams 451a, 451b are directed into the pair of scanning mirrors 830 and into the back-end objective 832.

The back-end objective 832 function as an expanding telescope and increases the diameter of the dual aiming beams 451a, 451b. The expanded dual aiming beams 451a, 451b are then incident onto the second dichroic mirror 834. The second dichroic mirror 834 is configured to transmit the dual aiming beams wavelengths, and to not reflect the dual aiming beam wavelengths. The expanded dual aiming beams 451a, 451b are then incident into the first objective lens 838a included in the front-end objective 836. The dual aiming beams 451a, 451b pass through the first objective lens 838a and into the second objective lens 838b. The dual aiming beams 451a, 451b continue to diverge as they passes through the first objective lens 838a.

The dual aiming beams 451a, 451b are then incident into the second objective lens 838b. The dual aiming beams 451a, 451b exit the second objective lens 838b and enter the first optical subsystem 1001. The dual aiming beams 451a, 451b may be directed into a reflective surface 740 in the form of a beam-folding mirror, through the exit lens 710 and the window 801, and into the irido-corneal angle. In the case of a reflective surface 740 in the form of a facet in an optic that has a specialized coating for broadband reflection (visible, OCT and femtosecond) and low difference between s and p polarization GDD, the dual aiming beams 451a, 451b refract through a convex surface of the optic, strike the facet and internally reflect through the optic and then exit through a concave surface corresponding to the exit lens 710. The dual aiming beams 451a, 451b then pass through the window 810, the cornea, and the anterior chamber, and to a spot 840 in the irido-corneal angle at a predetermined distance from the exit surface of the second objective lens 838b.

The dual aiming beams of light 451a, 451b from the circumferential angle at the point 840 re-enter the front-end objective 836. A fraction of light from the dual aiming beams of light 451a, 451b is reflected by the second dichroic mirror 834 into the telescope 842. The telescope 842 focuses the dual aiming beams of light 451a, 451b onto the visual observation apparatus 400 where an image of the aiming beams is formed. The dual aiming beams of light 451a, 451b may be used to detect the surface of the trabecular meshwork. Details of such use are described in U.S. patent application Ser. No. 16/781,770, titled "System and Method for Locating a Surface of Ocular Tissue for Glaucoma Surgery Based on Dual Aiming Beams."

This embodiment of the integrated surgical system 1000 enables visualize of structures of the irido-corneal angle relevant to laser treatment for glaucoma, including the trabecular meshwork, Schlemm's canal, and the collector channels. Specifically, it is preferred that femtosecond laser treatment of the trabecular meshwork be performed near the locations of collector channels. Doing so promotes a more efficient outflow of aqueous humor through the trabecular meshwork, into Schlemm's canal, though the collector channels, and out to the venous system.

The azimuthal OCT images captured by the integrated surgical system 1000 reveal the locations of the trabecular meshwork and the underlying Schlemm's canal. Azimuthal images, however, may not always reveal the location of collector channels since these channels are small, and discrete that are easily missed. The circumferential OCT images captured by the integrated surgical system 1000 compensate for inadequate azimuthal OCT images by revealing the location of the trabecular meshwork, Schlemm's canal, and multiple collector channels.

The various aspects of this disclosure are provided to enable one of ordinary skill in the art to practice the present invention. Various modifications to exemplary embodiments presented throughout this disclosure will be readily apparent to those skilled in the art. Thus, the claims are not intended to be limited to the various aspects of this disclosure, but are to be accorded the full scope consistent with the language of the claims. All structural and functional equivalents to the various components of the exemplary embodiments described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for."

It is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. An integrated surgical system for imaging and treating ocular tissue of an eye having a cornea, an iris, an anterior chamber, an irido-corneal angle, and a direction of view, the integrated surgical system comprising:
    a first optical subsystem configured to establish a common optical path through the cornea and the anterior chamber into the irido-corneal angle, wherein the common optical path is offset from an optical axis within the direction of view;
    a laser source configured to output a laser beam;
    a second optical subsystem configured to rotate relative to the optical axis, the second optical sub system comprising:
        an optical coherence tomography (OCT) imaging apparatus configured to output an OCT beam,
        a scanning component optically coupled with the laser source and the OCT imaging apparatus to receive each of the laser beam and the OCT beam, and
        focusing optics optically coupled between the scanning component and the first optical subsystem; and
    a control system coupled with the laser source and the second optical subsystem and configured to affect operation of the laser source, the OCT imaging apparatus, the scanning component, and the focusing optics to:
        obtain a circumferential OCT image of the irido-corneal angle;
        obtain an azimuthal OCT image of the irido-corneal angle; and
        deliver optical energy through the laser beam in accordance with a treatment pattern for a volume of ocular tissue of the irido-corneal angle, wherein the treatment pattern is based on the circumferential OCT image and the azimuthal OCT image.

2. The integrated surgical system of claim 1, wherein the control system is configured to obtain the circumferential OCT image by being further configured to:
    scan the OCT beam through a circumferential plane of the volume of ocular tissue, the circumferential plane bound by a first circumferential boundary, a second circumferential boundary, an anterior-chamber boundary adjacent the anterior chamber, and a sclera boundary adjacent a sclera.

3. The integrated surgical system of claim 2, wherein the control system is configured to scan the OCT beam through the circumferential plane by being further configured to:
    move a focus of the OCT beam to each of a plurality of circumferential points between the first circumferential boundary the second circumferential boundary; and
    at each of the plurality of circumferential points, move the focus of the OCT beam to each of a plurality of points between the anterior-chamber boundary and the sclera boundary.

4. The integrated surgical system of claim 3, wherein the control system is configured to move a focus of the OCT beam to each of a plurality of circumferential points by being further configured to:
    rotate the second optical subsystem relative to the optical axis, to each of the plurality of circumferential points.

5. The integrated surgical system of claim 1, wherein the control system is configured to obtain an azimuthal OCT image by being further configured to:
    scan the OCT beam through an azimuthal slice of a volume of ocular tissue, the azimuthal slice bound by an anterior-chamber boundary adjacent the anterior chamber, a sclera boundary adjacent a sclera, a corneal boundary adjacent the cornea, and an iris boundary adjacent the iris.

6. The integrated surgical system of claim 5, wherein the control system is further configured to scan the OCT beam through the azimuthal slice by being further configured to:
    move a focus of the OCT beam to each of a plurality of azimuthal points between the iris boundary and the corneal boundary; and
    at each of the plurality of azimuthal points, move the focus of the OCT beam to each of a plurality of points between the anterior-chamber boundary and the sclera boundary.

7. The integrated surgical system of claim 1, wherein the control system is further configured to determine a treatment pattern for the volume of ocular tissue.

8. The integrated surgical system of claim 7, wherein the control system is configured to determine the treatment pattern by being further configured to:
    derive a first dimension parameter and a second dimension parameter of the treatment pattern from the azimuthal OCT image; and
    derive a third dimension parameter of the treatment pattern from the circumferential OCT image.

9. The integrated surgical system of claim 8, wherein the first dimension parameter, the second dimension parameter, and the third dimension parameter respectively correspond to a thickness, a height, and a width.

10. The integrated surgical system of claim 8, wherein the treatment pattern for the volume of ocular tissue is based on a plurality of circumferential OCT images and azimuthal OCT images.

11. The integrated surgical system of claim 7, wherein the control system is configured to deliver optical energy through the laser beam in accordance with the treatment pattern by being further configured to:
    place a focus of the laser beam at an initial depth in a target volume of ocular tissue bound by the treatment pattern; and
    deliver optical energy sufficient to affect ocular tissue during a three-dimensional scanning of the laser beam through the treatment pattern, to thereby affect the target volume of ocular tissue.

12. A method of imaging and treating ocular tissue of an eye having a cornea, an iris, an anterior chamber, an irido-corneal angle, and a direction of view, the method comprising:
    establishing a common optical path through the cornea and the anterior chamber into the irido-corneal angle for each of an optical coherence tomography (OCT) beam and a laser beam, wherein the common optical path is offset from an optical axis within the direction of view;
    obtaining a circumferential OCT image of the irido-corneal angle;
    obtaining an azimuthal OCT image of the irido-corneal angle;

determining a treatment pattern for a volume of ocular tissue of the irido-corneal angle based on the circumferential OCT image and the azimuthal OCT image; and delivering optical energy through the laser beam in accordance with the treatment pattern.

13. The method of claim 12, wherein, obtaining the circumferential OCT image comprises:

scanning the OCT beam through a circumferential plane of the volume of ocular tissue, the circumferential plane bound by a first circumferential boundary, a second circumferential boundary, an anterior-chamber boundary adjacent the anterior chamber, and a sclera boundary adjacent a sclera.

14. The method of claim 13, wherein the laser beam is inactive during the scanning of the OCT beam.

15. The method of claim 13, wherein the circumferential plane is located between a corneal boundary adjacent the cornea and an iris boundary adjacent the iris.

16. The method of claim 13, wherein scanning the OCT beam through the circumferential plane comprises:

moving a focus of the OCT beam to each of a plurality of circumferential points between the first circumferential boundary the second circumferential boundary; and at each of the plurality of circumferential points, moving the focus of the OCT beam to each of a plurality of points between the anterior-chamber boundary and the sclera boundary.

17. The method of claim 16, wherein moving a focus of the OCT beam to each of a plurality of circumferential points comprises:

rotating an optical subsystem relative to the optical axis, to each of the plurality of circumferential points, wherein the optical subsystem comprises an OCT imaging apparatus that outputs the OCT beam, and focusing optics that move the focus of the OCT beam.

18. The method of claim 12, wherein obtaining an azimuthal OCT image comprises:

scanning the OCT beam through an azimuthal slice of a volume of ocular tissue, the azimuthal slice bound by an anterior-chamber boundary adjacent the anterior chamber, a sclera boundary adjacent a sclera, a corneal boundary adjacent the cornea, and an iris boundary adjacent the iris.

19. The method of claim 18, wherein the laser beam is inactive during the scanning of the OCT beam.

20. The method of claim 18, wherein the azimuthal slice is located between a first circumferential boundary and a second circumferential boundary.

21. The method of claim 18, wherein scanning the OCT beam through the azimuthal slice comprises:

moving a focus of the OCT beam to each of a plurality of azimuthal points between the iris boundary and the corneal boundary; and at each of the plurality of azimuthal points, moving the focus of the OCT beam to each of a plurality of points between the anterior-chamber boundary and the sclera boundary.

22. The method of claim 12, wherein determining a treatment pattern for the volume of ocular tissue based on the circumferential OCT image and the azimuthal OCT image comprises:

deriving a first dimension parameter and a second dimension parameter of the treatment pattern from the azimuthal OCT image; and deriving a third dimension parameter of the treatment pattern from the circumferential OCT image.

23. The method of claim 22, wherein the treatment pattern for the volume of ocular tissue is based on a plurality of circumferential OCT images and azimuthal OCT images.

24. The method of claim 22, wherein delivering optical energy through the laser beam in accordance with the treatment pattern comprises:

placing a focus of the laser beam at an initial depth in a target volume of ocular tissue bound by the first, second and third dimension parameters of the treatment pattern; and delivering optical energy sufficient to affect ocular tissue during a three-dimensional scanning of the laser beam through the treatment pattern, to thereby affect the target volume of ocular tissue.

25. The method of claim 24, wherein the OCT beam is inactive during scanning of the laser beam.

26. The method of claim 12, further comprising repeating the obtaining a circumferential OCT image, the obtaining an azimuthal OCT image, the determining a treatment pattern, and the delivering optical energy for at least one additional volume of ocular tissue of the irido-corneal angle.

* * * * *